(12) United States Patent
Bradley et al.

(10) Patent No.: US 7,482,375 B2
(45) Date of Patent: *Jan. 27, 2009

(54) COMPOUNDS USEFUL IN THERAPY

(75) Inventors: Paul Anthony Bradley, Sandwich (GB); Kevin Neil Dack, Sandwich (GB); Ian Roger Marsh, Sandwich (GB)

(73) Assignee: Pfizer Inc., New York, NY (US)

( * ) Notice: Subject to any disclaimer, the term of this patent is extended or adjusted under 35 U.S.C. 154(b) by 357 days.

This patent is subject to a terminal disclaimer.

(21) Appl. No.: 11/408,286

(22) Filed: Apr. 18, 2006

(65) Prior Publication Data

US 2006/0241125 A1  Oct. 26, 2006

Related U.S. Application Data

(60) Provisional application No. 60/673,544, filed on Apr. 20, 2005.

(51) Int. Cl.
*A61K 31/415* (2006.01)
*C07D 231/10* (2006.01)

(52) U.S. Cl. .............. 514/407; 548/356.1; 548/366.1; 548/370.7; 514/403; 514/406

(58) Field of Classification Search ............. 548/356.1, 548/366.1, 370.7; 514/403, 406, 407
See application file for complete search history.

(56) References Cited

U.S. PATENT DOCUMENTS

| 6,933,312 B2 * | 8/2005 | Price et al. .......... 514/406 |
| 7,109,228 B2 * | 9/2006 | Jones et al. .......... 514/407 |
| 2006/0020012 A1 | 1/2006 | Jones et al. .......... 514/407 |

FOREIGN PATENT DOCUMENTS

| DE | 3621024 | 6/1986 |
| WO | WO02085860 | 10/2002 |

OTHER PUBLICATIONS

Price et al (2004): STN International HCAPLUS database, (Columbus, Ohio), Accession No. 2004:308433.*

* cited by examiner

*Primary Examiner*—Golam M Shameem
(74) *Attorney, Agent, or Firm*—Gregg C. Benson; Carl J. Goddard

(57) ABSTRACT

Compounds of formula (I),

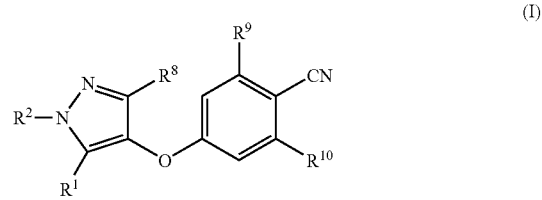

or pharmaceutically acceptable derivatives thereof, wherein:
$R^1$ represents H, $C_{1-6}$-alkyl, $C_{1-6}$alkyloxy, $C_{3-8}$cycloalkyl, or halo;
$R^2$ represents H, $C_{1-6}$alkyl (optionally substituted by $R^3$), phenyl (optionally substituted by CN), or Het;
$R^3$ represents OH, CN, Het, —$R^4$—$C_{1-6}$alkyl, or $CONR^5R^6$;
$R^4$ represents —$CO_2$—, or —O—;
$R^5$ and $R^6$ independently represent H, $C_{1-6}$alkyl (optionally substituted by $OR^7$) or $C_{3-8}$cycloalkyl;
$R^7$ represents H or $C_{1-6}$alkyl;
Het represents a five or six membered aromatic heterocyclic group containing (i) from one to four nitrogen heteroatom(s) or (ii) one or two nitrogen heteroatom(s) and one oxygen or one sulphur heteroatom or (iii)one or two oxygen or sulphur heteroatom(s), said heterocyclic group being optionally substituted by one or more groups selected from CN and $C_{1-6}$alkyl;
$R^8$ represents $C_{1-6}$alkyl, $C_{1-6}$alkyloxy, $C_{3-8}$cycloalkyl, or halo;
$R^9$ and $R^{10}$ independently represent H, $C_{1-6}$alkyl, $C_{1-6}$alkyloxy, CN, $CF_3$ or halo;
may be useful for treating endometriosis, uterine fibroids (leiomyomata), menorrhagia, adenomyosis, primary and secondary dysmenorrhoea (including symptoms of dyspareunia, dyschexia and chronic pelvic pain), or chronic pelvic pain syndrome.

14 Claims, No Drawings

COMPOUNDS USEFUL IN THERAPY

This application claims priority to U.S. Provisional Application No. 60/673,544, filed Apr. 20, 2005.

BACKGROUND OF THE INVENTION

This invention relates to novel compounds, and their derivatives, which are useful in therapy and to processes for their preparation. It also relates to intermediates used in the preparation of such compounds and derivatives, compositions containing them and their uses.

Endometriosis is a common gynaecological disease that affects 10-20% women of reproductive age and manifests itself in the presence of functional ectopic endometrial glands and stroma at locations outside the uterine cavity {Prentice, A. (2001). Bmj 323, 93-95.}. Patients with endometriosis may present with many different symptoms and severity. Most commonly this is dysmenorrhoea, but chronic pelvic pain, dyspareunia, dyschexia, menorrhagia, lower abdominal or back pain, infertility, bloating and pain on micturition are also part of the constellation of symptoms of endometriosis.

Originally described by Von Rokitansky in 1860 {Von Rokitansky, C. (1860). Ztsch K K Gesellsch der Aerzte zu Wien 37, 577-581.}, the exact pathogenesis of endometriosis is unclear {Witz, C. A. (1999). Clinical Obstetrics & Gynaecology 42, 566-585.; Witz, C. A. (2002). Gynaecologic & Obstetric Investigation 53, 52-62.}, but the most widely accepted theory is the implantation, or Sampson, theory {Sampson, J. A. (1927). American Journal of Obstetrics & Gynaecology 14, 422-429.}. The Sampson theory proposes that the development of endometriosis is a consequence of retrograde dissemination and implantation of andometrial tissue into the peritoneal cavity during menstruation. Following attachment, the fragments of endometrium recruit a vascular supply and undergo cycles of proliferation and shedding under local and systemic hormonal controls. In women with patent fallopian tubes, retrograde menstruation appears to be a universal phenomenon {Liu, D. T. (Hitchcock, A.). British Journal of Obstetrics & Gynaecology 93, 859-862.}. The disease often manifests itself as rectovaginal endometriosis or adenomyosis, ovarian cystic endometriomas and, most commonly, peritoneal endometriosis. The major sites of attachment and lesion growth within the pelvis are the ovaries, broad and round ligaments, fallopian tubes, cervix, vagina, peritoneum and the pouch of Douglas. At its most severe, endometriosis can cause profound structural modification to peritoneal cavity, including multi-organ adhesions and fibrosis.

Symptomatic endometriosis can be managed medically and surgically, where the intention is to remove the ectopic lesion tissue. Surgical intervention can be either conservative, aiming to preserve the reproductive potential of the patient, or comparatively radical for severe disease, involving dissection of the urinary tract, bowel, and rectovaginal septum, or total abdominal hysterectomy and bilateral salpingo-oopherectomy. Medical pharmacological treatments such as the androgenic therapies, danazol and gestrinone, the constellation of GnRH agonists, buserelin, goserelin, leuprolide, nafarelin and triptorelin, GnRH antagonists, cetrorelix and abarelix, as well as the progestogens, including medroxyprogesterone acetate, induce lesion atrophy by suppressing the production of estrogen. These approaches are not without unwanted side effects; danazol and gestrinone include weight gain, hirsuitism, acne, mood changes and metabolic effects on the cardiovascular system. The group of GnRH agonists and antagonists are found to cause a profound suppression of estrogen leading to vasomotor effects (hot flashes) and depletion of bone mineral density, which restricts their use to only six months of therapy. The group of progestogens, including medroxyprogesterone acetate, suppress the gonadotropins, but do not down-regulate ovarian estrogen production to the same extent as the GnRH analogues. The side effects include irregular bleeding, bloating, weight gain and metabolic effects on the cardiovascular system.

Uterine leiomyomas {Flake, G. P., et al. (2003). Environmental Health Perspectives 111, 1037-1054.; Walker, C. L. (2002). Recent Progress in Hormone Research 57, 277-294.}, or fibroids, are the most common benign tumours found in women and occur in the majority of women by the time they reach the menopause. Although uterine fibroids are the most frequent indication for hysterectomy in the United States, as with endometriosis, remarkably little is known about the underlying pathophysiology of the disease. As with endometriotic lesions, the presence of enlarged uterine fibroids is associated with abnormal uterine bleeding, dysmenorrhoea, pelvic pain and infertility. Outside of surgical management, medical treatments commonly used for endometriosis, such as GnRH analogues or danazol, have been shown to suppress fibroid growth by inducing a reversible hypoestrogenic state {Chrisp, P., and Goa, K. L. (1990). Drugs 39, 523-551.; Chrisp, P., and Goa, K. L. (1991). Drugs 41, 254-288.; De Leo, V., et al. (2002). Drug Safety 25, 759-779.; Ishihara, H., et al. (2003). Fertility & Sterility 79, 735-742.}. However, the future disease management of both uterine fibroids and endometriosis will rely on the development of more effective, well-tolerated and safer agents than those that are currently available.

Steroidal progestins (i.e., progesterone receptor agonists) are commonly used in women's health, such as in contraception and hormone therapy and for the treatment of gynecological disorders. Recent studies in women and in nonhuman primates also indicate that progesterone receptor antagonists may have potential applications in contraception and for the treatment of reproductive disorders such as fibroids and endometriosis. Currently, all clinically available progesterone receptor agonists and antagonists are steroidal compounds. They often cause various side effects due to their functional interactions with other steroid receptors or because of effects associated with their steroidal metabolites {Winneker, Richard C. et al.; Endocrinology and Reproductive Disorders Division, Women's Health Research Institute, Collegeville, Pa., USA. Seminars in Reproductive Medicine (2005), 23(1), 46-57}.

Progesterone receptor antagonists [anti-progestins (APs)], including the founding members of the class mifepristone (RU-486; Roussel UCLAF, Romainville, France), onapristone (ZK 98 299; Schering AG), ZK 137 316 and ZK-230 211 as well as CDB-4453 and CDB-4124 (Progenta, BIOQUAL Inc), are compounds that bind to the progesterone receptor (PR) and prevent progesterone-induced gene expression {Spitz, I. M. (2003). Steroids 68, 981-993.}. Acting on the estrogen primed endometrium, progesterone plays an essential role in the differentiation and ductal morphogenesis of endometrial tissue, but also participates in the inhibition of myometrial contractility and the polarisation of leukocyte Th1/Th2 responses that are critical for embryo implantation and the maintenance of pregnancy. A number of studies have investigated the potential beneficial effects of anti-progestins on the signs and symptoms of endometriosis {Grow, D. R., et al. (1996). Journal of Clinical Endocrinology & Metabolism 81, 1933-1939.; Kettel, L. M., et al. (1996). Fertility & Sterility 65, 23-28.; Kettel, L. M., et al. (1998). American Journal of Obstetrics & Gynaecology 178, 1151-1156.} and uterine fibroids {Eisinger, S. H., et al. (2003). Obstetrics & Gynaecology 101, 243-250.; Murphy, A. A., and Castellano, P. Z. (1994). Current Opinion in Obstetrics & Gynaecology 6, 269-278.; Murphy, A. A., et al. (1995). Fertility & Sterility 63, 761-766.; Steinauer, J., Pritts, et al. (2004). Obstetrics & Gynaecology 103, 1331-1336.; Yang, Y., et al. (1996). Chinese. Chung-Hua Fu Chan Ko Tsa Chih [Chinese Journal of Obstetrics & Gynaecology] 31, 624-626.}. Unlike GnRH analogues, and other conventional pharmacological approaches, anti-progestins, especially mifepristone, appear to be able to reduce lesion or fibroid volume, whilst maintaining a tonic level of ovarian oestrogen secretion. Such anti-progestins induce amenorrhoea and endometrial compaction, and also appear to sufficiently protect against rapid oestrogen-dependent bone loss {Grow, D. R., et al. (1996). Journal of Clinical Endocrinology & Metabolism 81, 1933-1939.}. In contrast GnRH analogues cause a rapid loss in bone mineral density, a clinical feature which limits their treatment duration to 6 months. Whilst mifepristone is a potent anti-progestin, it also has equipotent anti-glucocorticoid activity. Outside of a palliative treatment of hypercortisolism for Cushing's syndrome {Chu, J. W., et al. (2001). J Clin Endocrinol Metab 86, 3568-3573.; Sartor, O., and Cutler, G. B., Jr. (1996). Clin Obstet Gynaecol 39, 506-510.; Spitz, I. M. (2003). Steroids 68, 981-993.; Van Look, P. F., and von Hertzen, H. (1995). Human Reproduction Update 1: 19-34.}, the anti-glucocorticoid activity is an undesirable feature of mifepristone and potentially many of the steroidal classes of anti-progestins.

A further class of steroidal and non-steroidal compounds, termed the progesterone receptor modulators (PRMs, or mesoprogestins), including asoprisnil (J867, benzaldehyde, 4-[(11β,17β)-17-methoxy-17-(methoxymethyl)-3-oxoestra-4,9-dien-11-yl]-, 1-oxime; Jenpharm, TAP), J912, J956, J1042, have also been described. In addition to their potential utility in hormone replacement and as contraceptives, these classes of compounds could be considered to have utility in the treatment of endometriosis and uterine leiomyoma {Chwalisz, K., et al. (2004). Semin Reprod Med 22, 113-119.; Chwalisz, K., et al. (2002). Annals of the New York Academy of Sciences 955, 373-388; discussion 389-393.; DeManno, D., et al. (2003). Steroids 68, 1019-1032.}. Asoprisnil and structurally-related PRMs differ from anti-progestins and progestins in animal models, demonstrating partial progestogenic activity in the rabbit endometrium (McPhail's test {McPhail, M. K. (1934). Journal of physiology 83, 145-156.}) and guinea pig vagina, for instance. Preclinical studies with asoprisinil in primates have indicated that PRMs suppress endometrial growth and, unlike the effects of progestins, endometrial ER and PR expression is not repressed {Chwalisz, K., et al. (2000). Steroids 65, 741-751.; DeManno, D., et al. (2003). Steroids 68, 1019-1032.; Elger, W., et al. (2000). Steroids 65, 713-723.}.

The compounds of the present invention have been found to have useful pharmaceutical properties. They may be used to treat endometriosis, uterine fibroids (leiomyomata) and menorrhagia, adenomyosis, primary and secondary dysmenorrhoea (including symptoms of dyspareunia, dyschexia and chronic pelvic pain), chronic pelvic pain syndrome, precocious puberty, cervical ripening, contraception (emergency), breast carcinoma, ovarian carcinoma, endometrial carcinoma, prostate carcinoma, pulmonary carcinoma, testicular carcinoma, gastric carcinoma, meningioma, anxiety, premenstrual syndrome, premenstrual dysphoric disorder, alcohol abuse and reward, or Charcot-Marie-Tooth disease.

Particularly of interest are the following diseases or disorders: endometriosis, uterine fibroids (leiomyomata), menorrhagia, adenomyosis, primary and secondary dysmenorrhoea (including symptoms of dyspareunia, dyschexia and chronic pelvic pain), and chronic pelvic pain syndrome.

In particular, the compounds and derivatives of the present invention exhibit activity as progesterone receptor antagonists and may be useful for treatment where progesterone receptor antagonism is indicated.

More particularly, the compounds and derivatives of the present invention may be useful for treating endometriosis and/or uterine fibroids (leiomyomata).

International Patent Application WO 2002/085860 describes pyrazole derivatives of the formula:

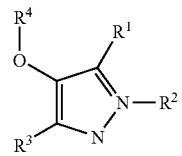

wherein $R^1$, $R^2$, $R^3$ and $R^4$ are as defined therein, which are modulators of HIV reverse transcriptase.

According to the present invention there is provided a compound of the formula (I),

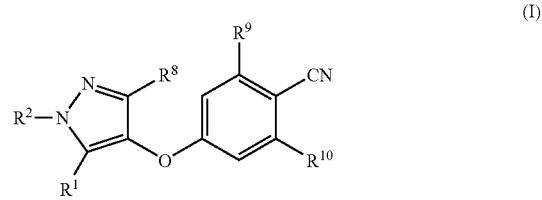

or a pharmaceutically acceptable derivative thereof, wherein:
$R^1$ represents H, $C_{1-6}$alkyl, $C_{1-6}$alkyloxy, $C_{3-8}$cycloalkyl, or halo;
$R^2$ represents H, $C_{1-6}$alkyl (optionally substituted by $R^3$), phenyl (optionally substituted by CN), or Het;
  $R^3$ represents OH, CN, Het, —$R^4$—$C_{1-6}$alkyl, or CONR$^5$R$^6$;
  $R^4$ represents —$CO_2$—, or —O—;
  $R^5$ and $R^6$ independently represent H, $C_{1-6}$alkyl (optionally substituted by OR$^7$) or $C_{3-8}$cycloalkyl;
  $R^7$ represents H or $C_{1-6}$alkyl;
  Het represents a five or six membered aromatic heterocyclic group containing (i) from one to four nitrogen heteroatom(s) or (ii) one or two nitrogen heteroatom(s) and one oxygen or one sulphur heteroatom or (iii) one or two oxygen or sulphur heteroatom(s), said heterocyclic group being optionally substituted by one or more groups selected from CN and $C_{1-6}$alkyl;
$R^8$ represents $C_{1-6}$alkyl, $C_{1-6}$alkyloxy, $C_{3-8}$cycloalkyl, or halo;
$R^9$ and $R^{10}$ independently represent H, $C_{1-6}$alkyl, $C_{1-6}$alkyloxy, CN, $CF_3$ or halo.

In the above definitions alkyl groups containing the requisite number of carbon atoms, except where indicated, can be unbranched or branched chain. Examples include methyl, ethyl, n-propyl, i-propyl, n-butyl, i-butyl, sec-butyl and t-butyl. Examples of alkyloxy include methoxy, ethoxy, n-propyloxy, i-propyloxy, n-butyloxy, i-butyloxy, sec-butyloxy and t-butyloxy. Examples of cycloalkyl include cyclopropyl, cyclobutyl, cyclopentyl, cyclohexyl and cycloheptyl. The term halogen means fluoro, chloro, bromo or iodo.

Heterocycles included within the definition of "heterocycle" are pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl and quinoxalinyl, together with partially or fully saturated versions thereof as well as azetidinyl, pyrrolidinyl, piperidinyl, piperazinyl, homopiperazinyl, oxazepanyl, and morpholinyl.

Preferably $R^1$ represents $C_{3-8}$cycloalkyl, and more preferably it represents cyclopropyl. Preferably $R^2$ represents $C_{1-6}$alkyl, more preferably it represents $C_{1-6}$alkyl substituted with $R^3$. Preferably $R^3$ represents $CONR^5R^6$. Preferably $R^4$ represents O. Preferably $R^5$ represents H. Preferably $R^6$ represents $C_{1-6}$alkyl, more preferably it represents methyl. Preferably $R^8$ represents $C_{3-8}$cycloalkyl, more preferably it represents cyclopropyl. Preferably $R^9$ represents H or halo, more preferably it represents H. Preferably $R^{10}$ represents H or halo, more preferably it represents H.

The above described embodiments of the invention may be combined with one or more further embodiments such that further embodiments are provided wherein two or more variables are defined more specifically in combination. For example, within the scope of the invention is a further embodiment wherein the variables $R^1$, $R^2$, $R^3$, $R^4$, $R^5$, $R^6$, $R^8$, $R^9$, and $R^{10}$ all have the more limited definitions assigned to them in the more specific embodiments described above. All such combinations of the more specific embodiments described and defined above are within the scope of the invention Preferred compounds according to the present invention are:
4-[(3,5-Dimethyl-1H-pyrazol-4-yl)oxy]benzonitrile;
4-(5-Cyclopropyl-3-methyl-1H-pyrazol-4-yloxy)-2,6-dimethyl-benzonitrile;
4-(5-cyclopropyl-3-methyl-1H-pyrazol-4-yloxy)-2-methylbenzonitrile;
4-[(3,5-Dicyclopropyl-1H-pyrazol-4-yl)oxy]-2,6-dimethylbenzonitrile;
4-(3,5-Diethyl-1H-pyrazol-4-yloxy)-benzonitrile;
4-(3,5-Dimethyl-1H-pyrazol-4-yloxy)-2,6-dimethyl-benzonitrile;
4-(3,5-Dicyclopropyl-1H-pyrazol-4-yloxy)-benzonitrile;
4-(3,5-Diethyl-1H-pyrazol-4-yloxy)-2,6-dimethyl-benzonitrile;
4-(3,5-Diethyl-1H-pyrazol-4-yloxy)-2-methoxy-benzonitrile;
4-(3-Cyclopropyl-5-methyl-1H-pyrazol-4-yloxy)-benzonitrile;
4-(3,5-Diethyl-1H-pyrazol-4-yloxy)-phthalonitrile;
4-(3,5-Diethyl-1H-pyrazol-4-yloxy)-2-trifluoromethyl-benzonitrile;
4-(3,5-Dicyclopropyl-1H-pyrazol-4-yloxy)-2-methyl-benzonitrile;
2-Chloro-4-(3,5-dicyclopropyl-1H-pyrazol-4-yloxy)-benzonitrile;
4-[(5-Ethyl-3-methoxy-1H-pyrazol-4-yl)oxy]benzonitrile;
4-[(3-Cyclopropyl-1H-pyrazol-4-yl)oxy]-2,6-dimethylbenzonitrile;
4-{[1-(2-Hydroxyethyl)-3,5-dimethyl-1H-pyrazol-4-yl]oxy}benzonitrile;
2-Fluoro-4-[1-(2-hydroxy-ethyl)-3,5-dimethyl-1H-pyrazol-4-yloxy]-benzonitrile;
2-Chloro-4-[1-(2-hydroxy-ethyl)-3,5-dimethyl-1H-pyrazol-4-yloxy]-benzonitrile;
4-[1-(2-Hydroxy-ethyl)-3,5-dimethyl-1H-pyrazol-4-yloxy]-phthalonitrile;
4-[3,5-Diethyl-1-(2-hydroxy-ethyl)-1H-pyrazol-4-yloxy]-benzonitrile;
4-[3,5-Diethyl-1-(2-hydroxy-ethyl)-1H-pyrazol-4-yloxy]-2-fluoro-benzonitrile;
2-Chloro-4-[1-(2-hydroxy-ethyl)-3,5-diethyl-1H-pyrazol-4-yloxy]-benzonitrile;
4-[3,5-Diethyl-1-(2-hydroxy-ethyl)-1H-pyrazol-4-yloxy]-2-methyl-benzonitrile;
4-[3,5-Diethyl-1'-(2-hydroxy-ethyl)-1H-pyrazol-4-yloxy]-phthalonitrile;
4-[3,5-Diethyl-1-(2-hydroxy-ethyl)-1H-pyrazol-4-yloxy]-2-methoxy-benzonitrile;
4-[3,5-Diethyl-1-(2-hydroxy-ethyl)-1H-pyrazol-4-yloxy]-2,6-dimethyl-benzonitrile;
4-{[3,5-Dicyclopropyl-1-(2-hydroxyethyl)-1H-pyrazol-4-yl]oxy}-2,6-dimethylbenzonitrile;
4-{[3-Cyclopropyl-1-(2-hydroxyethyl)-5-methyl-1H-pyrazol-4-yl]oxy}-2,6-dimethylbenzonitrile;
4-{[5-cyclopropyl-1-(2-hydroxyethyl)-3-methyl-1H-pyrazol-4-yl]oxy}-2,6-dimethylbenzonitrile;
4-{[3,5-Diethyl-1-(2-methoxyethyl)-1H-pyrazol-4-yl]oxy}-2,6-dimethylbenzonitrile;
Ethyl[4-(4-cyanophenoxy)-3,5-diethyl-1H-pyrazol-1-yl]acetate;
Ethyl[4-(4-cyano-3,5-dimethylphenoxy)-3,5-dicyclopropyl-1H-pyrazol-1-yl]acetate;
Ethyl[4-(4-cyano-3,5-dimethyl-phenoxy)-3,5-dimethyl-pyrazol-1-yl]acetate;
Ethyl[4-(4-cyanophenoxy)-3,5-dicyclopropyl-pyrazol-1-yl]acetate;
Ethyl[4-(4-cyano-3,5-dimethyl-phenoxy)-3,5-diethyl-pyrazol-1-yl]acetate;
Ethyl[4-(4-cyano-3-trifluoromethyl-phenoxy)-3,5-dicyclopropyl-pyrazol-1-yl]acetate;
Ethyl[4-(4-cyano-3-methyl-phenoxy)-3,5-dicyclopropyl-pyrazol-1-yl]acetate;
Ethyl[4-(4-cyano-3,5-dimethyl-phenoxy)-3-cyclopropyl-pyrazol-1-yl]acetate;
Ethyl[4-(3-chloro-4-cyano-phenoxy)-3,5-dicyclopropyl-pyrazol-1-yl]acetate;
Ethyl[4-(4-cyanophenoxy)-3-cyclopropyl-5-methyl-pyrazol-1-yl]acetate;
Ethyl[4-(4-cyanophenoxy)-5-cyclopropyl-3-methyl-pyrazol-1-yl]acetate;
Ethyl[4-(4-cyano-3-methyl-phenoxy)-3-cyclopropyl-5-methyl-pyrazol-1-yl]acetate;
Ethyl[4-(4-cyano-3-methyl-phenoxy)-5-cyclopropyl-3-methyl-pyrazol-1-yl]acetate;
Ethyl[4-(4-cyano-3,5-dimethylphenoxy)-3-cyclopropyl-5-methyl-1H-pyrazol-1-yl]acetate;
Ethyl[4-(4-cyano-3,5-dimethylphenoxy)-5-cyclopropyl-3-methyl-1H-pyrazol-1-yl]acetate;
Ethyl 2-[4-(4-cyanophenoxy)-3,5-diethyl-1H-pyrazol-1-yl]-2-methylpropanoate;
Methyl 2-[4-(4-cyanophenoxy)-3,5-diethyl-1H-pyrazol-1-yl]-2-methylpropanoate;
2-[4-(4-Cyano-3,5-dimethylphenoxy)-3,5-dicyclopropyl-1H-pyrazol-1-yl]-N-methyl-acetamide;
2-[4-(4-Cyanophenoxy)-3,5-diethyl-1H-pyrazol-1-yl]-N-methyl-acetamide;

2-[4-(4-Cyanophenoxy)-3,5-diethyl-1H-pyrazol-1-yl]-acetamide;
2-[4-(4-Cyanophenoxy)-3,5-diethyl-1H-pyrazol-1-yl]-N-(hydroxyethyl)-acetamide;
2-[4-(4-Cyanophenoxy)-3,5-diethyl-1H-pyrazol-1-yl]-N-(methoxyethyl)-acetamide;
2-[4-(4-Cyanophenoxy)-3,5-diethyl-1H-pyrazol-1-yl]-N,N-dimethyl-acetamide;
2-[4-(4-Cyanophenoxy)-3,5-diethyl-1H-pyrazol-1-yl]-N-ethyl-acetamide;
2-[4-(4-Cyanophenoxy)-3,5-diethyl-1H-pyrazol-1-yl]-N-cyclopropyl-acetamide;
2-[4-(4-Cyanophenoxy)-3,5-diethyl-1H-pyrazol-1-yl]-N-isopropyl-acetamide;
2-[4-(4-Cyano-3,5-dimethyl-phenoxy)-3,5-dicyclopropyl-1H-pyrazol-1-yl]-acetamide;
2-[4-(4-Cyano-3,5-dimethyl-phenoxy)-3,5-dimethyl-1H-pyrazol-1-yl]-N-methyl-acetamide;
2-[4-(4-Cyano-3,5-dimethyl-phenoxy)-3,5-dimethyl-1H-pyrazol-1-yl]-acetamide;
2-[4-(4-Cyanophenoxy)-3,5-dicyclopropyl-1H-pyrazol-1-yl]-acetamide;
2-[4-(4-Cyanophenoxy)-3,5-dicyclopropyl-1H-pyrazol-1-yl]-N-methyl-acetamide;
2-[4-(4-Cyano-3,5-dimethyl-phenoxy)-3,5-diethyl-1H-pyrazol-1-yl]-N-methyl-acetamide;
2-[4-(4-Cyano-3,5-dimethyl-phenoxy)-3,5-diethyl-1H-pyrazol-1-yl]-acetamide;
2-[4-(4-Cyano-3-trifluoromethyl-phenoxy)-3,5-dicyclopropyl-1H-pyrazol-1-yl]-N-methyl-acetamide;
2-[4-(4-Cyano-3-methyl-phenoxy)-3,5-dicyclopropyl-1H-pyrazol-1-yl]-N-methyl-acetamide;
2-[4-(4-Cyano-3,5-dimethyl-phenoxy)-5-cyclopropyl-3-methyl-1H-pyrazol-1-yl]-N-methyl-acetamide;
2-[4-(4-Cyano-3,5-dimethyl-phenoxy)-3-cyclopropyl-5-methyl-1H-pyrazol-1-yl]-N-methyl-acetamide;
2-[4-(4-Cyano-3,5-dimethyl-phenoxy)-3-cyclopropyl-5-methyl-1H-pyrazol-1-yl]-acetamide;
2-[4-(4-Cyano-3,5-dimethyl-phenoxy)-5-cyclopropyl-3-methyl-1H-pyrazol-1-yl]-acetamide;
2-[4-(4-Cyano-dimethyl-phenoxy)-3-cyclopropyl-1H-pyrazol-1-yl]-N-methyl-acetamide;
2-[4-(4-Cyanophenoxy)-5-cyclopropyl-3-methyl-1H-pyrazol-1-yl]-N-methyl-acetamide;
2-[4-(4-Cyanophenoxy)-3-cyclopropyl-5-methyl-1H-pyrazol-1-yl]-N-methyl-acetamide;
2-[4-(4-Cyano-3-methyl-phenoxy)-3-cyclopropyl-5-methyl-1H-pyrazol-1-yl]-N-methyl-acetamide;
2-[4-(4-Cyano-3-methyl-phenoxy)-5-cyclopropyl-3-methyl-1H-pyrazol-1-yl]-N-methyl-acetamide;
2-[4-(3-Chloro-4-cyanophenoxy)-3,5-dicyclopropyl-1H-pyrazol-1-yl]-N-methyl-acetamide;
2-[4-(4-Cyanophenoxy)-5-ethyl-3-methoxy-1H-pyrazol-1-yl]-acetamide;
2-[4-(4-Cyano-3,5-dimethyl-phenoxy)-3-cyclopropyl-pyrazol-1-yl]-2-methyl-propanamide;
2-[4-(4-Cyanophenoxy)-3,5-diethyl-pyrazol-1-yl]-2-methyl-N-methyl-propanamide;
2-[4-(4-Cyano-3,5-dimethyl-phenoxy)-5-chloro-3-cyclopropyl-1H-pyrazol-1-yl]-N-methyl-acetamide;
2-[4-(4-Cyano-3,5-dimethyl-phenoxy)-3-chloro-5-cyclopropyl-1H-pyrazol-1-yl]-N-methyl-acetamide;
4-{[1-(Cyanomethyl)-3,5-dimethyl-1H-pyrazol-4-yl]oxy}-2,6-dimethylbenzonitrile;
4-{[1-(Cyanomethyl)-1H-pyrazol-4-yl]oxy}-2,6-dimethylbenzonitrile;
4-{[1-(Cyanomethyl)-3,5-diethyl-1H-pyrazol-4-yl]oxy}benzonitrile;
4-{[1-(Cyanomethyl)-3,5-diethyl-1H-pyrazol-4-yl]oxy}-2,6-dimethylbenzonitrile;
4-{[1-(Cyanomethyl)-5-ethyl-3-methoxy-1H-pyrazol-4-yl]oxy}benzonitrile;
4-{[1-(1-Cyano-1-methylethyl)-3-cyclopropyl-1H-pyrazol-4-yl]oxy}-2,6-dimethylbenzonitrile;
4-{1-(1-Cyano-1-methylethyl)-3,5-dimethyl-1H-pyrazol-4-yl]oxy}-2,6-dimethyl-benzonitrile;
4-{1-(1-Cyano-1-methylethyl)-3,5-ethyl-1H-pyrazol-4-yl]oxy}-benzonitrile;
4-{1-(1-Cyano-ethyl)-3,5-ethyl-1H-pyrazol-4-yl]oxy}-benzonitrile;
4-({3-Cyclopropyl-5-methyl-1-[(5-methylisoxazol-3-yl)methyl]-1H-pyrazol-4-yl}oxy)-2,6-dimethyl benzonitrile;
4-({5-Cyclopropyl-3-methyl-1-[(5-methylisoxazol-3-yl)methyl]-1H-pyrazol-4-yl}oxy)-2,6-dimethyl benzonitrile;
4-({5-Cyclopropyl-3-methyl-1-[(isoxazol-3-yl)methyl]-1H-pyrazol-4-yl}oxy)-2,6-dimethylbenzonitrile;
4-({3-Cyclopropyl-5-methyl-1-[(isoxazol-3-yl)methyl]-1H-pyrazol-4-yl}oxy)-2,6-dimethylbenzonitrile;
4-({5-Cyclopropyl-3-methyl-1-[(isoxazol-3-yl)methyl]-1H-pyrazol-4-yl}oxy)-benzonitrile;
4-({3-Cyclopropyl-5-methyl-1-[(isoxazol-3-yl)methyl]-1H-pyrazol-4-yl}oxy)-benzonitrile;
4-{[5-Ethyl-1-(1H-imidazol-2-ylmethyl)-3-methyl-1H-pyrazol-4-yl]oxy}-benzonitrile;
4-({3,5-Dicyclopropyl-1-[(pyrimidin-5-yl)methyl]-1H-pyrazol-4-yl}oxy)-2,6-dimethylbenzonitrile;
4-({3,5-Diethyl-1-[(isoxazol-3-yl)methyl]-1H-pyrazol-4-yl}oxy)-benzonitrile;
4-({3,5-Diethyl-1-[(5-methylisoxazol-3-yl)methyl]-1H-pyrazol-4-yl}oxy)-benzonitrile;
4-({3,5-Diethyl-1-[(3,5-dimethylisoxazol-4-yl)methyl]-1H-pyrazol-4-yl}oxy)-benzonitrile;
4-({3,5-Diethyl-1-[(pyridin-2-yl)methyl]-1H-pyrazol-4-yl}oxy)-benzonitrile;
4-({3,5-Diethyl-1-[(1-methylimidazol-2-yl)methyl]-1H-pyrazol-4-yl}oxy)-benzonitrile;
4-({3,5-Diethyl-1-[(thiazol-5-yl)methyl]-1H-pyrazol-4-yl}oxy)-benzonitrile;
4-({3,5-Diethyl-1-[(pyridin-4-yl)methyl]-1H-pyrazol-4-yl}oxy)-benzonitrile;
4-({3,5-Diethyl-1-[(pyridin-3-yl)methyl]-1H-pyrazol-4-yl}oxy)-benzonitrile;
4-({3,5-Diethyl-1-[(pyrimidin-5-yl)methyl]-1H-pyrazol-4-yl}oxy)-benzonitrile;
4-({3,5-Dicyclopropyl-1-[(isoxazol-3-yl)methyl]-1H-pyrazol-4-yl}oxy)-benzonitrile;
4-{[3-Cyclopropyl-5-methyl-1-(4H-1,2,4-triazol-3-ylmethyl)-1H-pyrazol-4-yl]oxy}-2,6-dimethylbenzonitrile;
4-{[3,5-Diethyl-1-(4H-1,2,4-triazol-3-ylmethyl)-1H-pyrazol-4-yl]oxy}benzonitrile;
4-({3,5-Diethyl-1-[(5-methyl-4H-1,2,4-triazol-3-yl)methyl]-1H-pyrazol-4-yl}oxy)benzonitrile;
4-({3,5-Diethyl-1-[(5-methyl-1,3,4-oxadiazol-2-yl)methyl]-1H-pyrazol-4-yl}oxy)benzonitrile;
4-({3,5-Diethyl-1-[(5-methyl-1,3,4-thiadiazol-2-yl)methyl]-1H-pyrazol-4-yl}oxy)benzonitrile;
4-{[3,5-Diethyl-1-(1,3,4-thiadiazol-2-ylmethyl)-1H-pyrazol-4-yl]oxy}benzonitrile;
4-{[3,5-Dicyclopropyl-1-(1H-pyrazol-3-ylmethyl)-1H-pyrazol-4-yl]oxy}benzonitrile;
4-{[3-Cyclopropyl-5-methyl-1-(1H-1,2,3-triazol-5-ylmethyl)-1H-pyrazol-4-yl]oxy}-2,6-dimethylbenzonitrile;

4-[(3,5-Diethyl-1-methyl-1H-pyrazol-4-yl)oxy]benzonitrile;
4-[(3,5-Diethyl-1-propyl-1H-pyrazol-4-yl)oxy]benzonitrile;
4-[(3,5-Diethyl-1-ethyl-1H-pyrazol-4-yl)oxy]benzonitrile;
4-[(3,5-Diethyl-1-phenyl-1H-pyrazol-4-yl)oxy]benzonitrile;
4-[4-(4-Cyanophenoxy)-3,5-diethyl-1H-pyrazol-1-yl]benzonitrile;
4-[(3,5-Dicyclopropyl-1-pyridin-3-yl-1H-pyrazol-4-yl)oxy]-2,6-dimethylbenzonitrile;
4-[(3,5-Dicyclopropyl-1-pyrimidin-5-yl-1H-pyrazol-4-yl)oxy]-2,6-dimethylbenzonitrile;
4-[(3,5-Diethyl-1'H-1,4'-bipyrazol-4-yl)oxy]benzonitrile;

and the pharmaceutically acceptable salts and solvates thereof.

Particularly preferred compounds according to the present invention include:
4-{[3,5-Dicyclopropyl-1-(2-hydroxyethyl)-1H-pyrazol-4-yl]oxy}-2,6-dimethylbenzonitrile;
2-[4-(4-Cyano-3,5-dimethylphenoxy)-3,5-dicyclopropyl-1H-pyrazol-1-yl]-N-methylacetamide;
2-[4-(4-Cyano-3,5-dimethyl-phenoxy)-3,5-dicyclopropyl-1H-pyrazol-1-yl]-acetamide;
2-[4-(4-Cyanophenoxy)-3,5-dicyclopropyl-1H-pyrazol-1-yl]-N-methyl-acetamide;
2-[4-(4-Cyano-3-methyl-phenoxy)-3,5-dicyclopropyl-1H-pyrazol-1-yl]-N-methyl-acetamide;
2-[4-(3-Chloro-4-cyanophenoxy)-3,5-dicyclopropyl-1H-pyrazol-1-yl]-N-methyl-acetamide;
4-{[1-(Cyanomethyl)-3,5-diethyl-1H-pyrazol-4-yl]oxy}benzonitrile;
4-{[1-(Cyanomethyl)-3,5-diethyl-1H-pyrazol-4-yl]oxy}-2,6-dimethylbenzonitrile;
4-({3,5-Dicyclopropyl-1-[(pyrimidin-5-yl)methyl]-1H-pyrazol-4-yl}oxy)-2,6-dimethylbenzonitrile;
4-({3,5-Diethyl-1-[(isoxazol-3-yl)methyl]-1H-pyrazol-4-yl}oxy)-benzonitrile;

and the pharmaceutically acceptable salts and solvates thereof.

Pharmaceutically acceptable derivatives of the compounds of formula (I) according to the invention include salts, solvates, complexes, polymorphs and crystal habits thereof, prodrugs, stereoisomers, geometric isomers, tautomeric forms, and isotopic variations of compounds of formula (I). Preferably, pharmaceutically acceptable derivatives of compounds of formula (I) comprise salts, solvates, esters and amides of the compounds of formula (I). More preferably, pharmaceutically acceptable derivatives of compounds of formula (I) are salts and solvates.

The pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see "Handbook of Pharmaceutical Salts: Properties, Selection, and Use" by Stahl and Wermuth (Wiley-VCH, 2002).

Pharmaceutically acceptable salts of compounds of formula I may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see "Polymorphism in Pharmaceutical Solids" by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes)

and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshome and A. Stuart, 4$^{th}$ Edition (Edward Arnold, 1970).

Hereinafter all references to compounds of formula (I) include references to salts, solvates, multi-component complexes and liquid crystals thereof and to solvates, multi-component complexes and liquid crystals of salts thereof.

As indicated above, so-called 'prodrugs' of the compounds of formula (I) are also within the scope of the invention. Thus certain derivatives of compounds of formula (I), which may have little or no pharmacological activity themselves, can be converted into compounds of formula I having the desired activity, for example by hydrolytic cleavage, when administered into, or onto, the body. Such derivatives are referred to as 'prodrugs'. Further information on the use of prodrugs may be found in "Pro-drugs as Novel Delivery Systems", Vol. 14, ACS Symposium Series (T. Higuchi and W. Stella) and "Bioreversible Carriers in Drug Design", Pergamon Press, 1987 (Ed. E. B. Roche, American Pharmaceutical Association).

Prodrugs in accordance with the invention can be produced by replacing appropriate functionalities present in the compounds of formula (I) with certain moieties known to those skilled in the art as 'pro-moieties' as described, for example, in "Design of Prodrugs" by H. Bundgaard (Elsevier, 1985).

Some examples of prodrugs in accordance with the invention include
(i) where the compound of formula (I) contains an alcohol functionality (—OH), an ether thereof, for example, a compound wherein the hydrogen of the alcohol functionality of the compound of formula (I) is replaced by $(C_1$-$C_6)$alkanoyloxymethyl; and
(ii) where the compound of formula (I) contains a primary or secondary amino functionality (—NH$_2$ or —NHR where R≠H), an amide thereof, for example, a compound wherein, as the case may be, one or both hydrogens of the amino functionality of the compound of formula (I) is/are replaced by $(C_1$-$C_{10})$alkanoyl.

Further examples of replacement groups in accordance with the foregoing examples and examples of other prodrug types may be found in the aforementioned references.

Moreover, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism. Included within the scope of the present invention are all stereoisomers, geometric isomers and tautomeric forms of the compounds of formula I, including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (I) should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The compounds of the invention may be administered alone or in combination with one or more other compounds of the invention or in combination with one or more other drugs (or as any combination thereof).

The compounds of the present invention may be administered in combination with COX inhibitors. Thus in a further aspect of the invention, there is provided a pharmaceutical product containing a progesterone receptor antagonist and one or more COX inhibitors as a combined preparation for simultaneous, separate or sequential use in the treatment of endometriosis. COX inhibitors useful for combining with the compounds of the present invention include, but are not limited to:

(i) ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenec, alclofenac, ibufenac, isoxepac, furofenac, tiopinac, zidometacin, acetyl salicylic acid, indometacin, piroxicam, tenoxicam, nabumetone, ketorolac, azapropazone, mefenamic acid, tolfenamic acid, diflunisal, podophyllotoxin derivatives, acemetacin, droxicam, floctafenine, oxyphenbutazone, phenylbutazone, proglumetacin, acemetacin, fentiazac, clidanac, oxipinac, mefenamic acid, meclofenamic acid, flufenamic acid, niflumic acid, flufenisal, sudoxicam, etodolac, piprofen, salicylic acid, choline magnesium trisalicylate, salicylate, benorylate, fentiazac, clopinac, feprazone, isoxicam and 2-fluoro-a-methyl[1,1'-biphenyl]-4-acetic acid, 4-(nitrooxy)butyl ester (See Wenk, et al., *Europ. J. Pharmacol.* 453:319-324 (2002));

(ii) meloxicam, (CAS registry number 71125-38-7; described in U.S. Pat. No. 4,233,299), or a pharmaceutically acceptable salt or prodrug thereof;

(iii) celecoxib (U.S. Pat. No. 5,466,823), valdecoxib (U.S. Pat. No. 5,633,272), deracoxib (U.S. Pat. No. 5,521,207), rofecoxib (U.S. Pat. No. 5,474,995), etoricoxib (International Patent Application Publication No. WO 98/03484), JTE-522 (Japanese Patent Application Publication No. 9052882), or a pharmaceutically acceptable salt or prodrug thereof;

(iv) Parecoxib (described in U.S. Pat. No. 5,932,598), which is a therapeutically effective prodrug of the tricyclic Cox-2 selective inhibitor valdecoxib (described in U.S. Pat. No. 5,633,272), in particular sodium parecoxib;

(v) ABT-963 (described in International Patent Application Publication No. WO 00/24719)

(vi) Nimesulide (described in U.S. Pat. No. 3,840,597), flosulide (discussed in J. Carter, *Exp. Opin. Ther. Patents.* 8(1), 21-29 (1997)), NS-398 (disclosed in U.S. Pat. No. 4,885,367), SD 8381 (described in U.S. Pat. No. 6,034,256), BMS-347070 (described in U.S. Pat. No. 6,180,651), S-2474 (described in European Patent Publication No. 595546) and MK-966 (described in U.S. Pat. No. 5,968,974);

(vii) darbufelone (Pfizer), CS-502 (Sankyo), LAS 34475 (Almirall Profesfarma), LAS 34555 (Almirall Profesfarma), S-33516 (Servier), SD 8381 (Pharmacia, described in U.S. Pat. No. 6,034,256), BMS-347070 (Bristol Myers Squibb, described in U.S. Pat. No. 6,180,651), MK-966 (Merck), L-783003 (Merck), T-614 (Toyama), D-1367 (Chiroscience), L-748731 (Merck), CT3 (Atlantic Pharmaceutical), CGP-28238 (Novartis), BF-389 (Biofor/Scherer), GR-253035 (Glaxo Wellcome), 6-dioxo-9H-purin-8-yl-cinnamic acid (Glaxo Wellcome), and S-2474 (Shionogi).

The compounds of the present invention may be administered in combination with PDE5 inhibitors. Thus in a further aspect of the invention, there is provided a pharmaceutical product containing a progesterone receptor antagonist and one or more PDEV inhibitors as a combined preparation for simultaneous, separate or sequential use in the treatment of endometriosis.

PDEV inhibitors useful for combining with compounds of the present invention include, but are not limited to:

(i) Preferably 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil, e.g. as sold as Viagra®) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756);5-(2-ethoxy-5-morpholinoacetylphenyl)-1-methyl-3-n-propyl-1,6-dihydro-7H-pyrazolo[4,3-d]pyrimidin-7-one (see EP-A-0526004); 3-ethyl-5-[5-(4-ethylpiperazin-1-ylsulphonyl)-2-n-propoxy phenyl]-2-(pyridin-2-yl)methyl-2,6-dihydro-7H-pyrazolo[4,3-d]pyrmidin-7-one (see WO 98/49166); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333); (+)-3-ethyl-5-[5-(4-ethylpiperazin-1-ylsulphonyl)-2-(2-methoxy-1 (R)-methylethoxy) pyridin-3-yl]-2-methyl-2,6-dihydro-7H-pyrazolo[4,3-d]pyrimidin-7-one, also known as 3-ethyl-5-{5-[4- ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8); 5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15); 5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66); 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124); 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132); (6R, 12aR)-2,3,6,7,12,12a-hexahydro-2-methyl-6-(3,4-methylenedioxyphenyl) pyrazino[2',1': 6,1]pyrido[3,4-b]indole-1,4-dione (tadalafil, IC-351, Cialis®), i.e. the compound of examples 78 and 95 of published international application WO95/19978, as well as the compound of examples 1, 3, 7 and 8; 2-[2-ethoxy-5-(4-ethylpiperazin-1-yl-1-sulphonyl)-phenyl]-5-methyl-7-propyl-3H-imidazo[5,1-f][1,2,4]triazin-4-one (vardenafil, LEVITRA®) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; the compound of example 11 of published international application WO93/07124 (EISAI); compounds 3 and 14 from Rotella D P, *J. Med. Chem.*, 2000, 43, 1257; 4-(4-chlorobenzyl)amino-6,7,8-trimethoxyquinazoline; N-[[3-(4,7-dihydro-1-methyl-7-oxo-3-propyl-1H-pyrazolo[4,3-d]-pyrimidin-5-yl)-4-propxyphenyl]sulfonyl]-1-methyl-2-pyrrolidine propanamide ["DA-8159" (Example 68 of WO00/27848)]; and 7,8-dihydro-8-oxo-6-[2-propoxyphenyl]-1H-imidazo[4,5g]quinazoline and 1-[3-[1-[(4-fluorophenyl)methyl]-7,8-dihydro-8-oxo-1H-imidazo[4,5-g]quinazolin-6-yl]-4-propoxyphenyl] carboxamide; 4-[(3-chloro-4-methoxybenzyl)amino]-2-[(2S)-2-(hydroxymethyl)pyrrolidin-1-yl]-N-(pyrimidin-2-ylmethyl) pyrimidine-5-carboxamide (TA-1790); 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzene sulfonamide (DA 8159) and pharmaceutically acceptable salts thereof.

(ii) 4-bromo-5-(pyridylmethylamino)-6-[3-(4-chlorophenyl)-propoxy]-3(2H)pyridazinone; 1-[4-[(1,3-benzodioxol-5-ylmethyl)amiono]-6-chloro-2-quinozolinyl]-4-piperidine-carboxylic acid, mono-sodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8, 9,9a-octahydrocyclopent[4,5]-imidazo[2,1-b]purin-4-one; 3-acetyl-1-(2-chlorobenzyl)-2-propyl indole-6-carboxylate; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; 1-methyl-5(5-morpholinoacetyl-2-n-propoxyphenyl)-3-n-propyl-1,6-dihydro- 7H-pyrazolo(4,3-d)pyrimidin-7-one; 1-[4-[((1,3-benzodioxol-5-ylmethyl) amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer); FR229934 and FR226807 (Fujisawa); and Sch-51866.

Preferably the PDEV inhibitor is selected from sildenafil, tadalafil, vardenafil, DA-8159 and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one. Most preferably the PDE5 inhibitor is sildenafil and pharmaceutically acceptable salts thereof. Sildenafil citrate is a preferred salt.

The compounds of the present invention may be administered in combination with a V1a antagonist. Thus, in a further aspect of the invention, there is provided a pharmaceutical product containing a progesterone receptor antagonist and one or more V1a antagonists as a combined preparation for simultaneous, separate or sequential use in the treatment of endometriosis.

A suitable vasopressin V1a receptor antagonist is, for example, (4-[4-Benzyl-5-(4-methoxy-piperidin-1-ylmethyl)-4H-[1,2,4]triazol-3-yl]-3,4,5,6-tetrahydro-2H[1,2']bipyridinyl), which is Example 26 in WO 2004/37809. A further example of a suitable vasopressin V1a receptor antagonist is 8-chloro-5-Methyl-1-(3,4,5,6-tetrahydro-2H-[1,2']bipyridinyl-4-yl)-5,6-dihydro-4H-2,3,5,10b-tetraazobenzo[e]azulene, or a pharmaceutically acceptable salt or solvate thereof, which is Example 5 in WO 04/074291.

Further examples of vasopressin V1a receptor antagonists for use with the invention are: SR49049 (Relcovaptan), atosiban (Tractocile®), conivaptan (YM-087), VPA-985, CL-385004, Vasotocin and OPC21268. Additionally, the V1a receptor antagonists described in WO 01/58880 are suitable for use in the invention.

The compounds of the present invention may be administered in combination with an alpha adrenergic receptor antagonist (also known as α-adrenoceptor blocker, α-receptor blocker or α-blocker). Thus, in a further aspect of the invention, there is provided a pharmaceutical product containing a progesterone receptor antagonist and one or more alpha adrenergic receptor antagonists as a combined preparation for simultaneous, separate or sequential use in the treatment of endometriosis.

$\alpha_1$-Adrenergic receptor antagonists useful for the present invention include, but are not limited to, terazosin (U.S. Pat. No. 4,026,894), doxazosin (U.S. Pat. No. 4,188,390), prazosin (U.S. Pat. No. 3,511,836), bunazosin (U.S. Pat. No. 3,920,636), alfuzosin (U.S. Pat. No. 4,315,007), naftopidil (U.S. Pat. No. 3,997,666), tamsulosin (U.S. Pat. No. 4,703,063), silodosin (U.S. Pat. No. 5,387,603), phentolamine and phentolamine mesylate (U.S. Pat. No. 2,503,059), trazodone (U.S. Pat. No. 3,381,009), indoramin (U.S. Pat. No. 3,527,761), phenoxybenzamine (U.S. Pat. No. 2,599,000), rauwolfa alkaloids (natural product from the shrub Rauwolfia serpentine), Recordati 15/2739 (WO 93/17007), SNAP 1069 (WO 94/08040 e.g. 3, compound 9, page 77 & table 3, page 86), SNAP 5089 (WO 94/10989), RS17053 (U.S. Pat. No. 5,436,264), SL 89.0591 (EP 435749), and abanoquil (EP 100200); the compounds disclosed in International Application Publication No. WO 03/076427 in particular 5-cyclopropyl-7-methoxy-2-(2-morpholin-4-ylmethyl-7,8-dihydro[1,6]-naphthyridin-6(5H)-yl)-4(3H)-quinazolinone (example 11), and the compounds disclosed in International Application Publication No. WO 98/30560 in particular 4-amino-6,7-dimethoxy-2-(5-methanesulfonamido-1,2,3,4-tetrahydroisoquinol-2-yl)-5-(2-pyridyl)quinazoline (example 19); and pharmaceutically acceptable derivatives thereof. Preferred α-adrenergic receptor antagonists are doxazosin, 5-cyclopropyl-7-methoxy-2-(2-morpholin-4-ylmethyl-7,8-dihydro[1,6]-naphthyridin-6(5H)-yl)-4(3H)-quinazolinone and 4-Amino-6,7-dimethoxy-2-(5-methanesulfonamido-1,2,3,4-tetrahydroisoquinol-2-yl)-5-(2-pyridyl)quinazoline and pharmaceutically acceptable derivatives thereof. The mesylate salt of 4-Amino-6,7-dimethoxy-2-(5-methanesulfonamido-1,2,3,4-tetrahydroisoquinol-2-yl)-5-(2-pyridyl)quinazoline is of particular interest (see WO 01/64672).

$\alpha_2$-Adrenergic receptor antagonists suitable for the present invention include dibenamine (DE 824208), tolazoline (U.S. Pat. No. 2,161,938), trimazosin (U.S. Pat. No. 3,669,968), efaroxan (EP 71368), yohimbine (M R Goldberg et al, Pharmacol. Rev. 35, 143-180 (1987)), idazoxan (EP 33655), and clonidine (U.S. Pat. No. 3,202,660);

Non-selective α-adrenergic receptor antagonists suitable for the present invention include dapiprazole (U.S. Pat. No. 4,252,721);

The compounds of the present invention may be administered in combination with an 5-alpha reductase inhibitor. Thus, in a further aspect of the invention, there is provided a pharmaceutical product containing a progesterone receptor antagonist and one or more 5-alpha reductase inhibitors as a combined preparation for simultaneous, separate or sequential use in the treatment of endometriosis.

5-alpha reductase inhibitors include inhibitors of 5-alpha reductase isoenzyme 2. Suitable compounds for use in the present invention are PROSCAR® (also known as finasteride, U.S. Pat. Nos. 4,377,584 and 4,760,071), compounds described in WO 93/23420, EP0572166, WO 93/23050, WO 93/23038, WO 93/23048, WO 93/23041, WO 93/23040, WO 93/23039, WO 93/23376, WO 93/23419, EP0572165, and WO 93/23051.

The compounds of the present invention may be administered in combination with an agent which lowers estrogen levels, or which antagonises the estrogen receptor. Thus, in a further aspect of the invention, there is provided a pharmaceutical product containing a progesterone receptor antagonist and one or more agents which lower estrogen levels, or antagonise the estrogen receptor, as a combined preparation for simultaneous, separate or sequential use in the treatment of endometriosis.

Agents which lower estrogen levels include gonadotropin releasing hormone (GnRH) agonists, GnRH antagonists and estrogen synthesis inhibitors. Agents which antagonise the estrogen receptor, i.e. estrogen receptor antagonists, include anti-estrogens.

GnRH agonists suitable for the present invention include leuprorelin (Prostap-Wyeth), buserelin (Suprefact-Shire), goserelin (Zoladex-Astra Zeneca), triptorelin (De-capeptyl-Ipsen), narfarelin (Synarel-Searle), deslorelin (Somagard-Shire), and histrelin/supprelin (Ortho Pharmaceutical Corp/Shire).

GnRH antagonists suitable for the present invention include teverelix (also known as antarelix), abarelix (Plenaxis-Praecis Pharmaceuticals Inc.), cetrorelix (Cetrotide-ASTA Medica), and ganirelix (Orgalutran-Organon).

Anti-estrogens suitable for the present invention include tamoxifen, Faslodex (Astra Zeneca), idoxifene (see Coombes et al. (1995) Cancer Res. 55, 1070-1074), raloxifene or EM-652 (Labrie, F et al, (2001) J steroid Biochem Mol Biol, 79, 213). Estrogen synthesis inhibitors suitable for the present invention include aromatase inhibitors. Examples of aromatase inhibitors include Formestane (4-OH androstenedione), Exemestane, Anastrozole (Arimidex) and Letroxole.

The compounds of the present invention may be administered in combination with an alpha-2-delta ligand. Thus, in a further aspect of the invention, there is provided a pharmaceutical product containing a progesterone receptor antagonist and one ore more alpha-2-delta ligands, as a combined preparation for simultaneous, separate or sequential use in the treatment of endometriosis.

Examples of alpha-2-delta ligands for use in the present invention are those compounds, or pharmaceutically acceptable salts thereof, generally or specifically disclosed in U.S. Pat. No. 4,024,175, particularly gabapentin, EP641330, particularly pregabalin, U.S. Pat. No. 5,563,175, WO-A-97/33858, WO-A-97/33859, WO-A-99/31057, WO-A-99/31074, WO-A-97/29101, WO-A-02/085839, particularly [(1R,5R,6S)-6-(aminomethyl)bicyclo[3.2.0]hept-6-yl]acetic acid, WO-A-99/31075, particularly 3-(1-aminomethyl-cyclohexylmethyl)-4H-[1,2,4]oxadiazol-5-one and C-[1-(1H-tetrazol-5-ylmethyl)-cycloheptyl]-methylamine, WO-A-99/21824, particularly (3S,4S)-(1-aminomethyl-3,4-dimethyl-cyclopentyl)-acetic acid, WO-A-01/90052, WO-A-01/28978, particularly (1α,3α,5α)(3-amino-methyl-bicyclo[3.2.0]hept-3-yl)-acetic acid, EP0641330, WO-A-98/17627, WO-A-00/76958, particularly (3S,5R)-3-aminomethyl-5-methyl-octanoic acid, WO-A-03/082807, particularly (3S,5R)-3-amino-5-methyl-heptanoic acid, (3S,5R)-3-amino-5-methyl-nonanoic acid and (3S,5R)-3-amino-5-methyl-octanoic acid, WO-A-2004/039367, particularly (2S,4S)-4-(3-fluoro-phenoxymethyl)-pyrrolidine-2-carboxylic acid, (2S,4S)-4-(2,3-difluoro-benzyl)-pyrrolidine-2-carboxylic acid, (2S,4S)-4-(3-chlorophenoxy)proline and (2S,4S)-4-(3-fluorobenzyl)proline, EP1178034, EP1201240, WO-A-99/31074, WO-A-03/000642, WO-A-02/22568, WO-A-02/30871, WO-A-02/30881 WO-A-2/100392, WO-A-02/100347, WO-A-02/42414, WO-A-02/32736 and WO-A-02/28881, all of which are incorporated herein by reference.

Preferred alpha-2-delta ligands for use in the combination of the present invention include: gabapentin, pregabalin, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetc acid, (1α,3α,5α)(3-amino-methyl-bicyclo[3.2.0]hept-3-yl)-acetic acid, (3S,5R)-3-aminomethyl-5-methyl -octanoic acid, (3S,5R)-3-amino-5-methyl-heptanoic acid, (3S,5R)-3-amino-5-methyl-nonanoic acid, (3S,5R)-3-amino-5-methyl-octanoic acid, (2S,4S)-4-(3-chlorophenoxy)proline and (2S,4S)-4-(3-fluorobenzyl)proline or pharmaceutically acceptable salts thereof.

Further preferred alpha-2-delta ligands for use in the combination of the present invention are (3S,5R)-3-amino-5-methyloctanoic acid, (3S,5R)-3-amino-5-methylnonanoic acid, (3R,4R,5R)-3-amino-4,5-dimethylheptanoic acid and (3R,4R,5R)-3-amino-4,5-dimethyloctanoic acid, and the pharmaceutically acceptable salts thereof.

Particularly preferred alpha-2-delta ligands for use in the combination of the present invention are selected from gabapentin, pregabalin, (1α,3α,5α)(3-amino-methyl-bicyclo[3.2.0]hept-3-yl)-acetic acid, (2S,4S)-4-(3-chlorophenoxy)proline and (2S,4S)-4-(3-fluorobenzyl)proline or pharmaceutically acceptable salts thereof.

The compounds of the present invention may be administered in combination with an oxytocin receptor antagonist. Thus, in a further aspect of the invention, there is provided a pharmaceutical product containing a progesterone receptor antagonist and one ore more oxytocin antagonists, as a combined preparation for simultaneous, separate or sequential use in the treatment of endometriosis.

Examples of oxytocin receptor antagonists suitable for the present invention are atosiban (Ferring AB), barusiban (Ferring AB), TT-235 (Northwestern University), and AS-602305 (Serono SA).

The contents of the published patent applications mentioned above, and in particular the general formulae of the therapeutically active compounds of the claims and exemplified compounds therein, are incorporated herein in their entirety by reference thereto.

The compounds of the present invention may also be administered in combination with any one or more of the following (i) Aromatase inhibitor;
(ii) Estrogen receptor agonist;
(iii) Angiogenesis inhibitor;
(iv) VEGF inhibitor;
(v) Kinase inhibitor;
(vi) Protein farnesyl transferase inhibitor;
(vii) Androgen receptor modulator;
(viii) Androgen receptor agonists;
(ix) Androgen receptor antagonists;
(x) Prostanoid receptor agonist;
(xi) Prostanoid receptor antagonist;
(xi) Prostaglandin synthetase inhibitor;
(xii) Bioflavanoid;
(xiii) Alkylating agent;
(xiv) Microtobule modulator, e.g. Microtobule stabilizer;
(xv) Topoisomerase I inhibitor;
(xvi) Metalloprotease inhibitor; or
(xvii) Progesterone modulator.

Thus, in a further aspect of the invention, there is provided a pharmaceutical product containing a progesterone receptor antagonist and any one or more of the following (i) Aromatase inhibitor;
(ii) Estrogen receptor agonist;
(iii) Angiogenesis inhibitor;
(iv) VEGF inhibitor;
(v) Kinase inhibitor;
(vi) Protein farnesyl transferase inhibitor;
(vii) Androgen receptor modulator;
(viii) Androgen receptor agonists;
(ix) Androgen receptor antagonists;
(x) Prostanoid receptor agonist;
(xi) Prostanoid receptor antagonist;
(xi) Prostaglandin synthetase inhibitor;
(xii) Bioflavanoid;
(xiii) Alkylating agent;
(xiv) Microtobule modulator, e.g. Microtobule stabilizer;
(xv) Topoisomerase I inhibitor;
(xvi) Metalloprotease inhibitor; or
(xvii) Progesterone modulator, as a combined preparation for simultaneous, separate or sequential use in the treatment of endometriosis.

Generally, compounds of the invention will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccavmucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets", Vol. 1, by H. Lieberman and L. Lachman (Marcel Dekker, New York, 1980).

Consumable oral films are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted, and programmed release.

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic) acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactc acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol. Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted, and programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

It is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range <1 mg to 1000 mg depending, of course, on the mode of administration. For example, oral administration may require a total daily dose of from <1 mg to 1000 mg, while an intravenous dose may only require from <1 mg to 500 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

As used herein, the terms "treating" and "to treat", mean to alleviate symptoms, eliminate the causation either on a temporary or permanent basis, or to prevent or slow the appearance of symptoms. The term "treatment" includes alleviation, elimination of causation (either on a temporary or permanent basis) of, or prevention of symptoms and disorders associated with endometriosis and/or uterine leiomyoma. The treatment may be a pre-treatment as well as a treatment at the on-set of symptoms.

The compounds of the present invention may be tested in the screens set out below:

1.0 In vitro Functional Assay for Progesterone Receptor (PR) Antagonism

The assay for PR antagonism takes advantage of the extensively reported modulation of alkaline phosphatase (AP) expression in human breast T47D mammary carcinoma cells {Beck et al., D. P. (1993). The progesterone antagonist RU486 acquires agonist activity upon stimulation of cAMP signalling pathways. Proc Natl Acad Sci USA 90, 4441-4445; Fensome et al. (2002). New progesterone receptor antagonists: 3,3-disubstituted-5-aryloxindoles. Bioorg Med Chem Left 12, 3487-3490; Zhang et al., (2002a). 6-Aryl-1,4-dihydro-benzo d 1,3 oxazin-2-ones: a novel class of potent, selective, and orally active nonsteroidal progesterone receptor antagonists. Journal of Medicinal Chemistry 45, 4379-4382; Zhang et al., (2003). Novel 6-aryl-1,4-dihydrobenzo d oxazine-2-thiones as potent, selective, and orally active nonsteroidal progesterone receptor agonists. Bioorganic & Medicinal Chemistry Letters 13, 1313-1316; Zhang et al., (2002b). Potent nonsteroidal progesterone receptor agonists: synthesis and SAR study of 6-aryl benzoxazines. Bioorganic & Medicinal Chemistry Letters 12, 787-790; Zhang, Z. et al., (2000). In vitro characterization of trimegestone: a new potent and selective progestin. Steroids 65, 637-643.}. In the presence of progesterone, endogenous AP expression is induced in T47D cells and is inhibited by compounds possessing PR antagonistic activity. In the absence of progesterone any agonist activity is also observed as an induction of AP activity. By running the assay in two formats (+/−progesterone (P4)), compounds behaving as PR antagonists, agonists or partials can be identified.

The materials required to grow T47D cells and perform the progesterone-induced AP assay are outlined in Table 1.

TABLE 1

| | | |
|---|---|---|
| Assay media (agonist format): DMEM without phenol red + 5% CS-FCS + 2 mM Glutamax. | | |
| Assay media (antagonist format): DMEM without phenol red + 5% CS-FCS + 2 mM Glutamax + 10 nM P4. | | |

| Reagent | Supplier | Catalogue number |
|---|---|---|
| T47D human mammary carcinoma cells | American tissue culture collections; http://www.atcc.org/ | HTB-133 |
| Dimethyl sulphoxide (DMSO) | Sigma | D2650 |
| Dulbecco's modified Eagle's Medium (DMEM) | Gibco | 21969-035 |
| DMEM without phenol red | Gibco | 31053-028 |
| L-Glutamax, 200 mM | Gibco | 35050-038 |
| Charcoal stripped foetal calf serum (CS-FCS) | Globepharm | |
| Phosphate buffered saline (PBS) | Gibco | 14190-094 |
| Foetal bovine serum (FBS) | Sigma | F-7524 |
| BD Great EscAPe SEAP Chemiluminescence Detection kit | Fisher | K2041-1 |
| Progesterone (P4) | Sigma | P-6149 |
| Pluronic-F127 | Molecular Probes | P6867 |
| RU486 (Mifepristone) | Sigma | M-8046 |

Briefly, T47D cells are grown by propagating in DMEM+ 10% FBS+2 mM Glutamax at 37° C./5% $CO_2$. At 80-90% confluence, the media is exchanged for phenol red free DMEM+5% CS-FCS (Assay media) and cultured for a further 24 hrs at 37° C./5% $CO_2$. T47D cells are then plated at $2.5 \times 10^4$ cells/well in 100 µL assay media in sufficient 96 well plates for the assay, in triplicates of each condition. For example, for a 5 point $IC_{50}$ curve on one compound, this is equivalent to 36 wells (2×18 wells, ±P4). These plates are then cultured for 24 hrs at 37° C./5% $CO_2$, leaving the outside wells blank by the addition of 200 µL PBS.

A 10 mM stock solution of compounds is prepared in DMSO (stored −20° C. in 10 □L aliquots). A 10 mM DMSO stock of RU486 is used as a standard pure PR antagonist. The compounds under investigation are added to assay medium, or a mixture of 0.05% pluronic acid in PBS, ±10 nM P4 to give a final concentration of 20 □M (i.e. 10 □L of the 10 mM stock to 5 □L assay medium ±10 nM P4). The samples are mixed thoroughly and serial dilutions of compounds from 10 □M to 0.1 nM in a 96 well plate, are prepared as follows:

The outside wells are left blank. Assay medium (225 µL) is added to one half of the plate (−P4), rows 3-8, and to the other half of the plate, assay medium +10 nM P4. To row 2, 250 µL of the top concentration of compound (20 µM±10 nM P4) is added. 25 µL of the 20 mM stock from row 2 is removed and added to the 225 µL of assay medium ±10 nM P4 in row 3 and thoroughly mixed. This process is repeated down the plate to row 7 to achieve serial dilutions. The vehicle control is adjusted to contain 0.1% DMSO (i.e. 20 µL to 10 mL assay medium ±10 nM P4 to give a concentration of 0.2% DMSO, add 250 µL to row 8).

| | A | B | C | D | E | F | G | H |
|---|---|---|---|---|---|---|---|---|
| 1 | | | | | | | | |
| 2 | | | 20 µM - P4 | | | | | |
| 3 | | | 2 µM | | | | | |
| 4 | | | 200 nM | | | | | |
| 5 | | | 20 nM | | | | | |
| 6 | | | 2 nM | | | | | |
| 7 | | | 0.2 nM | | | | | |
| 8 | | | 0 nM vehicle | | | | | |
| 9 | | | | | | | | |

100 µL of reagent from the dilution plates are transferred into the corresponding wells containing T47D cells in 100 µL assay medium, to give a final concentration of 10 µM to 0.1 nM compound (5 nM P4 antagonist format). The cells for 20 hrs at 37° C./5% $CO_2$., then media is removed, cells washed with PBS (200 µL) and lysed by placing the cells at −80° C. for 15 min and thawing at room temp. The Freeze-thaw lysis is repeated, then PBS (50 µL) is added to each well. After 5 min, 30 µL of CSPD chemiluminescent substrate solution (final 0.06125 mM, 1.25 mM substrate solution x 20 dilution with chemiluminescent enhancer, Great EscAPe SEAP Chemiluminescence Detection kit) is added to each well and mixed. The plates are incubated for 30 mins at room temperature and luminescence measured on a luminometer (VICTOR, Wallac).

The assay is performed in triplicate, in the agonist format (no exogenous P4), sigmoid fitting of the results is expressed as alkaline phosphatase induction (luminescence, arbitrary units or % with maximal progesterone response as 100%) by the test compounds. In this format, the $EC_{50}$ value is defined as the drug concentration required to produce a 50% induction of AP activity compared with 5 nM alone. Compounds with agonism, or partial agonism, that is an induction of AP activity which is sub-maximal to that induced by P4, are discarded in this way. In the antagonist format (5 nM P4), curve fitting the results is expressed as alkaline phosphatase inhibition by the test compounds. In this format, the $IC_{50}$ value is defined as the drug concentration required to produce a 50% inhibition of AP activity compared with 5 nM alone. For the purposes of compounds exemplified here, the $IC_{50}$ values are less than 5 µM. In a preferred embodiment, the $IC_{50}$ value is less than 500 nM. In a more preferred embodiment, the $IC_{50}$ is less than 50 nM.

2.0 In vitro Functional Assay for Glucocorticoid Activity (GR)

A SW1353 cell line, stably transfected with a full length GR construct and mouse mammary tumour virus (MMTV)-luciferase (Luc) reporter is used to perform the in vitro functional assay for glucocorticoid activity in this assay. The materials required to grow SW1353-MMTV-GR-Luc cells and perform the assay are indicated below, or outlined in Table 1.

SW1353-MMTV-GR-Luc cells, grown in DMEM containing 10% FBS, 2 mM glutamax and G418 (0.5 mg/mL, Gibco cat no.10131-027), are plated at $0.5 \times 10^4$ cells/well (384 well black issue culture clear bottom plates (Greiner cat no. 781091)) in 30 µL using a Multidrop micro and are incubated at 37° C., 5% $CO_2$ overnight. The culture media is replaced with assay media (30 µL; DMEM-phenol red containing 1 mg/L insulin, 2 g/L lactalbumin hydrolysate and ascorbate (0.5 mg/L), added just prior to use) for at least 4 hrs prior to dosing. The assay is performed in two formats, an antagonist format in which test compounds are assessed for their ability to block the effect of 20 nM dexamethasone on luciferase activity, and an agonist format. A separate 384 plate is used to assess compounds in both formats.

A Genesis robot is used to dilute and stamp out ½ log unit (11 point) dose responses (starting at 1 μM final; 16 compounds/384 well plate) from a 96 well plate containing 4 mM stock concentrations of compounds to be tested. The compounds under investigation are diluted in to assay medium +3.75% DMSO, or a mixture of 0.05% pluronic acid in PBS. A dexamethasone and RU-486 (1 μM final) positive control are prepared from concentrated stocks. A MATRIX Platemate is used to transfer 10 μL of diluted compounds to plates and either 10 μL of media or standards, so that the final volume of the assay is 50 μL. The cells and compounds are incubated at 37° C., 5% $CO_2$ overnight. The Steady-Glo Luci-Lite reagent (Promega cat no. E2520) is then re-constituted and 30 μL added per well, left in the dark for 5 mins and then the plate is read on a Wallac luminescence counter. All data points are measured in duplicate In the agonist format, sigmoid fitting of the results, expressed as luciferase induction (% of maximal dexamethasone response) by the test compounds, is achieved and $EC_{50}$ value is determined. In the antagonist format, results are expressed as luciferase inhibition by the test compounds and an $IC_{50}$ value is determined.

3.0 In vivo Assessment for Progesterone Receptor Antagonism Using the McPhail's Assay The classical quantitative assessment of progestogenic activity is the McPhail's assay, performed in the immature rabbit (McPhail, 1934).

According to the present invention there is also provided a process for the production of a compound of formula (I), which comprises:

(i) the condensation of a compound of formula (II) with a compound of formula (V), or a salt or hydrate thereof, optionally in the presence of an acid or a base:

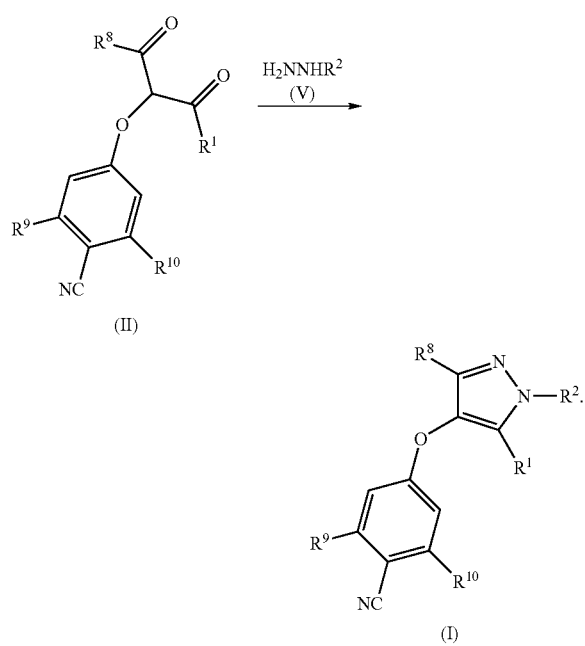

(ii) the condensation of a compound of formula (VI) with a compound of formula (V), or a salt or hydrate thereof, optionally in the presence of an acid or a base:

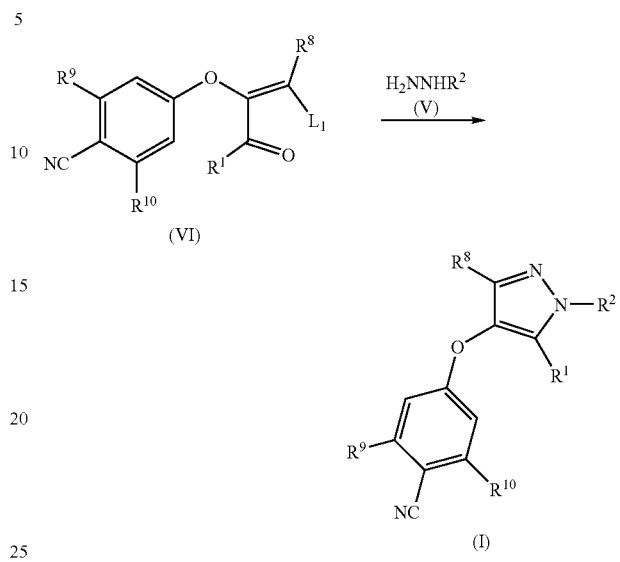

(iii) the condensation of a compound of formula (VII), with a compound of formula (V), or a salt or hydrate thereof, optionally in the presence of an acid or a base:

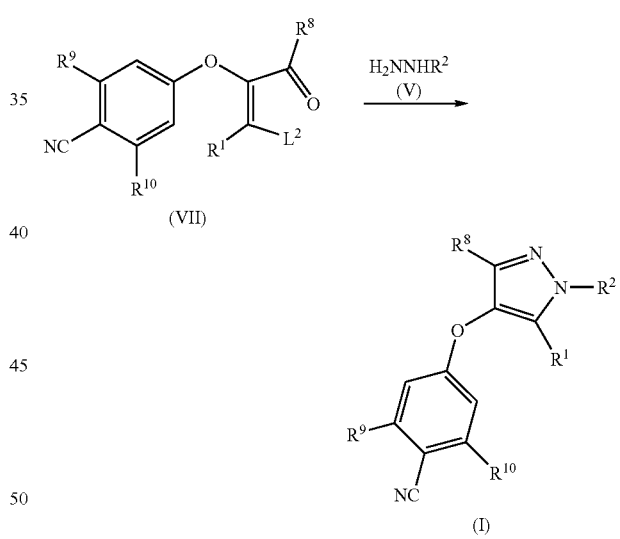

wherein $R^1$, $R^2$, $R^8$, $R^9$ and $R^{10}$ are as previously defined, and $L^1$ and $L^2$, respectively, are each suitable leaving groups; preferably —$N(C_1$-$C_6$ alkyl$)_2$, more preferably —$N(CH_3)_2$.

Also within the scope of the invention are intermediate compounds of formula (II), (VI) and (VII) as hereinbefore defined, all salts, solvates and complexes thereof and all solvates and complexes of salts thereof as defined hereinbefore for compounds of formula (I). The invention includes all polymorphs of the aforementioned species and crystal habits thereof.

When preparing compounds of formula (I) in accordance with the invention, it is open to a person skilled in the art to routinely select the form of compound of formula (II), (VI)

and (VII) that provides the best combination of features for this purpose. Such features include the melting point, solubility, processability and yield of the intermediate form and the resulting ease with which the product may be purified on isolation.

The compounds of the invention may have the advantage that they are more potent, have a longer duration of action, have a broader range of activity, are more stable, have fewer side effects or are more selective, or have other more useful properties than the compounds of the prior art.

Thus the invention provides:
(i) a compound of formula (I) or a pharmaceutically acceptable derivative thereof;
(ii) a process for the preparation of a compound of formula (I) or a pharmaceutically acceptable derivative thereof;
(iii) a pharmaceutical formulation including a compound of formula (I) or a pharmaceutically acceptable derivative thereof, together with a pharmaceutically acceptable excipients, diluent or carrier;
(iv) a compound of formula (I) or a pharmaceutically acceptable derivative or composition thereof, for use as a medicament;
(v) the use of a compound of formula (I) or of a pharmaceutically acceptable derivative or composition thereof, for the manufacture of a medicament for the treatment of endometriosis, uterine fibroids (leiomyomata), menorrhagia, adenomyosis, primary and secondary dysmenorrhoea (including symptoms of dyspareunia, dyschexia and chronic pelvic pain), chronic pelvic pain syndrome;
(vi) use as in (v) where the disease or disorder is endometriosis and/or uterine fibroids (leiomyomata);
(vii) a method of treatment of a mammal to treat endometriosis, uterine fibroids (leiomyomata), menorrhagia, adenomyosis, primary and secondary dysmenorrhoea (including symptoms of dyspareunia, dyschexia and chronic pelvic pain), chronic pelvic pain syndrome including treating said mammal with an effective amount of a compound of formula (I) or with a pharmaceutically acceptable derivative or composition thereof;
(viii) a method as in (vii) where the disease or disorder is endometriosis and/or uterine fibroids (leiomyomata);
(ix) intermediates of the formulae (II), (VI) and (VII);

All of the compounds according to the formula (I) can be prepared by conventional routes such as the procedures described in the general methods presented below, or by the specific methods described in the Examples section, or by similar methods thereto. The present invention also encompasses any one or more of these processes for preparing the compounds of formula (I), in addition to any novel intermediates used therein.

In the following general methods, $R^1$ to $R^{10}$ are as previously defined for a compound of formula (I) unless otherwise stated.

In Scheme 1 below, compounds of formula (I) may be prepared by the condensation of a compound of formula (II) with a compound of formula (V):

$$H_2NNHR^2 \quad (V)$$

or a salt or hydrate thereof, optionally in the presence of an acid or a base. The base is preferably a tertiary amine base, such as triethylamine. The acid is preferably acetic acid. In a typical procedure, a solution of the compound of formula (II) in a suitable solvent, such as ethanol, is treated with the compound of formula (V), or the salt or hydrate thereof, and, if used, the appropriate acid or base, at a temperature of from room temperature to the reflux temperature of the solvent. In a preferred procedure, the reaction mixture is heated under reflux.

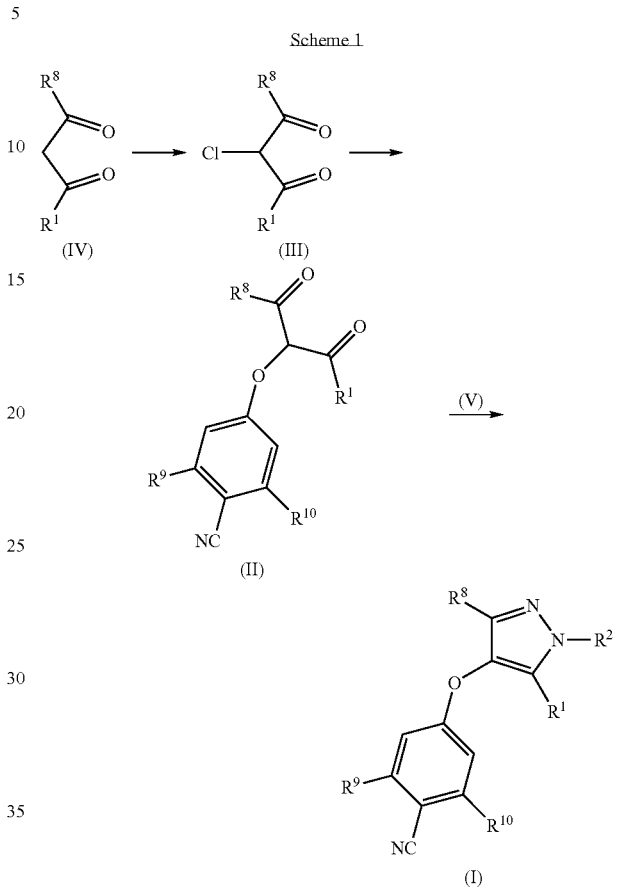

Functional equivalents of compounds of formula (II) may also be used in this reaction. These include compounds of formula (VI) or (VII) below, in which $L^1$ and $L^2$, respectively, are each suitable leaving groups; preferably —N($C_1$-$C_6$ alkyl)$_2$, more preferably —N($CH_3$)$_2$.

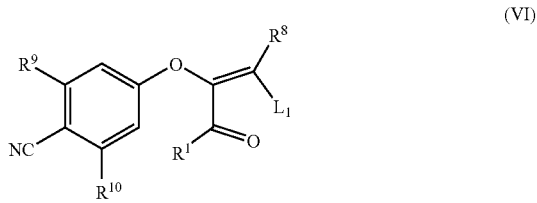

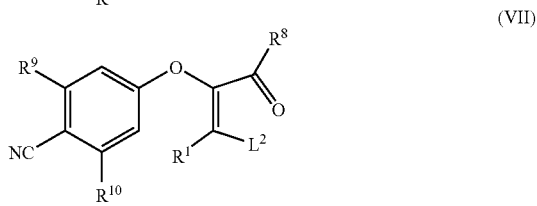

Thus, a compound of formula (I) may be prepared by the condensation of a compound of formula (VI), or (VII), with a compound of formula (V), or a salt or hydrate thereof, optionally in the presence of an acid or a base (the base preferably being a tertiary amine base, such as triethylamine, and the acid preferably being acetic acid). In a typical procedure, a solution of the compound of formula (VI), or (VII), in a suitable solvent (such as ethanol) is treated with the compound of formula (V), or the salt or hydrate thereof, and, if used, the appropriate acid or base, at a temperature of from room temperature to the reflux temperature of the solvent. In a preferred procedure, the reaction mixture is heated under reflux. Compounds of formula (VI), or (VII), are particularly suitable for the synthesis of compounds of formula (I), in which $R^1$, or $R^8$, respectively, represents H.

Compounds of formula (VI) in which $R^1$ is H and $L^1$ is dimethylamino may be prepared by the reaction of a compound of formula (VIII), below, with dimethylformamide dimethylacetal at an elevated temperature, preferably at about 100° C. Compounds of formula (VIII) in which $R^8$ is H and $L^1$ is dimethylamino may be prepared by the reaction of a compound of formula (IX), below, under the same conditions. Other compounds of formula (VI), or (VII), in which $L^1$ or $L^2$ is dimethylamino, may be prepared analogously.

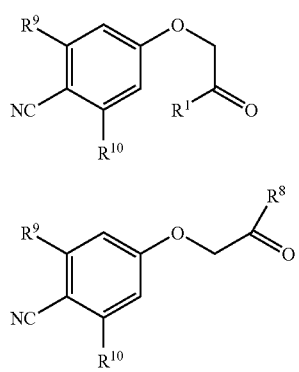

Compounds of formula (VIII) are either commercially available or may be prepared by the reaction of a compound of formula (X):

with a compound of formula (XI):

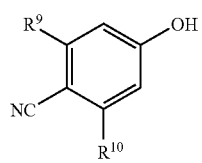

In a typical procedure, a solution of the compound of formula (XI), in a suitable solvent, such as acetone, is treated with a suitable base, such as caesium carbonate, and the compound of formula (X). In a preferred procedure, the reaction mixture is heated, for example under reflux. Optionally, a nucleophilic catalyst, such as sodium iodide or tetrabutylammonium iodide, may be added.

Compounds of formula (IX) are either commercially available or may be prepared from a compound of formula (XII):

and a compound of formula (XI), in the same way that a compound of formula (VIII) may be prepared from a compound of formula (X).

Compounds of formula (II) may be prepared by reaction of a compound of formula (III) with a compound of formula (XI). In a typical procedure, a solution of the compound of formula (III), in a suitable solvent, such as acetone, is treated with a compound of formula (XI) and a suitable base, such as potassium or caesium carbonate, and heated, preferably under reflux. Optionally, a nucleophilic catalyst such as sodium iodide, or tetrabutylammonium iodide, may be added.

Compounds of formula (III) are either commercially available or may be prepared by the reaction of a compound of formula (IV) with a chlorinating reagent. In a typical procedure, a cooled solution of the compound of formula (IV), in a suitable solvent, such as acetonitrile, is treated first with tetrabutylammonium bromide and chlorotrimethylsilane, and then dry dimethylsulphoxide. In another typical procedure, the compound of formula (IV) is treated with sulphuryl chloride, optionally in the presence of a suitable solvent, such as dichloromethane.

It will be appreciated by those skilled in the art that, in many cases, compounds of the formula (I) may be converted into other compounds of the formula (I) by functional group transformations. For instance:

(a) compounds of the formula (I) in which $R^2$ is H may be converted into compounds of the formula (I) in which $R^2$ is optionally substituted $C_1$-$C_6$ alkyl by reaction with an appropriate alkylating agent. In a typical procedure, a solution of a compound of formula (I) in which $R^2$ is H, in a suitable solvent, such as ethanol, acetonitrile or N,N-dimethylformamide, is treated with an alkyl bromide and a base, such as potassium carbonate, sodium ethoxide or sodium hydride, and heated at a temperature of from room temperature to the reflux temperature of the solvent. In a preferred combination the solvent is N,N-dimethylformamide, the base is sodium hydride and the reaction is carried out at room temperature. Examples of alkylating agents include bromoacetonitrile, ethyl bromoacetate, and halomethylheteroaryl reagents. The use of further specific alkylating agents is illustrated in the examples section described below.

(b) compounds of formula (I) in which $R^2$ is H may be converted into compounds of formula (I) in which $R^2$ is a direct linked heteroaryl or substituted phenyl, by reaction with an aryl halide, or heteroaryl halide, under metal catalysed conditions, such as copper iodide and potassium carbonate in toluene containing (1R,2R)-(−)-1,2-bis(methylamino)cyclohexane as catalyst.

(c) compounds of formula (I) in which $R^2$ contains an ester, may be converted into compounds of formula (I) in which $R^2$ contains an amide by aminolysis of the ester with an amine in a suitable solvent such as methanol, ethanol or tetrahydrofuran. Alternatively the ester may be first hydrolysed to the corresponding carboxylic acid, and then converted to an amide using commonly used methods.

(d) compounds of formula (I) in which $R^2$ contains a primary carboxamide may be converted into compounds of formula (I) in which $R^2$ contains a nitrile by dehydration with a suitable dehydrating agent, such as trifluoroacetic anhydride.

The following Preparations and Examples illustrate the preparation of the compounds of formula (I).

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad.

The following abbreviations have been used throughout:

| | |
|---|---|
| HRMS | high resolution mass spectrometry; |
| LRMS | low resolution mass spectrometry; |
| hplc | high performance liquid chromatography; |
| nOe | nuclear Overhauser effect; |
| m.p | melting point; |
| CDCl$_3$ | deuterochloroform; |
| D$_6$-DMSO | deuterodimethylsulphoxide; |
| CD$_3$OD | deuteromethanol |

Where thin layer chromatography (TLC) has been used it refers to silica gel TLC using silica gel 60 F$_{254}$ plates. "R$_f$" represents the distance travelled by a compound divided by the distance travelled by the solvent front on a TLC plate.

Where it is stated that compounds were prepared in the manner described for an earlier Preparation or Example, the skilled person will appreciate that reaction times, number of equivalents of reagents and reaction temperatures may be modified for each specific reaction, and that it may nevertheless be necessary or desirable to employ different work-up or purification conditions.

Preparation 1:
4-(1-Acetyl-2-oxopropoxy)benzonitrile

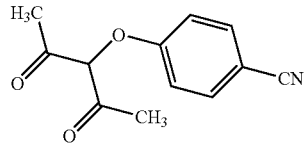

A mixture of commercially available 3-chloro-2,4-pentanedione (14.01 ml, 92 mmol), 4-cyanophenol (10 g, 84 mmol), caesium carbonate (29.9 g, 92 mmol) and acetone (160 ml) was heated under reflux for 5 hours. After cooling, a solid was removed by filtration and it was washed with dichloromethane (100 ml). The combined filtrates were concentrated under reduced pressure. The remaining oil was diluted with dichloromethane (150 ml), washed with 1M hydrochloric acid (100 ml), then brine (50 ml), dried over magnesium sulphate, filtered and finally concentrated under reduced pressure. The crude product was purified by flash chromatography on silica gel eluting with pentane:ethyl acetate (15:1, by volume then 10:1) to provide the title compound, which crystallised on standing, as pale yellow crystals (7.27 g, 39.6%).

$^1$H-NMR (400 MHz, CDCl$_3$): δ=2.01 (s, 6H), 7.02 (d, 2H), 7.64 (d, 2H); LRMS: APCl$^-$ m/z: 216 [M-H]$^-$; Microanalysis: Found: C, 65.82; H, 5.18; N, 6.17%. C$_{12}$H$_{11}$NO$_3$ requires C, 66.35; H, 5.10; N, 6.45%.

Preparation 2: 4-Hydroxy-2-methyl benzonitrile

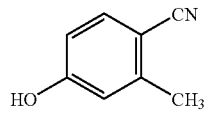

Boron trichloride (1M in dichloromethane, 747 ml, 747 mmol) was added dropwise, at −78° C., to a suspension of commercially available 4-methoxy-2-methyl-benzonitrile (44 g, 298 mmol) and tetrabutylammonium iodide (121 g, 327 mmol) in dichloromethane (750 ml), under nitrogen, over 40 minutes. Once the addition was complete, the yellow solution was warmed to room temperature and stirred for 16 hours at room temperature. The reaction mixture was then quenched by dropwise addition of water maintaining the internal at temperature below 10° C. The mixture was then filtered through Arbocel™, and the layers were separated. The aqueous layers were extracted with dichloromethane (250 ml). The organic layers were combined, washed with a sodium thiosulphate solution, dried over magnesium sulphate, filtered and concentrated under reduced pressure to give a thick yellow oil. Trituration of the oil in dichloromethane, followed by filtration, provided a first crop of the title compound (10.85 g, 27.4%) as a white solid. The filtrate was evaporated and purified by flash chromatography on silica gel, eluting with pentane:ethyl acetate (70:30, by volume) to provide more of the title compound as a white solid (14.44 g, 36.4%).

$^1$H-NMR (400 MHz, CDCl$_3$): δ=2.46 (s, 3H), 6.68 (d, 1H), 6.72 (s, 1H), 7.45 (d, 1H); LRMS: APCl$^-$: m/z 132 [M-H]$^-$.

Preparation 3: 4-Hydroxy-2-methoxy benzonitrile

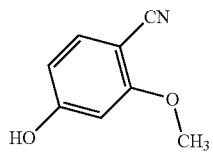

Trifluoroacetic anhydride (1.3 ml, 9.36 mmol) was added to a solution of 4-hydroxy-2-methoxybenzamide {*Liebigs Ann Chem* (1982)1836-1869} (600 mg, 3.6 mmol) and pyridine (0.72 ml, 9.36 mmol), in tetrahydrofuran (10 ml), and the mixture was stirred at room temperature for 18 hours. The reaction mixture was then concentrated under reduced pressure and treated with 2M hydrochloric acid (100-ml). It was then extracted with ethyl acetate (2×100 ml). The organic layers were combined and washed with brine (100 ml), dried over magnesium sulphate, filtered and then evaporated under reduced pressure to give an orange solid. The crude product was purified by flash chromatography on silica gel eluting with pentane:ethyl acetate (70:30 to 50:50, by volume) to provide the title compound (320 mg, 60%) as a pale yellow solid.

$^1$H-NMR (400 MHz, CDCl$_3$): δ=3.89 (s, 3H), 6.06 (s, 1H), 6.45 (s, 2H), 7.41 (d, 1H); LRMS:APCl$^-$: m/z 148 [M-H]$^-$.

Preparation 4:
4-Hydroxy-2-(trifluoromethyl)benzonitrile

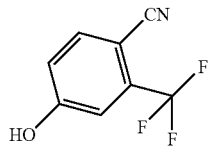

2-(Methylsulfonyl)ethanol (30.5 g, 239 mmol) was added to a solution of 4-hydroxy-2-(trifluoromethyl)benzonitrile (30 g, 159 mmol) in N-methylpyrrolidinone (250 ml), and then the solution was cooled down to 2° C. Sodium hydride (60% dispersion in oil, 19.08 g, 477 mmol) was added portionwise over 1.75 hours, during which time hydrogen was evolved, a small exotherm occurred (up to 8° C.) and the mixture gradually turned brown. At the end of the addition, the mixture was warmed to room temperature and stirred for an hour, in which time it turned black. It was then poured gradually into a well-stirred mixture of 2N hydrochloric acid (300 ml) and ice (700 g). The unreacted sodium hydride caused a small effervescence. The resulting brown suspension was then treated with diethyl ether:cyclohexane 1:1 (500 ml) and filtered through Arbocel™ to remove the dark brown material. The filtrate layers were separated and the aqueous layer was extracted again with diethyl ether:cyclohexane 1:1 (2×500 ml). The combined orange organic layers were washed with brine (3×300 ml), dried over magnesium sulphate and filtered through a pad of silica gel to remove brown solid. The filtrate was concentrated under reduced pressure to give a yellow solid, which was then slurried in pentane (100 ml) for 30 minutes. Filtration and washing with pentane provided the title compound (27.94 g, 94%) as a pale yellow solid.

$^1$H-NMR (400 MHz, CDCl$_3$): δ=6.45 (s, 1H), 7.06 (dd, 1H), 7.69 (d, 1H); LRMS: ESI$^-$: m/z 373 [2M-H]$^-$; Mp=120° C.

Preparation 5: 1,3-Dicyclopropyl-propane-1,3-dione

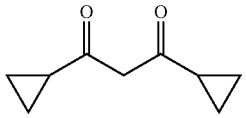

Methylcyclopropanecarboxylate (20.2 ml, 286.3 mmol) was added to a stirred solution of 1-cyclopropylethanone (9 ml, 152.4 mmol) in dimethylsulfoxide (25 ml). Sodium methoxide powder (10.8 g, 200 mmol) was added, and the reaction was stirred at 55° C. for 8 hours. The reaction mixture was then cooled, diluted with toluene (200 ml), neutralised with 6M hydrochloric acid (50 ml), separated and then extracted with toluene (100 ml). The combined extracts were washed with sodium carbonate (150 ml), dried over magnesium sulphate and evaporated in vacuo to provide the title compound (14.9 g, 78%) as a mixture 2:1 enol:ketone forms.

$^1$H NMR (CDCl$_3$, 400 MHz): δ=0.79-0.87 (m, 4H), 0.98-1.01 (m, 4H), 1.46-1.51 (m, 2H-enol), 1.93-1.97 (m, 2H-keto), 3.70 (s, 2H-keto), 5.65 (s, 1H-enol); LRMS: APCl$^+$: m/z 153 [MH$^+$]; APCl$^-$ $^{m/z}$ 151 [M-H]$^-$ Preparation 6a:
2-Chloro-1,3-dicyclopropyl-1,3-propanedione

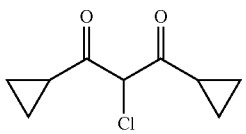

Chlorotrimethylsilane (36 ml, 296 mmol) was added dropwise to a stirred solution of tetrabutylammonium bromide (1.54 g, 5 mmol) in dry acetonitrile (100 ml) at room temperature, under nitrogen. The resulting solution was cooled in ice, and the diketone described in Preparation 5 (15 g, 98.7 mmol) as a solution in acetonitrile (30 ml) was added dropwise, followed by dry dimethylsulphoxide (20 ml, 296 mmol). The reaction mixture was allowed to warm slowly to room temperature, and then stirred for 18 hours. The reaction mixture was diluted with water (200 ml), stirred for 10 minutes and then extracted with diethyl ether (50 ml). The layers were separated, and the aqueous layer was extracted again with diethyl ether (100 ml). The organic layers were combined, dried over magnesium sulphate, filtered and concentrated under reduced pressure. The crude product was purified by column chromatography on silica gel eluting with pentane:diethyl ether (20:1, by volume) to provide the title compound as a 2:7 mixture of keto:enol tautomers (12.1 g, 66%).

$^1$H NMR (400 MHz, CDCl$_3$): δ=1.01-1.07 (m, 4H), 1.16-1.21 (m, 4H), 2.23-2.28 (m, 2H-keto), 2.39-2.44 (m, 2H-enol), 5.07 (s, 1H-keto); LRMS:APCl$^+$: m/z 187 [MH$^+$]; APCl$^-$ m/z 185 [M-H]$^-$ Preparation 6b:
2-Chloro-1,3-dicyclopropyl-1,3-propanedione

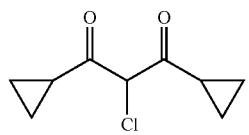

The diketone described in Preparation 5 (700 g, 4.6 mol) was dissolved in dichloromethane (7 L) with chlorotrimethylsilane (549 g, 5.08 mol), at room temperature. The solution was stirred for 45 minutes, after which time it was cooled to 10 to 15° C. N-chlorosuccinimide (614 g, 4.6 mol) was then added portion-wise, keeping the temperature between 10 and 15° C. The reaction was then warmed to room temperature and stirred for a further 30 minutes. The reaction slurry was then filtered and the organic solution was washed twice with 2M hydrochloric acid (2×1.8 L), followed by two washes with water (2×4.6 L). The organic layer was then dried over anhydrous magnesium sulphate before being concentrated to an oil under vacuum to provide the title compound as a 2:3 mixture of keto:enol tautomers. (780 g, 91%)

$^1$H NMR (300 MHz, CDCl$_3$): δ=1.00-1.07 (m, 4H), 1.08-1.14 (m, 4H), 2.14-2.22 (m, 2H-keto), 2.30-2.37 (m, 2H-enol), 4.99 (s, 1H-keto).

Preparation 7: 3-Oxobutanoic acid

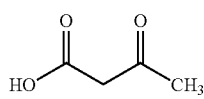

Sodium hydroxide (37.9 g, 947 mmol) was dissolved in water (770 ml) and added to a solution of 3-oxo-butanoic acid methyl ester (100 g, 861 mmol), at room temperature, over 20 minutes. The reaction mixture was stirred for 18 hours, after which time it was quenched with ammonium sulfate (700 g) and acidified slowly with a solution of concentrated hydrochloric acid (21.5 ml) in water (250 ml), with ice cooling. The reaction mixture was then extracted with diethyl ether (6×200 ml) and the combined organic extracts were dried over magnesium sulphate, and concentrated under reduced pressure to provide the title compound (58.2 g, 60%) as a pale yellow oil, which was a mixture of keto:enol tautomers.

$^1$H NMR (400 MHz, CDCl$_3$): δ=2.00 (s, 3H-enol), 2.30 (s, 3H-keto), 3.51 (s, 2H-keto), 5.02 (s, 1H-enol).

Preparation 8: 1-Cyclopropyl-1,3-butanedione

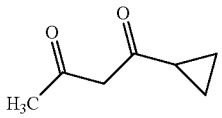

Magnesium turnings (3.04 g, 125 mmol), suspended in methanol (145 ml), were heated to reflux under nitrogen for 1 hour, then cooled to room temperature and the β-keto acid described in Preparation 7 (25.5 g, 250 mmol), dissolved in methanol (25 ml), was added dropwise, with ice-cooling. The reaction mixture was stirred for 1 hour, at room temperature, and then the solvent was removed under reduced pressure to give the magnesium salt of the acid. Meanwhile, cyclopropane-carboxylic acid (9.91 ml, 125 mmol) was dissolved in dimethylformamide (200 ml). Carbonyldiimidazole (22.4 g, 138 mmol) was then added portionwise, under nitrogen, at 0° C. This reaction mixture was stirred for 1.5 hours, and then the magnesium salt from above was added as a solution in N,N-dimethylformamide (100 ml) at 0° C. The reaction mixture was allowed to stir at room temperature for 92 hours, and then it was poured into 2M aqueous hydrochloric acid (85 ml), followed by dilution with water (170 ml). The mixture was extracted with diethyl ether (6×200 ml), and the combined organic extracts were then washed with brine (3×200 ml), dried over magnesium sulphate and concentrated under reduced pressure. The residual orange oil was purified by flash chromatography on silica gel eluting with pentane:diethyl ether (100:0 then 90:10 then 80:20, by volume) to provide the title compound (7.39 g, 24%) as a yellow oil.

$^1$H NMR (400 MHz, CDCl$_3$): δ=0.83-0.95 (m, 2H), 1.06-1.10 (m, 2H), 1.54-1.63 (m, 1H), 2.00 (s, 3H); LRMS (electrospray): m/z 149 [MNa$^+$].

Preparation 9:
2-Chloro-1-cyclopropyl-1,3-butanedione

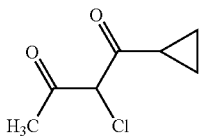

The title compound (7.9 g, 62%, 3:2 mixture of keto:enol tautomers) was prepared by a similar method to that described for Preparation 6, using the diketone described in preparation 8 as starting material (10 g).

$^1$H NMR (400 MHz, CDCl$_3$): δ=1.01-1.04 (m, 2H), 1.14-1.20 (m, 2H), 2.27 (s, 3H), 2.43 (m, 1H); LRMS: APCl$^+$: m/z 161 [MH$^+$]; APCl$^-$ m/z 159 [M-H]$^-$

Preparation 10: 4-Chloro-3,5-heptanedione

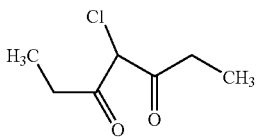

The title compound was prepared by a similar method to that described for Preparation 6 using commercially available 3,5-heptanedione as starting material. Purification by distillation under reduced pressure afforded the title compound (5.5 g, 15%) as a pale yellow oil, b.p. 102-105° C./54 mmHg, containing ca. 10% 4,4-dichloro-3,5-heptanedione as estimated by microanalysis.

$^1$H-NMR (400 MHz, CDCl$_3$): δ=1.12 (t, 6H), 2.59 (q, 4H), 4.77 (s, 0.2H, diketone), 15.50 (s, 0.8H, enol); LRMS (thermospray): m/z 180 [MNH$_4^+$] for title compound and 214 for dichlorinated impurity.

Preparations 11 to 14

The compounds of the following preparations having the general formula:

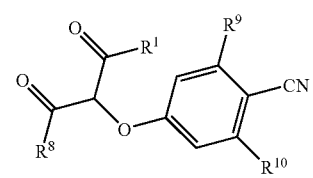

were prepared by a similar method to that described in Preparation 1, using the appropriate chlorodiketone and phenol as starting materials.

| Prep$^n$ No. | R$^9$; R$^{10}$; R$^8$; R$^1$ Analytical Data |
|---|---|
| 11$^a$ | R$^9$=H; R$^{10}$=H; R$^8$=Et; R$^1$=Et<br>$^1$H-NMR(400MHz, CDCl$_3$, enol form): δ=1.02(t, 6H), 2.26(q, 4H), 7.00(d, 2H), 7.60(d, 2H); LRMS: APCl$^-$: m/z 244[M-H]$^-$. 71% yield |
| 12$^b$ | R$^9$=Me; R$^{10}$=Me; R$^8$=Me; R$^1$=cPr<br>$^1$H-NMR(400MHz, CDCl$_3$, enol form): δ=0.89-0.92(m, 2H), 1.14-1.16(m, 2H), 1.87(m, 1H), 1.97(s, 3H), 2.50(s, 6H), 6.71(s, 2H); LRMS: APCl$^+$: m/z 272[MH$^+$]; APCl$^-$: m/z 270[M-H]$^-$; 30% yield |
| 13$^c$ | R$^9$=Me; R$^{10}$=Me; R$^8$=cPr; R$^1$=cPr<br>$^1$H-NMR(400MHz, CDCl$_3$, enol form): δ=0.87-0.91(m, 4H), 1.12-1.15(m, 4H), 1.79-1.84(m, 2H), 2.52(s, 6H), 6.77(s, 2H); LRMS: APCl$^+$: m/z 298[MH$^+$]; APCl$^-$: m/z 296[M-H]$^-$; 60% yield |
| 14$^d$ | R$^9$=Me; R$^{10}$=H; R$^8$=Me; R$^1$=cPr<br>$^1$H-NMR(400MHz, CDCl$_3$, enol form): δ=0.89-0.92(m, 2H), 1.13-1.16(m, 2H), 1.86(m, 1H), 1.98(s, 3H), 2.53(s, 3H), 6.86(d, 1H), 6.90(s, 1H), 7.56(d, 1H); LRMS: APCl$^-$: m/z 256[M-H]$^-$; 88% yield |

$^a$from Prep$^n$ 10 and commercial phenol
$^b$from Prep$^n$ 9 and commercial phenol
$^c$from Prep$^n$ 6 and commercial phenol
$^d$from Prep$^n$ 9 and Prep$^n$ 2

Preparation 15: 4-[(5-Ethyl-3-oxo-2,3-dihydro-1H-pyrazol-4-yl)oxy]benzonitrile

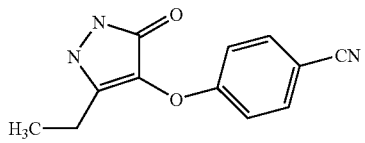

4-Cyanophenol (1.19 g, 10 mmol) and caesium carbonate (3.25 g, 10 mmol) were added to a solution of methyl-2-chloro-3-pentanoate (1.37 ml, 10 mmol) in acetone (20 ml) and the reaction mixture was heated to 60° C. for 4 hours. The mixture was then filtered through Arbocel™ and washed with acetone. The filtrates were concentrated under reduced pressure to give crude methyl 2-(4-cyanophenoxy)-3-oxopentanoate (2.5 g), which was taken forward into the next step as crude compound. Hydrazine hydrate (0.5 ml, 10 mmol) was added to a solution of this intermediate in acetic acid (30 ml) and the reaction mixture was heated at 70° C. for 18 hours. The mixture was then evaporated to a solid residue. Water (30 ml) and diisopropyl ether (30 ml) were added, and the solid was slurried for 30 minutes. The solid was then filtered off, washed with water (50 ml) and diisopropyl ether (50 ml) to provide the title compound as a solid (1.3 g, 57%).

$^1$H-NMR (400 MHz, DMSO-D$_6$): δ=1.02 (t, 3H), 2.35 (q, 2H), 7.01 (d, 2H), 7.76 (d, 2H); LRMS APCl$^+$: m/z 230 [MH$^+$]; APCl$^-$ m/z 228 [M-H]$^-$.

Preparation 16: tert-Butyl 4-(4-cyanophenoxy)-5-ethyl-3-oxo-2,3-dihydro-1H-pyrazole-1-carboxylate

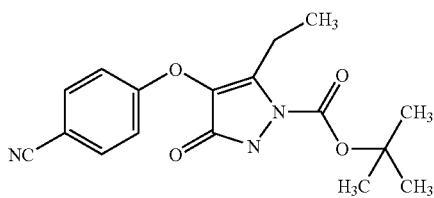

To a stirred solution of the benzonitrile of Preparation 15 (800 mg, 3.5 mmol) in N,N-dimethylformamide (10 ml), under nitrogen, were added potassium carbonate (580 mg, 4.2 mmol) and di-tert-butyl dicarbonate (915 mg, 4.2 mmol), dissolved in N,N-dimethylformamide (10 ml). The reaction mixture was stirred at 50° C. for 6 hours. It was then partitioned between ethyl acetate (100 ml) and water (200 ml). The organic layer was separated and the aqueous layer was extracted with dichloromethane (3×50 ml). The organic extracts were combined, dried over magnesium sulphate, filtered and evaporated to give a pale orange solid, which was purified by flash chromatography on silica gel eluting with dichloromethane:methanol (99:1, by volume). Trituration of the solid with diisopropyl ether:pentane provided the title compound as a cream coloured solid (842 mg, 73%).

$^1$H-NMR (400 MHz, CDCl$_3$): δ=1.16 (t, 3H), 1.42 (s, 9H), 2.88 (q, 2H), 7.05 (d, 2H), 7.60 (d, 2H); LRMS: APCl$^+$: 230 [(M-Boc)H$^+$]; APCl$^-$: 328 [M-H]$^-$.

Preparation 17: tert-Butyl 4-(4-cyanophenoxy)-5-ethyl-3-methoxy-1H-pyrazole-1-carboxylate

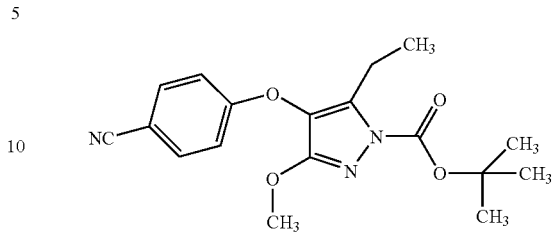

Triphenylphosphine (240 mg, 0.91 mmol) was dissolved in tetrahydrofuran (5 ml), and then methanol (37 μl, 0.91 mmol) was added, followed by diisopropyl azodicarboxylate (185 mg, 0.91 mmol). The reaction mixture was stirred under nitrogen for 5 minutes, until it had almost decolourised, and then the pyrazole carboxylate of Preparation 16 (200 mg, 0.61 mmol) was added. The reaction mixture was stirred at room temperature for 3 hours. Analysis by TLC showed the presence of both N- and O-alkyl products, with O-alkyl being the major component. The reaction mixture was then evaporated and the crude product was purified by flash chromatography on silica gel eluting with ethyl acetate:pentane (1:9 then 7:3, by volume). The faster running O-alkyl title compound was isolated as a colourless oil (89 mg, 43%).

$^1$H-NMR (400 MHz, CDCl$_3$): δ=1.13 (t, 3H), 1.64 (s, 9H), 2.79 (q, 2H), 3.95 (s, 3H), 6.98 (d, 2H), 7.59 (d, 2H); LRMS: APCl$^+$: 244 [(M-Boc)H$^+$]; APCl$^-$: 242 [(M-Boc)-H]$^-$; HPLC/ESMS: UV/ELSD single peak at 344 [MH$^+$]; HRMS: consistent with product molecular formula.

Preparation 18: 4-[(3-Ethyl-1H-pyrazol-4-yl)oxy]benzonitrile

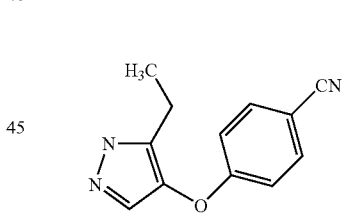

1-Bromo-2-butanone (1.51 g, 10 mmol) was added to a solution of 4-hydroxybenzonitrile (1.19 g, 10 mmol) and caesium carbonate (3.25 g, 10 mmol), in acetone (50 ml). The reaction mixture was then heated at 60° C. for 2 hours. After cooling, it was concentrated under reduced pressure. Water (25 ml) was added and the mixture was extracted with ethyl acetate (2×50 ml). The combined organic layers were washed with brine, dried over magnesium sulphate, filtered and concentrated under reduced pressure to give crude 4-(2-oxobutoxy)benzonitrile intermediate (1.83 g) (9.6 mmol). Ethyl formate (407 mg, 5.5 mmol) was added to a solution of the crude intermediate (945 mg, 5 mmol) in ethanol (5 ml). The reaction mixture was then cooled to 0° C. and sodium ethoxide (21% wt solution in ethanol, 1.78 ml, 5.5 mmol) was added dropwise over 2 minutes at 0° C. under nitrogen. The reaction mixture was then warmed to room temperature and stirred for 18 hours, after which time 0.5N hydrochloric acid (25 ml) was added and the mixture was extracted with diethyl ether (2×50 ml). The combined organic layers were washed with brine, dried over magnesium sulphate and concentrated under reduced pressure to provide crude 4-(1-formyl-2-oxobutoxy)benzonitrile (820 mg, 3.78 mmol). This intermediate was then dissolved in acetic acid (10 ml), and then hydrazine hydrate (320 mg, 6.4 mmol) was added. The reaction mixture was stirred at room temperature for 2 hours, under nitrogen. It was then concentrated under reduced pressure, and the residue was purified by flash chromatography on silica gel, eluting with ethyl acetate:pentane (30:70 to 40:60, by volume), to provide the title compound (118 mg, 15%) as a solid.

$^1$H-NMR (400 MHz, CDCl$_3$): δ=1.20 (t, 3H), 2.56 (q, 2H), 7.01 (d, 2H), 7.43 (s, 1H), 7.59 (d, 2H); LRMS: APCl+: m/z 214 [MH+]; APCl$^-$: m/z 212 [M-H]$^-$. Microanalysis: Found: C, 67.62; H, 5.19; N, 18.99%. C$_{12}$H$_{11}$N$_3$O requires C, 67.59; H, 5.20; N, 19.71%.

Preparation 19: 4-(2-Cyclopropyl-2-oxoethoxy)-2,6-dimethylbenzonitrile

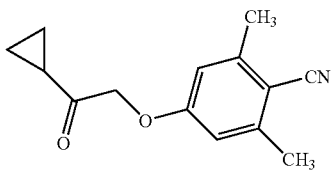

Bromine (12.84 ml, 250 mmol) was added dropwise, over 10 minutes, to an ice-cooled solution of cyclopropylmethylketone (21 g, 250 mmol), in methanol (150 ml), under nitrogen. The reaction was allowed to proceed with the internal temperature being kept under 10° C., until decolourisation of the solution was observed. The reaction mixture was then stirred at room temperature for a further 30 minutes, after which time water (75 ml) was added and the reaction mixture was stirred for a further 15 minutes. The reaction mixture then was diluted with water (225 ml) and extracted 4 times with diethyl ether (50 ml). The organic layers were combined, washed with a 10% aqueous solution of sodium bicarbonate, followed by water, followed by brine, then dried over magnesium sulphate, filtered and concentrated under reduced pressure to provide 2-bromo-1-cyclopropylethanone.

Caesium carbonate (30.7 g, 111.16 mmol) was added to a solution of 4-hydroxy-2,6-dimethylbenzonitrile (15.27 g, 101.89 mmol), in acetone (377 ml). Then 2-bromo-1-cyclopropylethanone (15.1 g, 62.6 mmol), in acetone (100 ml), was added dropwise, over 5 minutes, to the resulting suspension and the reaction mixture was heated at reflux for 1.5 hours. It was then concentrated under reduced pressure and the residue was partitioned between an aqueous solution of potassium carbonate and dichloromethane. The organic layer was separated and washed with brine, dried over magnesium sulphate, filtered and then concentrated under reduced pressure. The crude product was purified by flash chromatography on silica gel eluting with dichloromethane:pentane (50:50 to 80:20, by volume) to provide the title compound (13.5 g, 64%) as a solid.

$^1$H-NMR (400 MHz, CDCl$_3$): δ=0.97-1.01 (m, 2H), 1.12-1.15 (m, 2H), 2.19 (m, 1H), 2.47 (s, 6H), 4.71 (s, 2H), 6.61 (s, 2H); LRMS: APCl$^+$: 230 [MH$^+$]

Preparation 20: 4-{([(E/Z)-1-(Cyclopropylcarbonyl)-2-(dimethylamino)vinyl]oxy}-2,6-dimethylbenzonitrile

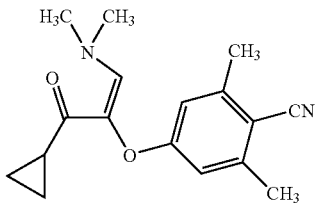

The benzonitrile of Preparation 19 (11.8 g, 51.46 mmol) and N,N-dimethylformamide dimethyl acetal (13.7 ml, 102.93 mmol) were heated at 105° C. for 12 hours. The reaction mixture was then concentrated under reduced pressure. The crude product was purified by flash chromatography on silica gel eluting with dichloromethane:pentane (50:50 then 80:20 then 100:0, by volume) to provide the title compound (11.19 g, 76%) as a white solid.

$^1$H-NMR (400 MHz, CDCl$_3$): δ=0.63 (brs, 2H), 0.91 (brs, 2H), 1.93 (m, 1H), 2.44 (s, 6H), 2.96 (s, 6H), 6.69 (s, 2H); LRMS: APCl$^+$: 285 [MH$^+$]

Preparation 21: tert-Butyl[4-(4-cyano-3,5-dimethylphenoxy)-3-cyclopropyl-1H-pyrazol-1-yl]acetate

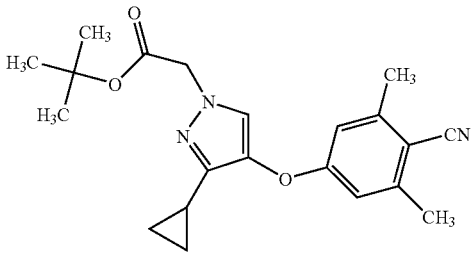

The title compound (1.80 g, 100%) was prepared by a similar method to that described for the acetate of step (a) of Example 80 using the benzonitrile of Example 16 as starting material.

$^1$H-NMR (400 MHz, CDCl$_3$): δ=0.77-0.83 (m, 4H), 1.47 (s, 9H), 1.63 (m, 1H), 2.47 (s, 6H), 4.68 (s, 2H), 6.72 (s, 2H), 7.28 (s, 1H).

LRMS: APCl$^+$: m/z 368 [MH$^+$] and 312 [acidH$^+$].

Preparation 22: 5-(Bromomethyl)pyrimidine

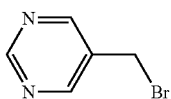

N-Bromosuccinimide (2.33 g, 13.17 mmol) was added to a solution of 5-methylpyrimidine (1 g, 10.6 mmol) in carbon tetrachloride (100 ml). Then 2,2'-azobisisobutyronitrile was added, in a catalytic amount. The reaction mixture was heated at reflux for 1 hour, then cooled, and the solid which had formed was filtered off. The filtrate was concentrated under reduced pressure, and the residue was partitioned between dichloromethane (150 ml) and a saturated aqueous solution of sodium bicarbonate (50 ml). The organic layer was dried over magnesium sulphate and concentrated under reduced pressure to provide the title compound (1.01 g, 55%), contaminated with dibromomethylpyrimidine (ca 30%).

¹H-NMR (400 MHz, CDCl₃): δ=4.42 (s, 2H), 6.61 (s, 1H, diBr), 8.78 (s, 2H), 8.95 (s, 2H, diBr), 9.14 (s, 1H), 9.16 (s, 1H, diBr).

Preparation 23: 5-(Bromomethyl)isoxazole

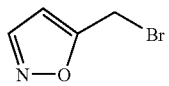

The title compound (2.4 g, 61%) was prepared by a similar method to that described for the pyrimidine of Preparation 22 using 5-methylisoxazole as the starting material.
LRMS: APCl⁺: m/z 163 [MH⁺].

Preparation 24: 1-[(4-Methylphenyl)sulfonyl]-1H-imidazole-2-carboxaldehyde

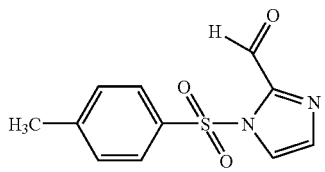

p-Toluenesulphonyl chloride (3.8 g, 20 mmol) was added to a suspension of 1Himidazole-2-carboxaldehyde (1.92 g, 20 mmol) and triethylamine (2.8 ml, 20 mmol) in dichloromethane (50 ml). 1,4-Dimethylaminopyridine (20 mg, 0.4 mmol) was added and the reaction mixture was stirred at room temperature for 18 hours. It was then diluted with dichloromethane (100 ml) and washed with brine (100 ml). The organic layer was dried over magnesium sulphate and concentrated under reduced pressure. The crude product was purified by flash chromatography on silica gel eluting with ethyl acetate:pentane (20:80, then 50:50 by volume) to provide the title compound (2.61 g, 52%) as a yellow oil, which crystallised upon standing.

¹H-NMR (400 MHz, CDCl₃): δ=2.44 (s, 3H), 7.31 (s, 1H), 7.37 (d, 2H), 7.83 (s, 1H), 8.00 (d, 2H), 9.78 (s, 1H); LRMS: APCl⁺: m/z 251 [MH⁺]; APCl⁻ m/z 249 [M-H]⁻; Microanalysis: Found C, 52.68; H, 3.94; N, 11.07%. C₁₁H₁₀N₂O₃S requires C, 52.80; H, 4.00; N, 11.20%.

Preparation 25: {1-[(4-Methylphenyl)sulfonyl]-1H-imidazol-2-yl}methanol

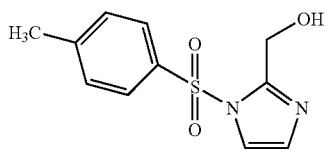

Sodium borohydride (100 mg, 2.6 mmol) was added to a solution of the aldehyde of Preparation 24 (2.55 g, 10.2 mmol) in methanol (15 ml), and the reaction mixture was stirred at room temperature for 18 hours. It was then concentrated under reduced pressure, and the residue was diluted with ethyl acetate (100 ml). The organic layer was washed with water (100 ml), dried over magnesium sulphate and concentrated under reduced pressure. The crude product was azeotroped with diethyl ether to provide the title compound (2.31 g, 92%) as a white solid.

¹H-NMR (400 MHz, CDCl₃): δ=2.44 (s, 3H), 4.85 (s, 2H), 6.98 (s, 1H), 7.36 (m, 3H), 7.83 (d, 2H); LRMS:APCl⁺: m/z 253 [MH⁺]; microanalysis: Found C, 51.73; H, 4.85; N, 10.36%. C₁₁H₁₂N₂O₃S. 0.25 H₂O requires C, 51.46; H, 4.87; N, 10.90%.

Preparation 26: 1-(2-Trimethylsilyl-ethoxymethyl)-1 pyrazole-3/5-carboxaldehyde

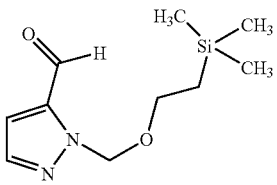

2-(Trimethylsilyl)ethoxymethyl chloride (14 ml, 78 mmol) was added portionwise over 10 minutes, at −40° C., to a solution of pyrazole-3-carboxaldehyde (5 g, 52 mmol) and diisopropylethylamine (13.6 ml, 78 mmol), in dichloromethane (100 ml). The reaction mixture was then warmed to room temperature and stirred for a further 18 hours, after which time it was quenched with brine and extracted with dichloromethane. The organic layer was separated, dried over magnesium sulphate and concentrated under reduced pressure to provide the crude product (14.6 g). A portion of this (3 g) was purified by flash chromatography on silica gel eluting with ethyl acetate:pentane (5:95 to 10:90 to 20:80, by volume) to provide the title compound (14.6 g, 100%) as a 1.1:1 mixture of regioisomers.

¹H-NMR (400 MHz, CDCl₃): δ=−0.05 (s, 9H, regioisomer B), −0.02 (s, 9H, regioisomer A), 0.87-0.94 (m, 2HA+2HB), 3.58 (t, 2HA+2HB), 5.51 (s, 2H, A), 5.81 (s, 2H, B), 6.87 (s, 1H, A), 6.97 (s, 1H, B), 7.62 (m, 1 HA+1 HB), 9.95 (s, 1H, B), 10.01 (s, 1H, A); LC-MS: ESI⁺: m/z 227 [MH⁺].

Preparation 27: [1-(2-Trimethylsilyl-ethoxymethyl)-1H-pyrazol-3/5-yl]methanol

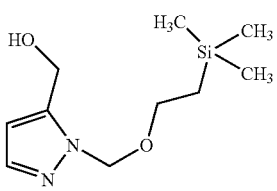

Sodium borohydride (67 mg, 1.76 mmol) was added to a stirred solution of the aldehyde of Preparation 26 (1.33 g, 5.88 mmol) in methanol (30 ml). The reaction mixture was stirred at room temperature for 30 minutes. It was then concentrated under reduced pressure. The residue was taken up in water (100 ml) and extracted with ethyl acetate (2×75 ml). The extracts were combined, dried over magnesium sulphate, filtered and concentrated under reduced pressure to provide the title compound (1.20 g, 89%) as a 1.1:1 mixture of regioisomers A:B.

$^1$H-NMR (400 MHz, CDCl$_3$): δ=−0.03 (s, 9HA+9HB), 0.90 (q, 2HA+2HB), 2.29 (brs, 1HA+1HB), 3.52-3.57 (m, 2HA+2HB), 4.71 (s, 2HA+2HB), 5.38 (s, 2H, A), 5.54 (s, 2H, B), 6.30 (s, 1H, B), 6.32 (s, 1H, A), 7.43 (s, 1H, B), 7.51 (s, 1H, A); LC-MS: ESI+: m/z 229 [MH$^+$].

Preparation 28: 3/5-(Chloromethyl)-1-(2-trimethylsilyl-ethoxymethyl)-1H-pyrazole

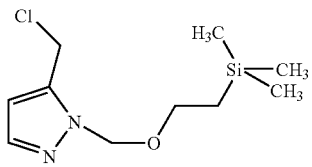

Methanesulphonyl chloride (276 mg, 2.41 mmol) was added to a solution of the pyrazolylmethanol of Preparation 27 (500 mg, 2.19 mmol) and triethylamine (243 mg, 2.41 mmol) in dichloromethane (20 ml). The reaction mixture was stirred at room temperature for 1 hour, and then a further 5 hours until complete conversion of the mesylate to the chloromethyl had as monitored by LCMS. The mixture was then concentrated under reduced pressure. The crude product was purified by flash chromatography on silica gel eluting with ethyl acetate:pentane (10:90, then 20:80 by volume) to provide the title compound (228 mg, 42%) as a 4:1 mixture of regioisomers A:B.

$^1$H-NMR (400 MHz, CDCl$_3$): δ=−0.04 (s, 9HA+9HB), 0.88 (t, 2HA+2HB), 3.54 (t, 2HA+2HB), 4.61 (s, 2H, B), 4.71 (s, 2H, A), 5.38 (s, 2H, B), 5.56 (s, 2H, A), 6.36 (s, 1H, A), 6.39 (s, 1H, B), 7.45 (s, 1H, A), 7.51 (s, 1H, B); LC-MS: ESI$^+$: m/z 247 [MH$^+$].

Preparation 29: 4-[2-Cyclopropyl-1-(cyclopropylcarbonyl)-2-oxoethoxy]benzonitrile

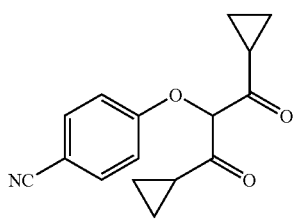

The chlorodiketone described in Preparation 6 (350 g, 1.78 mol) was added to a solution of 2,6-dimethyl-4-hydroxybenzonitrile (254 g, 2.14 mol) and caesium carbonate (697 g, 2.14 mol) in acetone (5.25 L). The reaction mixture was then heated to reflux for 2 hours. After cooling, dichloromethane was added (5.25 L) followed by acetic acid (385 g, 6.42 mol) and water (0.64 L). Following phase separation, the organic phase was washed 3 times with water (1.27 L). The organic phase was then warmed to reflux and 2-propanol (10 L) was added, whilst concentrating the organic phase to remove 10 L of distillate. The product solution was cooled resulting in crystallisation of the product. The slurry was granulated at 0 to 5° C. for one hour, after which time it was collected by filtration and dried overnight. (287 g, 60%)

$^1$H-NMR (300 MHz, CDCl$_3$, enol form): δ=0.87-0.93 (m, 4H), 1.16-1.24 (m, 4H), 1.79-1.84 (m, 2H), 7.13 (d, 2H), 7.66 (d, 2H).

EXAMPLE 1

4-[(3,5-Dimethyl-1H-pyrazol-4-yl)oxy]benzonitrile

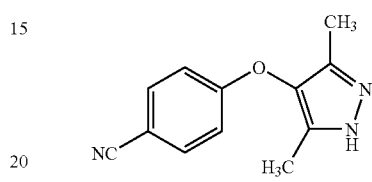

The benzonitrile of Preparation 1 (7.2 g, 33 mmol) was dissolved in acetic acid (70 ml). Hydrazine hydrate (1.9 ml, 39.7 mmol) was then added, and the reaction mixture was stirred at room temperature for 1 hour, under nitrogen. It was then concentrated under reduced pressure, and the residue was purified by flash chromatography on silica gel eluting with dichloromethane:ethyl acetate (3:1 then 1:1, by volume) to provide the title compound (4.09 g, 88%) as a pale yellow solid.

$^1$H-NMR (400 MHz, CDCl$_3$): δ=2.12 (s, 6H), 6.96 (d, 2H), 7.59 (d, 2H); LRMS: ESI$^-$: m/z 212 [M-H]$^-$. Microanalysis: Found: C, 67.48; H, 5.24; N, 19.49%. C$_{12}$H$_{11}$N$_3$O requires C, 67.59; H, 5.20; N, 19.71%.

EXAMPLES 2 & 3

4-(5-Cyclopropyl-3-methyl-1H-pyrazol-4-yloxy)-2, 6-dimethyl-benzonitrile & 4-(5-cyclopropyl-3-methyl-1H-pyrazol-4-yloxy)-2-methyl-benzonitrile

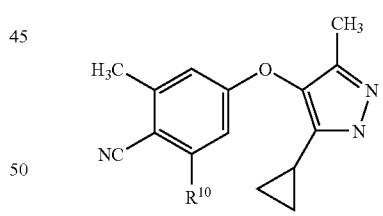

The compounds of the general formula shown above were prepared by a similar method to that described for Example 1 using the appropriate benzonitrile of Preparations 12 and 14 as the starting material.

| Ex No | R$^{10}$ | Analytical Data |
|---|---|---|
| 2 | Me | $^1$H-NMR(400MHz, CDCl$_3$): δ=0.76-0.82(m, 4H), 1.67(m, 1H), 2.08(s, 3H), 2.47(s, 6H), 6.64(s, 2H); LRMS: APCl$^+$: m/z 268[MH$^+$]; APCl$^-$: m/z 266[M−H]$^-$; 62% yield |
| 3 | H | $^1$H-NMR(400MHz, CDCl$_3$): δ=0.77-0.81(m, 4H), 1.66(m, 1H), 2.08(s, 3H), 2.50(s, 3H), 6.77(d, 1H), |

| Ex No | R[10] | Analytical Data |
|---|---|---|
| | | 6.84(s, 1H), 7.52(d, 1H); LRMS: APCl[+]: m/z 254[MH[+]]; APCl[−]: m/z 252[M−H][−]; 71% yield |

EXAMPLE 4

4-[(3,5-Dicyclopropyl-1H-pyrazol-4-yl)oxy]-2,6-dimethylbenzonitrile

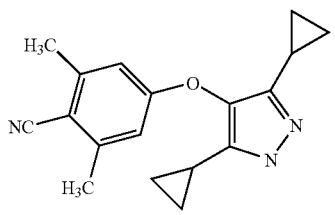

The chlorodiketone of Preparation 6 (13 g, 69.9 mmol) was added to a solution of 2,6-dimethyl-4-hydroxybenzonitrile (13.36 g, 90.9 mmol) and caesium carbonate (29.6 g, 90.8 mmol) in acetone (200 ml). The reaction mixture was then heated at 60° C. for 8 hours. After cooling, it was concentrated under reduced pressure. 2N Hydrochloric acid was added (100 ml) and the mixture was then extracted with dichloromethane (150 ml). The organic layers were separated, washed with brine, dried over magnesium sulphate, filtered and concentrated under reduced pressure to give crude diketone intermediate (22 g, ~90% pure, ~65 mmol). A portion of this (19 g) was added to a solution of hydrazine hydrate (4 ml, 82.3 mmol) in acetic acid (200 ml) and ethanol (50 ml). The reaction mixture was stirred at room temperature for 18 hours under nitrogen, and then concentrated under reduced pressure. Water (100 ml) was added, and the mixture was extracted with dichloromethane (2×150 ml). The combined organic layers were dried over magnesium sulphate, filtered and concentrated under reduced pressure. The crude product was purified by flash chromatography on silica gel eluting with ethyl acetate:pentane (20:80, by volume) to provide the title compound (14 g, 68%).

$^1$H-NMR (400 MHz, CDCl$_3$): δ=0.75-0.81 (m, 8H), 1.60-1.66 (m, 2H), 2.48 (s, 6H), 6.67 (s, 2H); LRMS: APCl[+]: m/z 294 [MH[+]]; APCl[−]: m/z 292 [M−H][−].

EXAMPLES 5-14

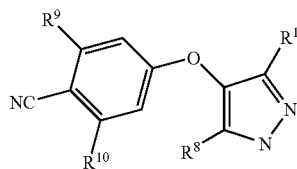

Compounds of the general formula given above were prepared by a similar method to that described for Example 4 using the appropriate chlorodiketone and phenol as the starting materials (available commercially, or described as Preparations 2 to 4, 6, and 9 to 10).

| Ex No | R[9]; R[10]; R[8]; R[1] Analytical Data |
|---|---|
| 5 | R[9]=H; R[10]=H; R[8]=Et; R[1]=Et<br>$^1$H-NMR(400MHz, CDCl$_3$): δ=1.14(t, 6H), 2.48(q, 4H), 6.95(d, 2H), 7.58(d, 2H), 10.31(brs, 1H); LRMS: APCl[+]: m/z 242[MH[+]]; APCl[−]: m/z 240[M−H][−]; 85% yield |
| 6 | R[9]=Me; R[10]=Me; R[8]=Me; R[1]=Me<br>$^1$H-NMR(400MHz, CDCl$_3$): δ=2.12(s, 6H), 2.47(s, 6H), 6.62(s, 2H); LRMS: APCl[+]: m/z 242[MH[+]]; APCl[−]: m/z 240[M−H][−]; Microanalysis: Found: C, 69.32; H, 6.30; N, 17.23%. C$_{14}$H$_{15}$N$_3$O requires C, 69.71; H, 6.22; N, 17.43%; 55% yield |
| 7 | R[9]=H; R[10]=H; R[8]=cPr; R[1]=cPr<br>$^1$H-NMR(400MHz, CDCl$_3$): δ=0.76-0.81(m, 8H), 1.59-1.65(m, 2H), 7.01(d, 2H), 7.60(d, 2H); LRMS: APCl[+]: m/z 266[MH[+]]; APCl[−]: m/z 264[M−H][−]; 65% yield |
| 8 | R[9]=Me; R[10]=Me; R[8]=Et; R[1]=Et<br>$^1$H-NMR(400MHz, CDCl$_3$): δ=1.17(t, 6H), 2.47-2.50(m, 10H), 6.62(s, 2H); LRMS: APCl[+]: m/z 270[MH[+]]; APCl[−]: m/z 268[M−H][−]; Microanalysis: Found: C, 69.95; H, 7.41; N, 15.89%. C$_{16}$H$_{19}$N$_3$O. 0.2H$_2$O requires C, 70.41; H, 7.26; N, 15.41%; 49% yield |
| 9 | R[9]=OMe; R[10]=H; R[8]=Et; R[1]=Et<br>$^1$H-NMR(400MHz, CDCl$_3$): δ=1.18(t, 6H), 2.52(q, 4H), 3.87(s, 3H), 6.45(d, 1H), 6.53(s, 1H), 7.44(d, 1H); LRMS: APCl[+]: m/z 272[MH[+]]; APCl[−]: m/z 270[M−H][−]; Microanalysis: Found: C, 66.17; H, 6.35; N, 15.36%. C$_{15}$H$_{17}$N$_3$O$_2$ requires C, 66.42; H, 6.27; N, 15.50%; 64% yield |
| 10 | R[9]=H; R[10]=H; R[8]=Me; R[1]=cPr<br>$^1$H-NMR(400MHz, CDCl$_3$): δ=0.74-0.81(m, 4H), 1.66(m, 1H), 2.06(s, 3H), 6.96(d, 2H), 7.59(d, 2H), 9.80(brs, 1H); LRMS: APCl[+]: m/z 240[MH[+]]; APCl[−]: m/z 238[M−H][−]; 33% yield |
| 11 | R[9]=CN; R[10]=H; R[8]=Et; R[1]=Et<br>$^1$H-NMR(400MHz, CDCl$_3$): δ=1.16(t, 6H), 2.48(q, 4H), 7.24(d, 1H), 7.29(s, 1H), 7.73(d, 1H); LRMS: APCl[+]: m/z 267[MH[+]]; APCl[−]: m/z 265[M−H][−]; 65% yield |
| 12 | R[9]=CF$_3$; R[10]=H; R[8]=cPr; R[1]=cPr<br>$^1$H-NMR(400MHz, CDCl$_3$): δ=0.74-0.77(m, 4H), 0.81-0.85(m, 4H), 1.57-1.64(m, 2H), 7.17(d, 1H), 7.37(s, 1H), 7.77(d, 1H); LRMS: APCl[+]: m/z 334[MH[+]]; APCl[−]: m/z 332[M−H][−]; 54% yield |

-continued

| Ex No | R⁹; R¹⁰; R⁸; R¹<br>Analytical Data |
|---|---|
| 13 | $R^9$=Me; $R^{10}$=H; $R^8$=cPr; $R^1$=cPr<br>¹H-NMR(400MHz, CDCl₃): δ=0.75-0.86(m, 8H), 1.59-1.66(m, 2H), 2.51(s, 3H),<br>6.81(d, 1H), 6.87(s, 1H), 7.52(d, 1H); LRMS: APCl⁺: m/z 280[MH⁺]; APCl⁻:<br>m/z 278[M−H]⁻; 26% yield |
| 14 | $R^9$=Cl; $R^{10}$=H; $R^8$=cPr; $R^1$=cPr<br>¹H-NMR(400MHz, CDCl₃): δ=0.76-0.79(m, 4H), 0.82-0.85(m, 4H),<br>1.59-1.64(m, 2H), 6.93(d, 1H), 7.07(s, 1H), 7.55(brs, 1H), 7.60(d, 1H); LRMS: APCl⁺:<br>m/z 300[MH⁺]; APCl⁻: m/z 298[M−H]⁻; Microanalysis: Found C 64.16, H 4.79, N<br>13.81%. C₁₆H₁₄N₃ClO requires C 64.21, H 4.68, N 14.05%; 52% yield |

EXAMPLE 15

4-[(3-Ethyl-3-methoxy-1H-pyrazol-4-yl)oxy]benzonitrile

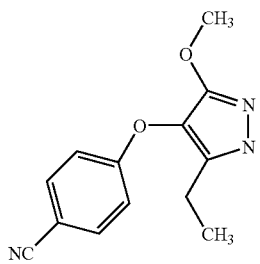

The pyrazole carboxylate of Preparation 17 (88 mg, 0.26 mmol) was dissolved in dichloromethane (3 ml) and trifluoroacetic acid (3 ml), and stirred at room temperature for 1 hour. The reaction mixture was then evaporated, and the residue was partitioned between dichloromethane (5 ml) and a saturated solution of aqueous sodium bicarbonate (5 ml). The organic layer was separated and the aqueous layer was extracted twice more with dichloromethane (2×5 ml). The organic extracts were combined, dried over magnesium sulphate, filtered and evaporated to give a solid product, which was triturated in pentane to give the title compound as a white solid (55 mg, 88%).

¹H-NMR (400 MHz, CDCl₃): δ=1.18 (t, 3H), 2.55 (q, 2H), 3.90 (s, 3H), 7.01 (d, 2H), 7.59 (d, 2H); LRMS:APCl⁺: m/z 244 [MH⁺]; APCl⁻: m/z 242 [M−H]⁻; Microanalysis: Found C, 63.28, H, 5.33, N, 17.08%. C₁₃H₁₃N₃O₂ requires C, 64.19; H, 5.39; N, 17.27%.

EXAMPLE 16

4-[(3-Cyclopropyl-1H-pyrazol-4-yl)oxy]-2,6-dimethylbenzonitrile

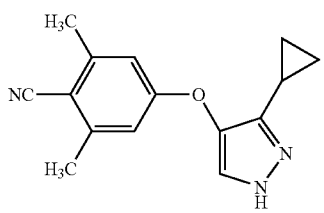

The benzonitrile of Preparation 20 (11.19 g, 39.3 mmol) was dissolved in acetic acid (62 ml). Hydrazine hydrate (2.11 ml, 43.6 mmol) was added, and the mixture was stirred at room temperature for 12 hours, under nitrogen. The reaction mixture was then concentrated under reduced pressure, and the residue was partitioned between water (100 ml) and diethyl ether (150 ml). The organic layer was dried over magnesium sulphate, filtered and concentrated under reduced pressure to provide the title compound (9.71 g, 98%) as a solid.

¹H-NMR (400 MHz, CDCl₃): δ=0.82-0.88 (m, 4H), 1.73 (m, 1H), 2.47 (s, 6H), 6.70 (s, 2H), 7.41 (s, 1H), 10.5 (brs, 1H); LRMS:APCl⁺: m/z 254 [MH⁺]; APCl⁻: m/z 252 [M−H]⁻

EXAMPLE 17

4-{[1-(2-Hydroxyethyl)-3,5-dimethyl-1H-pyrazol-4-yl]oxy}benzonitrile

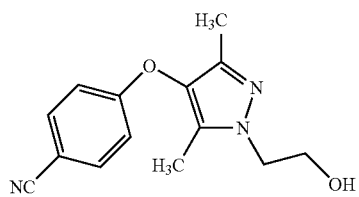

A mixture of commercially available 3-chloro-2,4-pentanedione (1.2 ml, 10 mmol), 4-cyanophenol (1.19 g, 10 mmol), caesium carbonate (3.25 g, 10 mmol) and acetone (50 ml) was heated at 60° C. for 4 hours. After cooling, the reaction mixture was concentrated under reduced pressure. The resulting oil was diluted with dichloromethane (25 ml) and washed with 1M hydrochloric acid (30 ml). The aqueous layer, at pH 1, was extracted with dichloromethane (20 ml). The combined organic extracts were washed with brine, dried over magnesium sulphate, filtered and concentrated under reduced pressure to provide 4-(1-acetyl-2-oxopropoxy)benzonitrile (2.06 g, 9.4 mmol) which was used crude in the next step. 2-Hydroxyethyl hydrazine (169 µL, 2.5 mmol) was added to a stirred solution of a portion of the crude 4-(1- acetyl-2-oxopropoxy)benzonitrile (500 mg, 2.3 mmol) in acetic acid (5 ml) at room temperature under nitrogen, and the mixture was stirred at room temperature for 5 hours. Water (20 ml) was then added, and a solid triturated out and filtered off. This was recrystallised from ethyl acetate to provide the title compound (154 mg, 6%).

$^1$H-NMR (400 MHz, CDCl$_3$): δ=2.05 (s, 3H), 2.10 (s, 3H), 4.02-4.04 (m, 2H), 4.06-4.10 (m, 2H), 6.95 (d, 2H), 7.58 (d, 2H); LRMS: APCI$^+$: m/z 258 [MH$^+$]; LCMS (220 nm and 254 nm) single peak m/z 258 [MH$^+$]; Microanalysis: Found: C, 65.16; H, 5.85; N, 16.29%. C$_{14}$H$_{15}$N$_3$O$_2$ requires C, 65.36; H, 5.88; N, 16.33%.

EXAMPLES 18-27

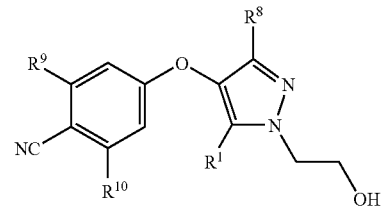

The compounds of the general formula given above were prepared by a similar method to that described for Example 17, using the appropriate diketone and phenol (available commercially or from the relevant Preparations (2 and 10) as the starting materials.

| Ex No | R$^9$; R$^{10}$; R$^8$; R$^1$<br>Analytical Data |
|---|---|
| 18 | R9=Cl; R10=H; R8=Me; R1=Me<br>$^1$H-NMR(400MHz, CDCl$_3$): δ=2.05(s, 3H), 2.10(s, 3H), 4.02-4.04(m, 2H), 4.07-4.09(m, 2H), 6.70(d, 1H), 6.79(d, 1H), 7.53(t, 1H); LRMS: APCI$^+$: m/z 276[MH$^+$]; LCMS (220nm and 254nm) single peak m/z 276[MH$^+$]; Microanalysis: Found: C, 61.00; H, 5.13; N, 15.15%. C$_{14}$H$_{14}$FN$_3$O$_2$ requires C, 61.08; H, 5.13; N, 15.26%; 8% yield |
| 19 | R$^9$=Cl; R$^{10}$=H; R$^8$=Me; R$^1$=Me<br>$^1$H-NMR(400MHz, CDCl$_3$): δ=2.04(s, 3H), 2.10(s, 3H), 4.04-4.07(m, 4H), 6.87(d, 1H), 6.99(s, 1H), 7.58(d, 1H); LRMS: APCI$^+$: m/z 292[MH$^+$]; LCMS(220nm and 254nm) single peak m/z 292[MH$^+$]; Microanalysis: Found: C, 57.09; H, 4.85; N, 14.00%. C$_{14}$H$_{14}$ClN$_3$O$_2$ requires C, 57.64; H, 4.84; N, 14.40%; 18.5% yield |
| 20 | R$^9$=CN; R$^{10}$=H; R$^8$=Me; R$^1$=Me<br>$^1$H-NMR(400MHz, CDCl$_3$): δ=2.03(s, 3H), 2.10(s, 3H), 4.05-4.08(m, 4H), 7.21-7.25(m, 2H), 7.72(d, 1H); LRMS:APCI$^+$: m/z 283[MH$^+$]; LCMS(220nm and 254nm) single peak m/z 283[MH$^+$]; Microanalysis: Found: C, 63.46; H, 5.02; N, 19.65%. C$_{15}$H$_{14}$N$_4$O$_2$ requires C, 63.82; H, 5.00; N, 19.85%; 20.5% yield |
| 21 | R$^9$=H; R$^{10}$=H; R$^8$=Et; R$^1$=Et<br>$^1$H-NMR(400MHz, CDCl$_3$): δ=1.08(t, 3H), 1.12(t, 3H), 2.40(q, 2H), 2.51(q, 2H), 3.66(brs, 1H), 4.02-4.09(m, 4H), 6.97(d, 2H), 7.58(d, 2H); LRMS: APCI$^+$: m/z 286[MH$^+$]; Microanalysis: Found: C, 66.94; H, 6.77; N, 14.60%. C$_{16}$H$_{19}$N$_3$O$_2$ requires C, 67.35; H, 6.71; N, 14.73%; Mp=82° C.; 12% yield |
| 22 | R$^9$=F; R$^{10}$=H; R$^8$=Et; R$^1$=Et<br>$^1$H-NMR(400MHz, CDCl$_3$): δ=1.07-1.15(m, 6H), 2.41(q, 2H), 2.51(q, 2H), 3.58(brs, 1H), 4.04-4.09(m, 4H), 6.71(dd, 1H), 6.80(dd, 1H), 7.53(t, 1H); LRMS: APCI$^+$: m/z 304[MH$^+$]; APCI$^-$: m/z 302[M–H]$^-$; Microanalysis: Found: C, 62.95; H, 6.10; N, 13.62%. C$_{16}$H$_{18}$FN$_3$O$_2$, 0.13H$_2$O requires C, 62.87; H, 6.02; N, 13.75%; 11% yield |
| 23 | R$^9$=Cl; R$^{10}$=H; R$^8$=Et; R$^1$=Et<br>$^1$H-NMR(400MHz, CDCl$_3$): δ=1.04-1.12(m, 6H), 2.38(q, 2H), 2.48(q, 2H), 3.57(brs, 1H), 4.02-4.06(m, 4H), 6.85(d, 1H), 6.99(s, 1H), 7.54(d, 1H); LRMS: APCI$^+$: m/z 320[MH$^+$]; APCI$^-$: m/z 318[M–H]$^-$; Microanalysis: Found: C, 59.93; H, 5.74; N, 12.91%. C$_{16}$H$_{18}$ClN$_3$O$_2$ requires C, 60.09; H, 5.67; N, 13.14%; Mp=85° C.; 20% yield |
| 24 | R$^9$=Me; R$^{10}$=H; R$^8$=Et; R$^1$=Et<br>$^1$H-NMR(400MHz, CDCl$_3$): δ=1.07-1.15(m, 6H), 2.41(q, 2H), 2.48-2.52(m, 5H), 4.03-4.06(m, 2H), 4.09-4.11(m, 2H), 6.76(d, 1H), 6.83(s, 1H), 7.51(d, 1H); LRMS: APCI$^+$: m/z 300[MH$^+$]; Microanalysis: Found: C, 66.12; H, 7.19; N, 13.52%. C$_{17}$H$_{21}$N$_3$O$_2$.0.5H$_2$O requires C, 66.23; H, 7.14; N, 13.63%; 40% yield |
| 25 | R$^9$=CN; R$^{10}$=H; R$^8$=Et; R$^1$=Et<br>$^1$H-NMR(400MHz, CDCl$_3$): δ=1.07-1.14(m, 6H), 2.39(q, 2H), 2.51(q, 2H), 4.06-4.10(m, 4H), 7.23(d, 1H), 7.29(s, 1H), 7.72(d, 1H); LRMS: APCI$^+$: m/z 311[MH$^+$]; 44% yield |
| 26 | R$^9$=OMe; R$^{10}$=H; R$^8$=Et; R$^1$=Et<br>$^1$H-NMR(400MHz, CDCl$_3$): δ=1.07-1.16(m, 6H), 2.42(q, 2H), 2.52(q, 2H), 3.88(s, 3H), 4.03-4.06(m, 2H), 4.08-4.11(m, 2H), 6.42(d, 1H), 6.54(s, 1H), 7.44(d, 1H); LRMS: APCI$^+$: m/z 316[MH$^+$]; Microanalysis: Found: C, 63.55; H, 6.85; N, 13.02%. C$_{17}$H$_{21}$N$_3$O$_3$.0.25H$_2$O requires C, 63.84; H, 6.73; N, 13.14%; 55% yield |
| 27 | R$^9$=Me; R$^{10}$=Me; R$^8$=Et; R$^1$=Et<br>$^1$H-NMR(400MHz, CDCl$_3$): δ=1.03(t, 3H), 1.13(t, 3H), 2.41(q, 2H), 2.47-2.51(m, 5H), 3.72(brs, 1H), 4.05-4.09(m, 4H), 6.62(s, 2H); LRMS: APCI$^+$: m/z 314[MH$^+$]; Microanalysis: Found: C, 68.51; H, 7.46; N, 13.19%. C$_{18}$H$_{23}$N$_3$O$_2$ requires C, 68.98; H, 7.40; N, 13.41%; Mp=97° C.; 11% yield |

EXAMPLE 28

4-{[3,5-Dicyclopropyl-1-(2-hydroxyethyl)-1 pyrazol-4-yl]oxy}-2,6-dimethylbenzonitrile

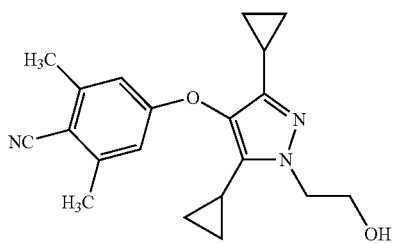

2-Hydroxyethyl hydrazine (64 μl, 0.92 mmol) was added to a stirred solution of the benzonitrile of Preparation 13 (250 mg, 0.84 mmol) in ethanol (5 ml) and acetic acid (20 ml) at room temperature, under nitrogen. The resulting solution was stirred at room temperature for 18 hours, and then heated at 50° C. for 4 hours. After cooling, the mixture was concentrated under reduced pressure. The residue was dissolved in dichloromethane (20 ml). The organic layer was washed with 2M hydrochloric acid (10 ml) and brine (10 ml), dried over magnesium sulphate, filtered and concentrated under reduced pressure. The crude product was purified by flash chromatography on silica gel eluting with pentane:ethyl acetate (1:1 to 1:2, by volume) to provide the title compound (200 mg, 71%).

$^1$H-NMR (400 MHz, CDCl$_3$): δ=0.66-0.70 (m, 2H), 0.75-0.73 (m, 6H), 1.48-1.57 (m, 2H), 2.48 (s, 6H), 4.03 (t, 2H), 4.20 (t, 2H), 6.64 (s, 2H); LRMS: APCl$^+$: m/z 338 [MH$^+$]; Microanalysis: Found: C, 71.02; H, 6.89; N, 12.45%. C$_{20}$H$_{23}$N$_3$O$_2$ requires C, 71.19; H, 6.67; N, 12.45%.

EXAMPLES 29 & 30

4-{[3-Cyclopropyl-1-(2-hydroxyethyl)-5-methyl-1 pyrazol-4-yl]oxy}-2,6-dimethylbenzonitrile and 4-{[5-cyclopropyl-1-(2-hydroxyethyl)-3-methyl-1H-pyrazol-4-yl]oxy}-2,6-dimethylbenzonitrile

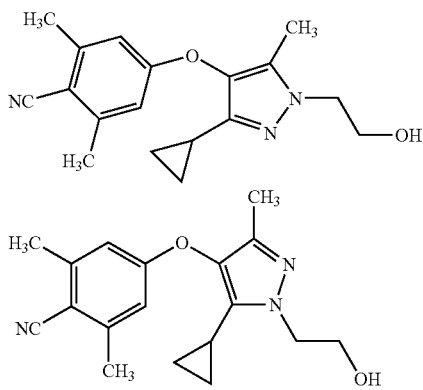

Examples 29 and 30 were prepared by a similar method to that described for Example 28 using the benzonitrile of Preparation 12 and 2-hydroxyethyl hydrazine as starting materials. The residue containing the two regioisomers, as identified by TLC analysis, was purified by flash chromatography on silica gel eluting with ethyl acetate:pentane (1:9 to 1:2 to 1:1, by volume). Example 29 was isolated first (360 mg, 62%).

$^1$H-NMR (400 MHz, CDCl$_3$): δ=0.76-0.80 (m, 4H), 1.61 (m, 1H), 2.06 (s, 3H), 2.48 (s, 6H), 4.00-4.06 (m, 4H), 6.64 (s, 2H); LRMS:APCl$^+$: m/z 312 [MH$^+$]; Microanalysis: Found: C, 69.19; H, 6.79; N, 13.41%. C$_{18}$H$_{21}$N$_3$O$_2$ requires C, 69.43; H, 6.80; N, 13.49%.

Further elution provided Example 30 (120 mg, 21%).

$^1$H-NMR (400 MHz, CDCl$_3$): δ=0.67-0.71 (m, 2H), 0.81-0.85 (m, 2H), 1.55 (m, 1H), 2.01 (s, 3H), 2.48 (s, 6H), 4.07 (t, 2H), 4.26 (t, 2H), 6.59 (s, 2H); LRMS: APCl$^+$: m/z 312 [MH$^+$].

The structures were confirmed by $^1$H—$^{13}$C NMR correlations.

EXAMPLE 34

4-{[3,5-Diethyl-1-(2-methoxyethyl)-1H-pyrazol-4-yl]oxy}-2,6-dimethylbenzonitrile

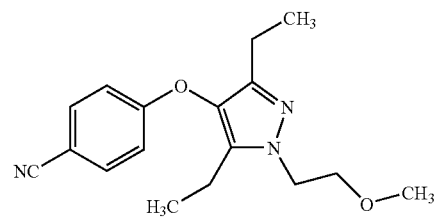

Sodium hydride (60% dispersion in oil, 33.4 mg, 0.79 mmol) was added to a stirred solution of the benzonitrile of Example 5 (200 mg, 0.83 mmol) in dry N,N-dimethylformamide (25 ml) at 0° C., under nitrogen. The reaction mixture was stirred at 0° C. for 10 minutes, and then 1-bromo-2methoxyethane (86 μL, 0.91 mmol) was added. The reaction mixture was stirred at room temperature for a further 18 hours. Water (100 ml) was then added and the mixture was extracted with dichloromethane (50 ml). The organic layers were separated, dried over magnesium sulphate, filtered and concentrated under reduced pressure. The crude product was purified by flash chromatography on silica gel eluting with ethyl acetate:pentane (30:70, by volume) to provide the title compound (80 mg, 32%).

$^1$H-NMR (400 MHz, CDCl$_3$): δ=1.08 (q5, 6H), 2.40 (q, 2H), 2.52 (q, 2H), 3.31 (s, 3H), 3.73 (t, 2H), 4.14 (t, 2H), 6.95 (d, 2H), 7.56 (d, 2H); LRMS: APCl$^+$: m/z 300 [MH$^+$].

EXAMPLE 35

Ethyl[4-(4-cyanophenoxy)-3,5-diethyl-1H-pyrazol-1-yl]acetate

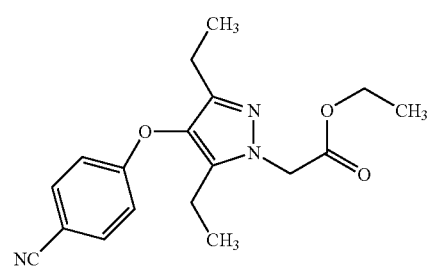

Sodium ethoxide (21% w/w solution in ethanol, 2.95 g, 9.13 mmol) was added to a stirred solution of the benzonitrile of Example 5 (2 g, 8.3 mmol) in ethanol (50 ml). After stirring for 10 minutes, ethyl bromoacetate (1 ml, 9.1 mmol) was added and the reaction mixture was stirred at room temperature for a further 18 hours. More sodium ethoxide (2.95 g, 9.13 mmol) was added, followed by ethyl bromoacetate (1 ml, 9.1 mmol) and the reaction mixture was then heated at reflux for 18 hours. Water (50 ml) was added and the mixture was evaporated under reduced pressure. The residue was partitioned between dichloromethane (100 ml) and water (50 ml). The organic layer was dried over magnesium sulphate, filtered and concentrated under reduced pressure. The crude product was purified by flash chromatography on silica gel eluting with ethyl acetate:pentane (30:70, by volume) to provide the title compound (1.25 g, 46%).

$^1$H-NMR (400 MHz, CDCl$_3$): δ=1.05-1.13 (m, 6H), 1.29 (t, 3H), 2.38-2.49 (m, 4H), 4.24 (q, 2H), 4.80 (s, 2H), 6.98 (d, 2H), 7.58 (d, 2H); LRMS: APCl$^+$: m/z 328 [MH$^+$].

Potassium carbonate (52 g, 380 mmol), followed by ethyl bromoacetate (23 ml, 208 mmol), was added to a stirred solution of the benzonitrile of Example 7 (50 g, 189 mmol) in dry 1,2-dimethoxyethane (600 ml), at room temperature, under nitrogen. The reaction mixture was then heated at 85° C. for 20 hours. Additional ethyl bromoacetate (5 ml, 45 mmol) was added, and the reaction was then continued at 85° C. for a further 4 hours. The reaction mixture was then cooled, filtered and evaporated to give an oil which was shaken with pentane (500 ml) and left to crystallise. The pentane was then decanted off, to provide the title compound (73 g, ~100%).

$^1$H-NMR (400 MHz, CDCl$_3$): δ=0.64-0.67 (m, 2H), 0.73-0.79 (m, 6H), 1.29 (t, 3H), 1.43 (m, 1H), 1.57 (m, 1H), 4.24 (q, 2H), 4.86 (s, 2H), 7.00 (d, 2H), 7.59 (d, 2H); LRMS: APCl$^+$: m/z 352 [MH$^+$].

EXAMPLE 36

Ethyl[4-(4-cyanophenoxy)-3,5-dicyclopropyl-1H-pyrazol-1-yl]acetate

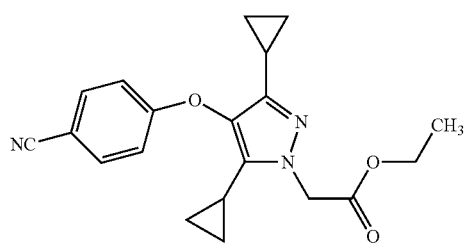

EXAMPLES 37-43

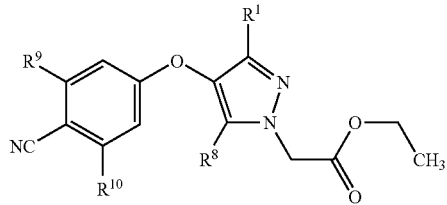

The compounds of the general formula given above were prepared by a similar method to that described for Example 36 using the appropriate pyrazole and bromoacetate ester as the starting materials.

| Ex No | $R^9$; $R^{10}$; $R^8$; $R^1$ <br> Analytical Data |
|---|---|
| 37 (from Ex 6) | $R^9$=Me; $R^{10}$=Me; $R^8$=Me; $R^1$=Me <br> $^1$H-NMR(400MHz, CDCl$_3$): δ=1.29(t, 3H), 2.04(s, 6H), 2.46(s, 6H), 4.24(q, 2H), 4.77(s, 2H), 6.62(s, 2H); LRMS: APCl$^+$: m/z 328[MH$^+$]; Microanalysis: Found: C, 64.67; H, 6.39; N, 12.22%. C$_{18}$H$_{21}$N$_3$O$_3$ requires C, 66.04; H, 6.47; N, 12.84%; 79% yield |
| 38 (from Ex 4) | $R^9$=Me; $R^{10}$=Me; $R^8$=cPr; $R^1$=cPr <br> $^1$H-NMR(400MHz, CDCl$_3$): δ=0.65-0.68(m, 2H), 0.77-0.79(m, 6H), 1.29(t, 3H), 1.44(m, 1H), 1.57(m, 1H), 2.48(s, 6H), 4.24(q, 2H), 4.87(s, 2H), 6.66(s, 2H); LRMS: APCl$^+$: m/z 380[MH$^+$]; 100% |
| 39 (from Ex 8) | $R^9$=Me; $R^{10}$=Me; $R^8$=Et; $R^1$=Et <br> $^1$H-NMR(400MHz, CDCl$_3$): δ=1.08-1.13(m, 6H), 1.29(t, 3H), 2.41-2.47(m, 10H), 4.24(q, 2H), 4.80(s, 2H), 6.64(s, 2H); LRMS: APCl$^+$: m/z 356[MH$^+$]; 76% yield |
| 40 (from Ex 12) | $R^9$=H; $R^{10}$=CF3; $R^8$=cPr; $R^1$=cPr <br> $^1$H-NMR(400MHz, CDCl$_3$): δ=0.63-0.67(m, 2H), 0.75-0.81(m, 6H), 1.24-1.31(m, 3H), 1.43(m, 1H), 1.54(m, 1H), 4.12(q, 2H), 4.18(q, 2H), 4.87(s, 2H), 7.15(d, 1H), 7.38(s, 1H), 7.77(d, 1H). (contaminated with ethylbromoacetate); LRMS: APCl$^+$: m/z 420[MH$^+$]; 100% yield |
| 41 (from Ex13) | $R^9$=H; $R^{10}$=Me; $R^8$=cPr; $R^1$=cPr <br> $^1$H-NMR(400MHz, CDCl$_3$): δ=0.65-0.67(m, 2H), 0.73-0.79(m, 6H), 1.26-0.32(m, 3H), 1.44(m, 1H), 1.54(m, 1H), 2.51(s, 3H), 4.21-4.25(m, 2H), 4.86(s, 2H), 6.77(d, 1H), 6.86(s, 1H), 7.52(d, 1H). (contaminated with ethylbromoacetate); LRMS: APCl$^+$: m/z 366[MH$^+$]; 100% yield |
| 42 (from Ex 16) | $R^9$=Me; $R^{10}$=Me; $R^8$=H; $R^1$=cPr <br> $^1$H-NMR(400MHz, CDCl$_3$): δ=0.76-0.82(m, 4H), 1.28(t, 3H), 1.62(m, 1H), 2.46(s, 6H), 4.23(q, 2H), 4.77(s, 2H), 6.71(s, 2H), 7.29(s, 1H); LRMS: APCl$^+$: m/z 340[MH$^+$]; 97% yield |
| 43 (from Ex 14) | $R^9$=Cl; $R^{10}$=H; $R^8$=cPr; $R^1$=cPr <br> $^1$H-NMR(400MHz, CDCl$_3$): δ=0.64-0.68(m, 2H), 0.75-0.79(m, 6H), 1.30(t, 3H), 1.44(m, 1H), 1.56(m, 1H), 4.24(q, 2H), 4.87(s, 2H), 6.92(d, 1H), 7.07(s, 1H), 7.59(d, 1H); LRMS: APCl$^+$: m/z 386[MH$^+$]; 100% yield |

EXAMPLES 44-47

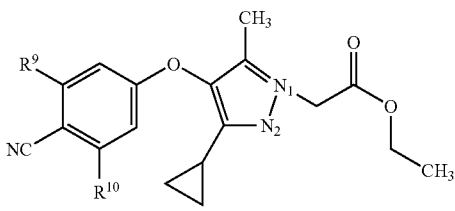

Compounds, of the general formula given above, were prepared by a similar method to that described for Example 36, using the benzonitriles of Example 10 and Example 3, along with ethyl bromoacetate as the starting materials. For each case, purification of the residue containing the two regioisomers (as identified by TLC) by flash chromatography on silica gel eluting with ethyl acetate:cyclohexane (20:80, by volume then 25:75) provided first the N1 alkylated compound then further elution provided the N2 alkylated compound.

| Ex No | N alkyl$^n$ | $R^9$; $R^{10}$ Analytical Data |
|---|---|---|
| 44 | N1 | $R^9$=H; $R^{10}$=H<br>$^1$H-NMR(400MHz, CDCl$_3$): δ=0.74-0.78(m, 4H), 1.29(t, 3H), 1.61(m, 1H), 2.03(s, 3H), 4.24(q, 2H), 4.75(s, 2H), 7.00(d, 2H), 7.59(d, 2H); LRMS: APCl$^+$: m/z 326[MH$^+$]; 60% yield |
| 45 | N2 | $R^9$=H; $R^{10}$=H<br>$^1$H-NMR(400MHz, CDCl$_3$): δ=0.66-0.69(m, 2H), 0.75-0.79(m, 2H), 1.31(t, 3H), 1.47(m, 1H), 2.02(s, 3H), 4.26(q, 2H), 4.90(s, 2H), 6.96(d, 2H), 7.59(d, 2H), contaminated by the other regioisomer; LRMS: APCl$^+$: m/z 326[MH$^+$]; 47% yield |
| 46 | N1 | $R^9$=H; $R^{10}$=Me<br>$^1$H-NMR(400MHz, CDCl$_3$): δ=0.74-0.79(m, 4H), 1.29(t, 3H), 1.61(m, 1H), 2.02(s, 3H), 2.50(s, 3H), 4.23(q, 2H), 4.75(s, 2H), 6.79(d, 1H), 6.86(s, 1H), 7.52(d, 1H); LRMS: APCl$^+$: m/z 340[MH$^+$]. |
| 47 | N2 | $R^9$=H; $R^{10}$=Me<br>$^1$H-NMR(400MHz, CDCl$_3$): δ=0.67-0.70(m, 2H), 0.76-0.79(m, 2H), 1.31(t, 3H), 1.47(m, 1H), 2.02(s, 3H), 2.50(s, 3H), 4.26(q, 2H), 4.90(s, 2H), 6.75(d, 1H), 6.82(s, 1H), 7.51(d, 1H), contaminated by the other regioisomer; LRMS: APCl$^+$: m/z 340[MH$^+$]. |

EXAMPLES 48-49

Ethyl[4-(4-cyano-3,5-dimethylphenoxy)-3-cyclopropyl-5-methyl-1H-pyrazol-1-yl]acetate and ethyl[4-(4-cyano-3,5-dimethylphenoxy)-5-cyclopropyl-3-methyl-1H-pyrazol-1-yl]acetate

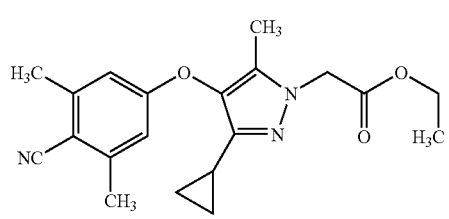

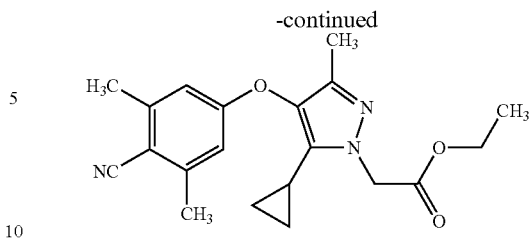

Ethyl hydrazinoacetate hydrochloride (11.26 g, 8.15 mmol) was added to a stirred solution of the benzonitrile of Preparation 12 (2 g, 7.38 mmol), in ethanol (10 ml) and acetic acid (30 ml), at room temperature, under nitrogen, and the resulting solution was stirred at room temperature for 18 hours. The reaction mixture was then concentrated under reduced pressure, and the residue was dissolved in dichloromethane (20 ml). The organic layer was washed with water, dried over magnesium sulphate, filtered and concentrated under reduced pressure. The crude mixture containing the 2 regioisomers was purified by flash chromatography on silica gel eluting with pentane:ethyl acetate (80:20 to 50:50, by volume) to provide Example 48 (90 mg, 4%) eluted first.

$^1$H-NMR (400 MHz, CDCl$_3$): δ=0.75-078 (m, 4H), 1.29 (t, 3H), 1.61 (m, 1H), 2.02 (s, 3H), 2.48 (s, 6H), 4.23 (q, 2H), 4.75 (s, 2H), 6.66 (s, 2H); LRMS: APCl$^+$: m/z 354 [MH$^+$].

Further elution provided Example 49 (1.15 g, 44%).

$^1$H-NMR (400 MHz, CDCl$_3$): δ=0.66-0.69 (m, 2H), 0.76-0.80 (m, 2H), 1.30 (t, 3H), 1.47 (m, 1H), 2.01 (s, 3H), 2.47 (s, 6H), 4.25 (q, 2H), 4.90 (s, 2H), 6.61 (s, 2H); LRMS:APCl$^+$: m/z 354 [MH$^+$]; Microanalysis: Found: C, 67.88; H, 6.56; N, 11.87%. C$_{20}$H$_{23}$N$_3$O$_3$ requires C, 67.97; H, 6.56; N, 11.86%.

The structures were confirmed by $^1$H—$^{13}$C NMR correlations.

EXAMPLES 50-51

Ethyl 2-[4-(4-cyanophenoxy)-3,5-diethyl-1-pyrazol-1-yl]-2-methylpropanoate and methyl 2-[4-(4-cyanophenoxy)-3,5-diethyl-1H-pyrazol-1-yl]-2-methylpropanoate

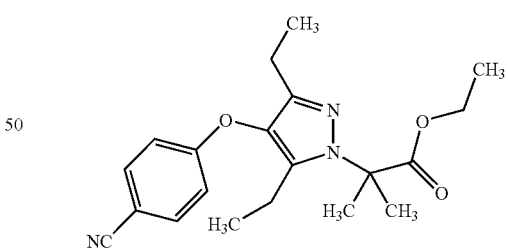

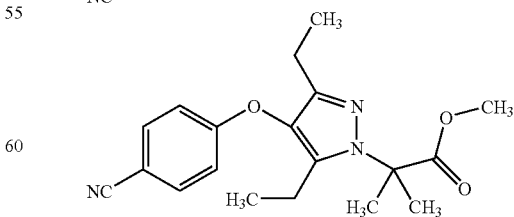

Sodium hydride (60% dispersion in oil, 123 mg, 3.21 mmol) was added to a stirred solution of Example 35 (350 mg, 1.07 mmol) in dry N,N-dimethylformamide (5 ml) under nitrogen. The reaction mixture was stirred for 30 minutes at room temperature, during which time hydrogen was evolved, and then methyl iodide (1.1 ml, 3.21 mmol) was added. The reaction mixture was quenched by the addition of water (25 ml), concentrated under reduced pressure and then dichloromethane was added (50 ml). The organic layer was separated, dried over magnesium sulphate and concentrated under reduced pressure. The residue containing two products was purified by flash chromatography on silica gel eluting with ethyl acetate:pentane (1:2 to 1:1, by volume) to provide Example 50 (125 mg, 33%) first.

$^1$H-NMR (400 MHz, CDCl$_3$): δ=1.04 (t, 3H), 1.10 (t, 3H), 1.25 (t, 3H), 1.81 (s, 6H), 2.35-2.42 (m, 4H), 4.21 (q, 2H), 6.95 (d, 2H), 7.57 (d, 2H); LRMS: APCl$^+$: m/z 356 [MH$^+$].

Further elution provided Example 51 (40 mg, 11%).

$^1$H-NMR (400 MHz, CDCl$_3$): δ=1.03 (t, 3H), 1.11 (t, 3H), 1.82 (s, 6H), 2.35-2.41 (m, 4H), 3.76 (s, 3H), 6.96 (d, 2H), 7.57 (d, 2H); LRMS: APCl$^+$: m/z 342 [MH$^+$].

EXAMPLE 52

2-[4-(4-Cyanophenoxy)-3,5-dicyclopropyl-1H-pyrazol-1-yl]-N-methylacetamide

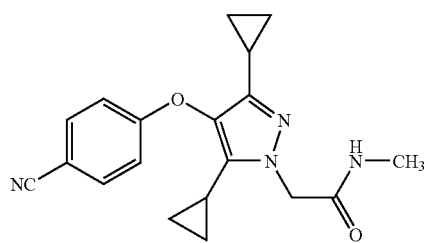

Method A: The ester from Example 36 (66 g, 189 mmol) was dissolved in hot ethanol (200 ml). The resulting solution was cooled to room temperature and methylamine, in ethanol (240 ml of 8M in ethanol, ~1920 mMol), was added. The reaction mixture was then stirred at room temperature for 20 hours, after which time it was evaporated under reduced pressure. The resulting residue was dissolved in ethyl acetate (1000 ml) and concentrated, under reduced pressure, to a volume of ~200 ml. The resultant solid (52.5 g) was collected by filtration, suspended in a mixture of diethyl ether (600 ml) and water (300 ml), and then stirred for 30 minutes. The mixture was then filtered and the wet solid was dissolved in dichloromethane (500 ml), dried over magnesium sulphate, filtered and concentrated under reduced pressure to give a solid (49.6 g). The solid was then dissolved in refluxing toluene (400 ml) and concentrated by distillation removal of some of the toluene (~120 ml). After cooling to room temperature over ~16 hours, the crystalline product was collected by filtration (45.6 g). A further recrystallisation was conducted by dissolving the crystalline product in hot 2-propanol (500 mL), followed by concentration of the mixture by distillation removal of some solvent (~380 ml). After cooling at room temperature for 2 hours, and then at 0° C. for 1 hour, the crystalline product was collected by filtration (42 g, 66%).

Mp=163° C.; $^1$H NMR (400 MHz, CDCl$_3$): δ=0.62-0.64 (m, 2H), 0.76-0.81 (m, 6H), 1.45 (m, 1H), 1.56 (m, 1H), 2.80 (d, 3H), 4.75 (s, 2H), 6.14 (brs, 1H), 6.96 (d, 2H), 7.59 (d, 2H); LRMS: APCl$^+$: m/z 336 [MH$^+$]; APCl$^-$: m/z 335 [M-H];

Method B: The diketone described in Preparation 29 (12 g, 0.045 mol) was slurried in ethanol (60 ml). Ethyl hydrazinoacetate hydrochloride (7.8 g, 0.05 mol) was added, and the reaction was warmed to 70° C. for 4 hours. It was then cooled to 15° C. and 8M methylamine solution in ethanol was added (60 ml, 0.45 mol). The reaction was stirred for 18 hours at 20 to 25° C. The resulting slurry was granulated at 0 to 2° C. before being collected by filtration and washed with ethanol (25 ml); (10.2 g, 68%)

Mp=163° C.; $^1$H NMR (400 MHz, CDCl$_3$): δ=0.62-0.64 (m, 2H), 0.76-0.81 (m, 6H), 1.45 (m, 1H), 1.56 (m, 1H), 2.80 (d, 3H), 4.75 (s, 2H), 6.14 (brs, 1H), 6.96 (d, 2H), 7.59 (d, 2H).

EXAMPLES 53-79

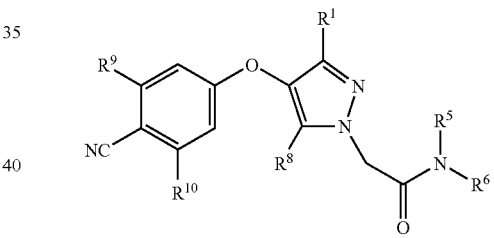

Compounds of the general formula above were prepared by a similar method to that of Example 52 using the appropriate ester and amine as the starting materials, with optional purification by flash chromatography on silica gel.

| Ex No | $R^9$; $R^{10}$; $R^8$; $R^1$; $R^5$; $R^6$ <br> Analytical Data |
|---|---|
| 53 | $R^9$=H; $R^{10}$=H; $R^8$=Et; $R^1$=Et; $R^5$=H; $R^6$=Me |
| (from Ex 35) | $^1$H NMR(400MHz, CDCl$_3$): δ=1.04(t, 3H), 1.13(t, 3H), 2.43(q, 2H), 2.49(q, 2H), 2.80(d, 3H), 4.67(s, 2H), 6.24(brs, 1H), 6.96(d, 2H), 7.58(d, 2H); LRMS: APCl$^+$: m/z 313[MH$^+$]; APCl$^-$: m/z 311[M-H]$^-$; 63% yield |
| 54 | $R^9$=H; $R^{10}$=H; $R^8$=Et; $R^1$=Et; $R^5$=H; $R^6$=H |
| (from Ex 35) | $^1$H NMR(400MHz, CDCl$_3$): δ=1.11(t, 3H), 1.17(t, 3H), 2.44(q, 2H), 2.54(q, 2H), 4.72(s, 2H), 5.67(brs, 1H), 6.30(brs, 1H), 6.97(d, 2H), 7.61(d, 2H); LRMS: APCl$^+$: m/z 299[MH$^+$]; APCl$^-$: m/z 297[M-H]$^-$; 38% yield |
| 55 | $R^9$=H; $R^{10}$=H; $R^8$=Et; $R^1$=Et; $R^5$=H; $R^6$=CH$_2$CH$_2$OH |
| (from Ex 35) | $^1$H NMR(400MHz, CDCl$_3$): δ=1.06(t, 3H), 1.11(t, 3H), 2.41(q, 2H), 2.50(q, 2H), 3.04(brs, 1H), 3.42(q, 2H), 3.68(t, 2H), 4.69(s, 2H), 6.68(brt, 1H), 6.96(d, 2H), 7.58(d, 2H); LRMS: APCl$^+$: m/z 343[MH$^+$]; APCl$^-$: m/z 341[M-H]$^-$; 76% yield |

-continued

| Ex No | $R^9$; $R^{10}$; $R^8$; $R^1$; $R^5$; $R^6$ Analytical Data |
|---|---|
| 56 (from Ex 35) | $R^9$=H; $R^{10}$=H; $R^8$=Et; $R^1$=Et; $R^5$=H; $R^6$=CH$_2$CH$_2$OMe<br>$^1$H NMR(400MHz, CDCl$_3$): δ=1.00(t, 3H), 1.07(t, 3H), 2.36(q, 2H), 2.44(q, 2H), 3.24(s, 3H), 3.36(brs, 4H), 4.63(s, 2H), 6.41(brs, 1H), 6.91(d, 2H), 7.52(d, 2H); LRMS: APCl$^+$: m/z 357[MH$^+$]; APCl$^-$: m/z 355[M−H]$^-$; 64% yield |
| 57 (from Ex 35) | $R^9$=H; $R^{10}$=H; $R^8$=Et; $R^1$=Et; $R^5$=Me; $R^6$=Me<br>$^1$H NMR(400MHz, CDCl$_3$): δ=1.05-1.12(m, 6H), 2.40(q, 2H), 2.46(q, 2H), 2.99(s, 3H), 3.10(s, 3H), 4.87(s, 2H), 7.00(d, 2H), 7.57(d, 2H); LRMS: APCl$^+$: m/z 327[MH$^+$]; 76% yield |
| 58 (from Ex 35) | $R^9$=H; $R^{10}$=H; $R^8$=Et; $R^1$=Et; $R^5$=H; $R^6$=Et<br>$^1$H NMR(400MHz, CDCl$_3$): δ=1.01-1.13(m, 9H), 2.41(q, 2H), 2.48(q, 2H), 3.25-3.28(m, 2H), 4.63(s, 2H), 6.16(brs, 1H), 6.93(d, 2H), 7.56(d, 2H); LRMS: APCl$^+$: m/z 327[MH$^+$]; APCl$^-$: m/z 325[M−H]$^-$; Mp=147-9° C.; Microanalysis: Found: C, 66.02; H, 6.81; N, 16.94%. C$_{18}$H$_{22}$N$_4$O$_2$ requires C, 66.24; H, 6.79; N, 17.16%; 54% yield |
| 59 (from Ex 35) | $R^9$=H; $R^{10}$=H; $R^8$=Et; $R^1$=Et; $R^5$=H; $R^6$=cPr<br>$^1$H NMR(400MHz, CDCl$_3$): δ=0.42-0.46(m, 2H), 0.79(q, 2H), 1.05(t, 3H), 1.13(t, 3H), 2.42(q, 2H), 2.48(q, 2H), 2.70(m, 1H), 4.63(s, 2H), 6.32(brs, 1H), 6.94(d, 2H), 7.59(d, 2H); LRMS: APCl$^+$: m/z 339[MH$^+$]; APCl$^-$: m/z 337[M−H]$^-$; Mp=146-7° C.; 27% yield |
| 60 (from Ex 35) | $R^9$=H; $R^{10}$=H; $R^8$=Et; $R^1$=Et; $R^5$=H; $R^6$=iPr<br>$^1$H NMR(400MHz, CDCl$_3$): δ=1.04-1.16(m, 12H), 2.41-2.51(m, 4H), 4.05(m, 1H), 4.63(s, 2H), 5.92(brs, 1H), 6.94(d, 2H), 7.59(d, 2H); LRMS: APCl$^+$: m/z 341[MH$^+$]; Mp=145° C.; Microanalysis: Found: C, 66.39; H, 7.25; N, 16.34%. C$_{19}$H$_{24}$N$_4$O$_2$ requires C, 67.04; H, 7.11; N, 16.46%; 42% yield. |
| 61 (from Ex 38) | $R^9$=Me; $R^{10}$=Me; $R^8$=cPr; $R^1$=cPr; $R^5$=H; $R^6$=H<br>$^1$H NMR(400MHz, DMSO-D$_6$): δ=0.52-0.55(m, 2H), 0.61-0.70(m, 6H), 1.45(m, 1H), 1.56(m, 1H), 2.40(s, 3H), 4.65(s, 2H), 6.78(s, 2H), 7.23(brs, 1H), 7.41(brs, 1H); LRMS: APCl$^+$: m/z 351[MH$^+$]; APCl$^-$: m/z 349[M−H]$^-$; 73% yield. |
| 62 (from Ex 37) | $R^9$=Me; $R^{10}$=Me; $R^8$=Me; $R^1$=Me; $R^5$=H; $R^6$=Me<br>$^1$H NMR(400MHz, CDCl$_3$): δ=2.08(s, 6H), 2.47(s, 6H), 2.82(d, 3H), 4.65(s, 2H), 6.09(brs, 1H), 6.58(s, 2H); LRMS: APCl$^+$: m/z 313[MH$^+$]; APCl$^-$: m/z 311[M−H]$^-$; Mp=217° C.; Microanalysis: Found: C, 64.23; H, 6.35; N, 17.49%. C$_{17}$H$_{20}$N$_4$O$_2$ requires C, 65.37; H, 6.45; N, 17.94%; 63% yield |
| 63 (from Ex 37) | $R^9$=Me; $R^{10}$=Me; $R^8$=Me; $R^1$=Me; $R^5$=H; $R^6$=H<br>$^1$H NMR(400MHz, CDCl$_3$): δ=2.07(s, 3H), 2.11(s, 3H), 2.47(s, 6H), 4.69(s, 2H), 5.49(brs, 1H), 6.17(brs, 1H), 6.58(s, 2H); LRMS: APCl$^+$: m/z 299[MH$^+$]; 84% yield |
| 64 (from Ex 36) | $R^9$=H; $R^{10}$=H; $R^8$=cPr; $R^1$=cPr; $R^5$=H; $R^6$=H<br>$^1$H NMR(400MHz, DMSO-d$_6$): δ=0.51-0.54(m, 2H), 0.61-0.70(m, 6H), 1.46(m, 1H), 1.56(m, 1H), 4.66(s, 2H), 7.06(d, 2H), 7.23(brs, 1H), 7.42(brs, 1H), 7.81(d, 2H); LRMS: APCl$^+$: m/z 323[MH$^+$]; APCl$^-$: m/z 321[M−H]$^-$; 67% yield |
| 65 (from Ex 38) | $R^9$=Me; $R^{10}$=Me; $R^8$=cPr; $R^1$=cPr; $R^5$=H; $R^6$=Me<br>$^1$H NMR(400MHz, CDCl$_3$): δ=0.64-0.68(m, 2H), 0.79-0.84(m, 6H), 1.48(m, 1H), 1.59(m, 1H), 2.48(s, 6H), 2.83(d, 3H), 4.78(s, 2H), 6.11(brs, 1H), 6.62(s, 2H); LRMS: APCl$^+$: m/z 365[MH$^+$]; APCl$^-$: m/z 363[M−H]$^-$; 77% yield; Mp=156-157° C.; Microanalysis: Found: C, 68.46; H, 6.60; N, 15.09%. C$_{21}$H$_{24}$N$_4$O$_2$•0.25H$_2$O requires C, 68.38; H, 6.64; N, 15.20%. |
| 66 (from Ex 39) | $R^9$=Me; $R^{10}$=Me; $R^8$=Et; $R^1$=Et; $R^5$=H; $R^6$=Me<br>$^1$H NMR(400MHz, CDCl$_3$): δ=1.06(t, 3H), 1.15(t, 3H), 2.42-2.50(m, 10H), 2.82(d, 3H), 4.68(s, 2H), 6.17(brs, 1H), 6.60(s, 2H); LRMS: APCl$^+$: m/z 341[MH$^+$]; 74% yield |
| 67 (from Ex 39) | $R^9$=Me; $R^{10}$=Me; $R^8$=Et; $R^1$=Et; $R^5$=H; $R^6$=H<br>$^1$H NMR(400MHz, CDCl$_3$): δ=1.09(t, 3H), 1.14(t, 3H), 2.41-2.52(m, 10H), 4.69(s, 2H), 5.57(brs, 1H), 6.21(brs, 1H), 6.60(s, 2H); LRMS: APCl$^+$: m/z 327[MH$^+$]; 70% yield |
| 68 (from Ex 40) | $R^9$=H; $R^{10}$=CF$_3$; $R^8$=cPr; $R^1$=cPr; $R^5$=H; $R^6$=Me<br>$^1$H NMR(400MHz, CDCl$_3$): δ=0.63-0.66(m, 2H), 0.81-0.87(m, 6H), 1.46-1.58(m, 2H), 2.84(d, 3H), 4.78(s, 2H), 6.08(brs, 1H), 7.13(d, 1H), 7.33(s, 1H), 7.78(d, 1H); LRMS: APCl$^+$: m/z 405[MH$^+$]; APCl$^-$: m/z 403[M−H]$^-$; Microanalysis: Found: C, 59.11; H, 4.86; N, 13.65%. C$_{20}$H$_{19}$N$_4$F$_3$O$_2$ requires C, 59.41; H, 4.70; N, 13.86%; 52% yield |
| 69 (from Ex 41) | $R^9$=H; $R^{10}$=Me; $R^8$=cPr; $R^1$=cPr; $R^5$=H; $R^6$=Me<br>$^1$H NMR(400MHz, CDCl$_3$): δ=0.64-0.66(m, 2H), 0.79-0.83(m, 6H), 1.46(m, 1H), 1.57(m, 1H), 2.51(s, 3H), 2.82(d, 3H), 4.77(s, 2H), 6.08(brs, 1H), 6.75(d, 1H), 6.83(s, 1H), 7.53(d, 1H); LRMS: APCl$^+$: m/z 351[MH$^+$]; APCl$^-$: m/z 349[M−H]$^-$; 53% yield |
| 70 (from Ex 49) | $R^9$=Me; $R^{10}$=Me; $R^8$=cPr; $R^1$=Me; $R^5$=H; $R^6$=Me<br>$^1$H NMR(400MHz, CDCl$_3$): δ=0.65-0.68(m, 2H), 0.82-0.87(m, 2H), 1.51(m, 1H), 2.04(s, 3H), 2.48(s, 6H), 2.83(d, 3H), 4.82(s, 2H), 6.10(brs, 1H), 6.57(s, 2H); LRMS: APCl$^+$: m/z 339[MH$^+$]; APCl$^-$: m/z 337[M−H]$^-$; Microanalysis: Found: C, 67.04; H, 6.56; N, 15.99%. C$_{19}$H$_{22}$N$_4$O$_2$ requires C, 67.44; H, 6.55; N, 16.56%; 55% yield |
| 71 (from Ex 48) | $R^9$=Me; $R^{10}$=Me; $R^8$=Me; $R^1$=cPr; $R^5$=H; $R^6$=Me<br>$^1$H NMR(400MHz, CDCl$_3$): δ=0.77-0.79(m, 4H), 1.62(m, 1H), 2.03(s, 3H), 2.46(s, 6H), 2.81(m, 3H), 4.61(s, 2H), 6.14(brs, 1H), 6.61(s, 2H); LRMS: APCl$^+$: m/z 339[MH$^+$]; APCl$^-$: m/z 337[M−H]$^-$; 41% yield |
| 72 (from Ex 48) | $R^9$=Me; $R^{10}$=Me; $R^8$=Me; $R^1$=cPr; $R^5$=H; $R^6$=H<br>$^1$H NMR(400MHz, DMSO-D$_6$): δ=0.62-0.64(m, 2H), 0.67-0.70(m, 2H), 1.51(m, 1H), 1.94(s, 3H), 2.40(s, 6H), 4.59(s, 2H), 6.78(s, 2H), 7.21(brs, 1H), 7.45(brs, 1H); LRMS: APCl$^+$: m/z 325[MH$^+$]; APCl$^-$: m/z 323[M−H]$^-$; 80% yield |

| Ex No | $R^9$; $R^{10}$; $R^8$; $R^1$; $R^5$; $R^6$<br>Analytical Data |
|---|---|
| 73<br>(from<br>Ex 49) | $R^9$=Me; $R^{10}$=Me; $R^8$=cPr; $R^1$=Me; $R^5$=H; $R^6$=H<br>$^1$H NMR(400MHz, DMSO-D6): δ=0.53-0.55(m, 2H), 0.70-0.73(m, 2H), 1.59(m, 1H),<br>1.86(s, 3H), 2.39(s, 6H), 4.68(s, 2H), 6.74(s, 2H), 7.24(brs, 1H), 7.42(brs, 1H); LRMS:<br>APCI$^+$: m/z 325[MH$^+$]; APCI$^-$: m/z 323[M−H]$^-$; Microanalysis: Found: C, 66.50; H, 6.20;<br>N, 17.29%. $C_{18}H_{20}N_4O_2$ requires C, 66.67; H, 6.17; N, 17.28%; 90% yield |
| 74<br>(from<br>Ex 42) | $R^9$=Me; $R^{10}$=Me; $R^8$=H; $R^1$=cPr; $R^5$=H; $R^6$=Me<br>$^1$H-NMR(400MHz, CDCl$_3$): δ=0.83-0.85(m, 4H), 1.67(m, 1H), 2.48(s, 6H), 2.82(d, 3H),<br>4.66(s, 2H), 6.25(brs, 1H), 6.68(s, 2H), 7.28(s, 1H); LRMS: APCI$^+$: m/z 325[MH$^+$];<br>72% yield |
| 75<br>(from<br>Ex 45) | $R^9$=H; $R^{10}$=H; $R^8$=cPr; $R^1$=Me; $R^5$=H; $R^6$=Me<br>$^1$H-NMR(400MHz, CDCl$_3$): δ=0.63-0.66(m, 2H), 0.82-0.87(m, 2H), 1.50(m, 1H),<br>2.04(s, 3H), 2.84(d, 3H), 4.80(s, 2H), 6.10(brs, 1H), 6.93(d, 2H), 7.60(d, 2H); LRMS:<br>APCI$^+$: m/z 311[MH$^+$]; 26% yield white solid |
| 76<br>(from<br>Ex 44) | $R^9$=H; $R^{10}$=H; $R^8$=Me; $R^1$=cPr; $R^5$=H; $R^6$=Me<br>$^1$H-NMR(400MHz, CDCl$_3$): δ=0.80(d, 4H), 1.63(m, 1H), 2.06(s, 3H), 2.82(d, 3H),<br>4.61(s, 2H), 6.09(brs, 1H), 6.97(d, 2H), 7.60(d, 2H); LRMS: APCI$^+$: m/z 311[MH$^+$]; 86%<br>yield white solid |
| 77<br>(from<br>Ex 46) | $R^9$=H; $R^{10}$=Me; $R^8$=Me; $R^1$=cPr; $R^5$=H; $R^6$=Me<br>$^1$H-NMR(400MHz, CDCl$_3$): δ=0.81(d, 4H), 1.64(m, 1H), 2.05(s, 3H), 2.51(s, 3H),<br>2.82(d, 3H), 4.62(s, 2H), 6.08(brs, 1H), 6.76(d, 1H), 6.83(s, 1H), 7.73(d, 1H); LRMS:<br>APCI$^+$: m/z 325[MH$^+$]; Mp=208-210C; 60% yield |
| 78<br>(from<br>Ex 47) | $R^9$=H; $R^{10}$=Me; $R^8$=cPr; $R^1$=Me; $R^5$=H; $R^6$=Me<br>$^1$H-NMR(400MHz, CDCl$_3$): δ=0.63-0.67(m, 2H), 0.81-0.86(m, 2H), 1.50(m, 1H),<br>2.03(s, 3H), 2.50(s, 3H), 2.83(d, 3H), 4.80(s, 2H), 6.12(brs, 1H), 6.70(d, 1H), 6.78(s, 1H),<br>7.51(d, 1H); LRMS: APCI$^+$: m/z 325[MH$^+$]; APCI$^-$: m/z 323[M−H]$^-$. 28% yield solid |
| 79<br>(from<br>Ex 43) | $R^9$=Cl; $R^{10}$=H; $R^8$=cPr; $R^1$=cPr; $R^5$=H; $R^6$=Me<br>$^1$H-NMR(400MHz, CDCl$_3$): δ=0.64-0.68(m, 2H), 0.83-0.88(m, 6H), 1.51(m, 1H),<br>1.58(m, 1H), 2.82(d, 3H), 4.79(s, 2H), 6.20(brs, 1H), 6.90(d, 1H), 7.04(s, 1H), 7.61(d, 1H);<br>LRMS: APCI$^+$: m/z 371[MH$^+$]; 68% yield solid |

EXAMPLE 80

2-[4-(4-Cyanophenoxy)-5-ethyl-3-methoxy-1]-pyrazol-1-yl} acetamide

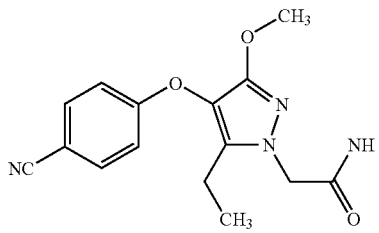

(a) tert-Butyl[4-(4-cyanophenoxy)-5-ethyl-3-methoxy-1H-pyrazol-1-yl]acetate

Potassium carbonate (306 mg, 2.22 mmol) and tert-butyl-bromoacetate (330 μl, 2.22 mmol) were added to a solution of the benzonitrile of Example 15 (270 mg, 1.11 mmol) in N,N-dimethylformamide (5 ml). The reaction mixture was stirred overnight at 50° C. under nitrogen and then evaporated to dryness. The resulting residue was partitioned between dichloromethane (15 ml) and water (15 ml). The organic layer was separated, and the aqueous layer was extracted twice more with dichloromethane (2×10 ml). The organic extracts were combined, dried over magnesium sulphate, filtered and concentrated under reduced pressure to give a yellow oil. The crude product was purified by flash chromatography on silica gel eluting with ethyl acetate:pentane (4:1, by volume) to provide the title compound as a colourless oil (295 mg, 75%).

$^1$H-NMR (400 MHz, CDCl$_3$): δ=1.09 (t, 3H), 1.48 (s, 9H), 2.46 (q, 2H), 3.86 (s, 3H), 4.58 (s, 2H), 7.02 (d, 2H), 7.58 (d, 2H); LRMS: APCI$^+$: 358 [MH$^+$] and 302 [M-tBu]; HPLC/ESMS: UV/ELSD single peak 358 [MH$^+$].

(b) [4-(4-Cyanophenoxy)-5-ethyl-3-methoxy-1H-pyrazol-1-yl] acetic acid

The pyrazole acetate of step (a) above (290 mg, 0.81 mmol) was added to a mixture of dichloromethane (5 ml) and trifluoroacetic acid (5 ml). The reaction mixture was then stirred at room temperature for 2.5 hours, after which time the solvent was evaporated and any residual trifluoroacetic acid was azeotroped with toluene. The crude product was partitioned between ethyl acetate (20 ml) and water (20 ml). The organic layer was then separated and the aqueous layer was extracted twice more with ethyl acetate (2×15 ml). The organic extracts were combined, dried over magnesium sulphate, filtered and evaporated to provide the title compound as a white solid (242 mg, 99%).

$^1$H-NMR (400 MHz, CDCl$_3$): δ=1.10 (t, 3H), 2.50 (q, 2H), 3.86 (s, 3H), 4.75 (s, 2H), 7.00 (d, 2H), 7.58 (d, 2H); LRMS: APCI$^+$: m/z 302 [MH$^+$]; APCI$^-$: m/z 300 [M-H]$^-$ HPLC/ESMS: UV/ELSD single peak m/z 302 [MH+]; Microanalysis: Found C, 59.30; H, 5.14; N, 13.53%. $C_{15}H_{15}N_3O_4 \cdot 0.05H_2O$ requires C, 59.62; H, 5.04; N, 13.90%.

(c) 2-[4-(4-Cyanophenoxy)-5-ethyl-3-methoxy-1H-pyrazol-1-yl]acetamide

The acid of step (b) above (180 mg, 0.6 mmol) was suspended in dichloromethane (5 ml), and oxalyl chloride (150

μl, 1.72 mmol) was added, resulting in gas evolution. The reaction mixture was stirred at room temperature for 1 hour, under nitrogen. The solvent was then evaporated under reduced pressure and the residue was azeotroped with toluene 3 times. The crude intermediate acid chloride was carried straight through to the next step. It was dissolved in tetrahydrofuran (2 ml), and ammonia 0.5M in dioxane (10 ml) was added. After stirring overnight at room temperature, analysis by TLC showed little product had formed. A further portion of fresh 0.5M ammonia in dioxane (10 ml) was added to the reaction mixture and stirring was continued for another overnight period. The reaction mixture was evaporated and the residue was partitioned between dichloromethane (20 ml) and aqueous sodium bicarbonate (10 ml). The organic layer was separated and the aqueous layer was extracted 3 times with dichloromethane (10 ml). The organic extracts were combined, dried over magnesium sulphate, filtered and evaporated under reduced pressure. The crude product was purified by flash chromatography on silica gel eluting with ethyl acetate to provide the title compound (20 mg, 17%).

$^1$H-NMR (400 MHz, CDCl$_3$): δ=1.10 (t, 3H), 2.52 (q, 2H), 3.88 (s, 3H), 4.58 (s, 2H), 5.45 (brs, 1H), 6.25 (brs, 1H), 6.98 (d, 2H), 7.58 (d, 2H); LRMS:APCl$^+$: m/z 301 [MH$^+$]; APCl$^-$: m/z 299 [M−H]$^-$; HPLC/ESMS: UV/ELSD single peak m/z 301 [MH$^+$].

EXAMPLES 81-83

The following compounds were prepared by a similar method to that described for Example 80 using the appropriate acid and amine as the starting materials.

| Ex No | Structure | Analytical Data |
|---|---|---|
| 81 (from(b) below) | 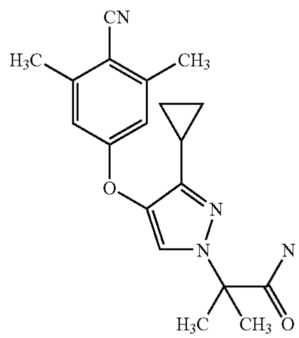 | $^1$H-NMR(400 MHz, CD$_3$OD): δ=0.75-0.79(m, 4H), 1.64 (m, 1H), 1.76(s, 6H), 2.46(s, 6H), 6.81(s, 2H), 7.69(s, 1H); LRMS: APCl$^+$: m/z 339 [MH$^+$]; APCl$^-$ m/z 337 [M−H]$^-$; 51% yield |
| 82 (from(c) below) | 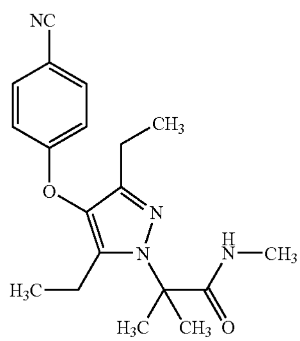 | $^1$H-NMR(400 MHz, CDCl$_3$): δ=1.02(t, 3H), 1.14(t, 3H), 1.81(s, 6H), 2.42-2.48(m, 4H), 2.79(d, 3H), 5.35(brs, 1H), 6.95(d, 2H), 7.60(d, 2H); LRMS: APCl$^+$: m/z 341 [MH$^+$]; 27% yield |
| 83 (from(g) below) | 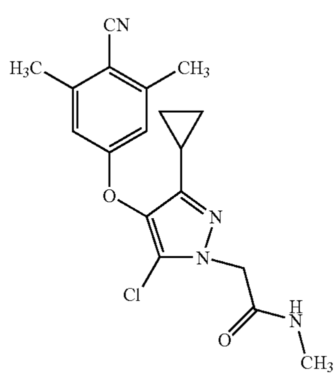 | $^1$H-NMR(400 MHz, CDCl$_3$): δ=0.71-0.75(m, 2H, A), 0.85-0.87(m, 4H, B), 0.89-0.93(m, 2H, A), 1.57(m, 1H, major regioisomer A), 1.69(m, 1H, minor regioisomer B), 2.49(s, 6H, A+B), 2.86(d, 3H, A+B), 4.73(s, 2H, B), 4.83 (s, 2H, A), 6.02(brs, 1H), 6.61(s, 2H, A), 6.66(S, 2H, B); LRMS: APCl$^+$: m/z 359 [MH$^+$]; APCl$^-$m/z 357[M−H]$^-$; Microanalysis: Found: C, 60.20; H, 5.35; N, 15.43%. C$_{18}$H$_{19}$N$_4$O$_2$ requires C, 60.25; H, 5.34; N, 15.61%; 70% yield, isolated as 6:1 mixture of diastereoisomers |

(a) tert-Butyl 2-[4-(4-cyano-3,5-dimethylphenoxy)-3-cyclopropyl-1H-pyrazol-1-yl]-2-methylpropanoate The title compound (510 mg, 26%) was prepared by a similar method to that described for the ester of Example 50, using the acetate of Preparation 21 and 3 equivalents of methyl iodide as starting materials.
$^1$H-NMR (400 MHz, CDCl$_3$): δ=0.73-0.77 (m, 2H), 0.79-0.82 (m, 4H), 1.40 (s, 9H), 1.63 (m, 1H), 1.75 (s, 6H), 2.47 (s, 6H), 6.70 (s, 2H), 7.38 (s, 1H); LRMS:APCl$^+$: m/z 396 [MH$^+$] and 340 [acidH$^+$]; APCl$^-$: m/z 338 [acid-H]$^-$.

(b) 2-[4-(4-Cyano-3,5-dimethylphenoxy)-3-cyclopropyl-1H-pyrazol-1-yl]-2-methyl propanoic acid The title compound (287 mg, 66%) was prepared by a similar method to that described for the acid of step (b) of Example 80 using the ester of step (a) from above as starting material.
$^1$H-NMR (400 MHz, CDCl$_3$): δ=0.86-0.88 (m, 4H), 1.69 (m, 1H), 1.82 (s, 6H), 2.49 (s, 6H), 6.68 (s, 2H), 7.41 (s, 1H); LRMS: APCl$^+$: m/z 340 [MH$^+$]; APCl$^-$: m/z 338 [M-H]$^-$ (c) 2-[4-(4-Cyanophenoxy)-3,5-diethyl-1H-pyrazol-1-yl]-2-methylpropanoic acid The title compound (190 mg, 100%) was prepared by a similar method to that described for the acid of step (a) from Example 140 using the ester of Example 50 as starting material.
$^1$H-NMR (400 MHz, DMSO-D$_6$): δ=0.94-1.03 (m, 6H), 1.68 (s, 6H), 2.28 (q, 2H), 2.38 (q, 2H), 7.00 (d, 2H), 7.80 (d, 2H); LRMS: APCl$^+$: m/z 328 [MH$^+$]; APCl$^-$: m/z 326 [M-H]$^-$.

(d) 4-[(3-Cyclopropyl-1-tetrahydro-2H-pyran-2-yl-1H-pyrazol-4-yl)oxy]-2,6-dimethyl benzonitrile p-Toluenesulphonic acid (20 mg, 0.12 mmol) was added to a solution of the benzonitrile of Example 16 (1 g, 3.94 mmol) in tetrahydrofuran (30 ml). 3,4-Dihydro-2H-pyran (664 mg, 7.9 mmol) was then added dropwise at room temperature. The reaction mixture was stirred at room temperature, under nitrogen, for 15 hours. It was then evaporated under reduced pressure and the residue was partitioned between ethyl acetate (100 ml) and aqueous sodium bicarbonate (50 ml). The organic layers were washed with brine (50 ml), dried over sodium sulphate, filtered and concentrated under reduced pressure to provide the title compound (1.93 mg, 100%).
$^1$H-NMR (400 MHz, CDCl$_3$): δ=0.74-0.79 (m, 2H), 0.83-0.87 (m, 2H), 1.54-1.76 (m, 5H), 1.85 (m, 1H), 2.47 (s, 6H), 3.51 (m, 1H), 3.68 (m, 1H), 3.88 (m, 1H), 4.09 (m, 1H), 6.70 (s, 2H), 7.40 (s, 1H), contaminated with some 3,4-dihydro-21+pyran; LRMS:APCl$^+$: m/z 338 [MH$^+$] and m/z 254 [M-THP].

(e) 4-[(5-Chloro-3-cyclopropyl-1-tetrahydro-21+pyran-2-yl-1H-pyrazol-4-yl)oxy]-2,6-dimethyl benzonitrile & 4-[(5-chloro-3-cyclopropyl-1]-pyrazol-4-yl)oxy]-2,6-dimethylbenzonitrile N-Chlorosuccinimide (764 mg, 5.71 mmol) was added to a solution of the benzonitrile of step (d) from above (1.93 g, 5.71 mmol) in N,N-dimethylformamide (30 ml). The reaction mixture was then heated at 50° C. for 15 hours, after which time it was evaporated under reduced pressure, and the residue was partitioned between dichloromethane (150 ml) and water (100 ml). The organic layers were dried over sodium sulphate, filtered, and then concentrated under reduced pressure. The crude product was purified by flash chromatography on silica gel eluting with ethyl acetate:pentane (gradient from 2:98 to 30:70, by volume) to provide the compound of Preparation 30 (388 mg, 18%) eluted first.
$^1$H-NMR (400 MHz, CDCl$_3$): δ=0.65 (m, 1H), 0.84-0.92 (m, 3H), 1.60-1.63 (m, 2H), 1.68-1.73 (m, 3H), 1.94 (m, 1H), 2.14 (m, 1H), 2.48 (s, 7H), 3.67 (t, 1H), 5.50 (d, 1H), 6.62 (s, 2H); LRMS: APCl$^+$: m/z 288 [(M-THP)H$^+$.

Further elution provided the compound of Preparation 31 (325 mg, 20%).
$^1$H-NMR (400 MHz, CDCl$_3$): δ=0.80-0.82 (m, 2H), 0.86-0.94 (m, 2H), 1.74 (m, 1H), 2.49 (s, 6H), 6.65 (s, 2H); LRMS: APCl$^+$: m/z 288 [MH$^+$]; APCl$^-$: m/z 286 [M-H].

(f) tert-Butyl[5/3-chloro-4-(4-cyano-3,5-dimethylphenoxy)-3/5-cyclopropyl-1H-pyrazol-1-yl]acetate The title compound (638 mg, 100%, isolated as a 2.5:1 mixture of regioisomers, contaminated with some tert-butyl bromoacetate) was prepared by a similar method to that described for the ester of step (a) from Example 80 using the benzonitrile of step (e) from above as starting material.
$^1$H-NMR (400 MHz, CDCl$_3$): δ=0.73-0.85 (m, 4H, A+B), 1.58 (m, 1H, major regioisomer A), 1.61 (m, 1H, minor regioisomer B), 2.48 (s, 6H, A+B), 4.72 (s, 2H, B), 4.82 (s, 2H, A), 6.64 (s, 2H, A), 6.69 (s, 2H, B); LRMS: APCl$^+$: m/z 401 [MH$^+$] and 346 [acidH$^+$.

(g) [5/3-Chloro-4-(4-cyano-3,5-dimethylphenoxy)-3/5-cyclopropyl-1H-pyrazol-1-yl] acetic acid The title compound (287 mg, 66%, isolated as a 5:1 mixture of regioisomers) was prepared by a similar method to that described for the acid of step (b) from Example 80 using the ester of step (f) from above as starting material.
$^1$H-NMR (400 MHz, CDCl$_3$): δ=0.75-0.77 (m, 2H, A), 0.82-0.84 (m, 4H, B), 0.87-0.90 (m, 2H, A), 1.52 (m, 1H, major regioisomer A), 1.68 (m, 1H, minor regioisomer B), 2.49 (s, 6H, A+B), 4.92 (s, 2H, B), 5.02 (s, 2H, A), 6.63 (s, 2H, A), 6.67 (s, 2H, B); LRMS: APCl$^+$: m/z 346 [MH$^+$]; APCl$^-$: m/z 344 [M-H]$^-$.

EXAMPLE 84

4-{[1-(Cyanomethyl)-3,5-dimethyl-1H-pyrazol-4-yl]oxy}-2,6-dimethylbenzonitrile

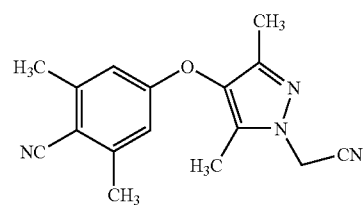

Method A: Sodium hydride (60% dispersion in oil, 46 mg, 1.2 mmol) was added to a stirred solution of the benzonitrile of Example 6 (320 mg, 1.33 mmol) in dry N,N-dimethylformamide (5 ml) at 0° C., under nitrogen. The reaction mixture was stirred for 45 minutes, during which time hydrogen was evolved, and then bromoacetonitrile (0.3 ml, 1.4 mmol) was added. The reaction mixture was then stirred for a further 18 hours at room temperature. It was then quenched by the addition of water (20 ml), concentrated under reduced pressure, and the residue was diluted with dichloromethane (20 ml). The organic layer was separated, dried over magnesium sulphate and concentrated under reduced pressure. The crude product was purified by flash chromatography on silica gel eluting with ethyl acetate:pentane (1:2 to 1:1, by volume) to provide the title compound (135 mg, 36%).

Method B: Trifluoroacetic anhydride (70 µl, 0.23 mmol) was added to a solution of the amide of Example 63 (60 mg, 0.20 mmol) in dichloromethane (3 ml) and pyridine (1 ml), and the mixture was stirred at room temperature for 18 hours. It was then diluted with dichloromethane (10 ml), washed twice with water (10 ml) and then twice with 2M hydrochloric acid (10 ml). The organic layer was dried over magnesium sulphate, filtered and evaporated under reduced pressure. The crude product was purified by flash chromatography on silica gel eluting with ethyl acetate:pentane (1:1, by volume) to provide the title compound (40 mg, 71%).

$^1$H-NMR (400 MHz, CDCl$_3$): δ=2.04 (s, 3H), 2.19 (s, 3H), 2.47 (s, 6H), 4.95 (s, 2H), 6.59 (s, 2H); LRMS: APCl$^+$: m/z 281 [MH$^+$].

EXAMPLE 85

4-{[1-(Cyanomethyl)-1H-pyrazol-4-yl]oxy)-2,6-dimethylbenzonitrile

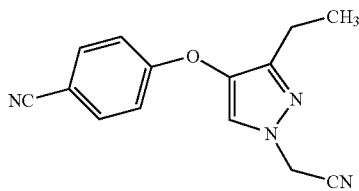

The title compound (13 mg, 55%, isolated as a 4:3 mixture of regioisomers) was prepared by a similar method (method A) to that described for Example 84 using the benzonitrile of Preparation 18 as the starting material.

$^1$H-NMR (400 MHz, CDCl$_3$): δ=1.14-1.22 (m, 6H), 2.47 (q, 2H, R1), 2.67 (q, 2H, R2), 5.00 (s, 2H, R1), 5.02 (s, 2H, R2), 7.01 (d, 2H), 7.40 (s, 1H, R2), 7.42 (s, 1H, R1), 7.61 (d, 2H); LRMS: APCl$^+$: m/z 253 [MH$^+$]

EXAMPLE 86

4-([1-(Cyanomethyl)-3,5-diethyl-1 pyrazol-4-yl]oxy}benzonitrile

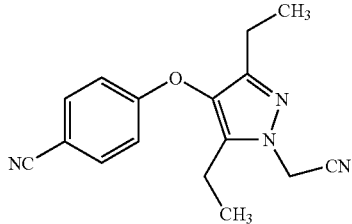

The title compound (100 mg, 34%) was prepared by a similar method (method A) to that described for Example 84 using the benzonitrile of Example 5, potassium carbonate and chloroacetonitrile as the starting materials.

$^1$H-NMR (400 MHz, CDCl$_3$): δ=1.12-1.16 (m, 6H), 2.41 (q, 2H), 2.59 (q, 2H), 4.96 (s, 2H), 6.96 (d, 2H), 7.61 (d, 2H); LRMS: APCl$^+$: m/z 281 [MH$^+$]; APCl$^-$: m/z 279 [M-H]$^-$

EXAMPLE 87

4-{[1-(Cyanomethyl)-3,5-diethyl-1H-pyrazol-4-yl]oxy}-2,6-dimethylbenzonitrile

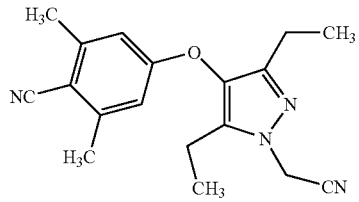

The title compound (45 mg, 8%) was prepared by a similar method (method A) to that described for Example 84, using the benzonitrile of Example 8, potassium carbonate and bromoacetonitrile as the starting materials.

$^1$H-NMR (400 MHz, CDCl$_3$): δ=1.11-1.18 (m, 6H), 2.39 (q, 2H), 2.46 (s, 6H), 2.58 (q, 2H), 4.95 (s, 2H), 6.60 (s, 2H); LRMS: APCl$^+$: m/z 309 [MH$^+$].

EXAMPLE 88

4-{(1-(Cyanomethyl)-5-ethyl-3-methoxy-1 pyrazol-4-yl]oxy}benzonitrile

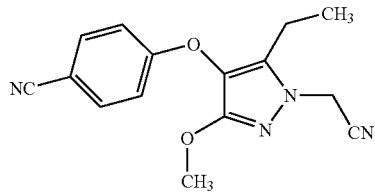

The title compound (10.4 mg, 61%) was prepared by a similar method (method B) to that described for Example 84 using the amide of Example 80 as the starting material.

$^1$H-NMR (400 MHz, CDCl$_3$): δ=1.18 (t, 3H), 2.59 (q, 2H), 3.87 (s, 3H), 4.84 (s, 2H), 6.99 (d, 2H), 7.60 (d, 2H); LRMS: APCl$^+$: m/z 283 [MH$^+$]; HPLC/MS: UV/ELSD m/z 324 [MHMeCN$^+$]; HRMS: consistent with product molecular formula.

EXAMPLE 89

4-{[1-(1-Cyano-1-methylethyl)-3-cyclopropyl-1H-pyrazol-4-yl]oxy}-2,6-dimethylbenzonitrile

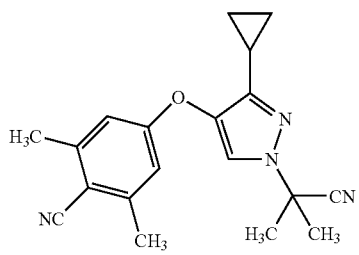

The title compound (79 mg, 82%) was prepared by a similar method (method B) to that described for Example 84 using the amide of Example 81 as the starting material.

$^1$H-NMR (400 MHz, CDCl$_3$): δ=0.78-0.82 (m, 2H), 0.84-0.87 (m, 2H), 1.63 (m, 1H), 1.96 (s, 6H), 2.49 (s, 6H), 6.69 (s,

2H), 7.45 (s, 1H); LRMS:APCl⁺: m/z 321 [MH⁺]; Microanalysis: Found: C, 71.03; H, 6.30; N, 17.31%. $C_{19}H_{20}N_4O_1$ requires C, 71.23; H, 6.29; N, 17.49%.

EXAMPLES 90-92

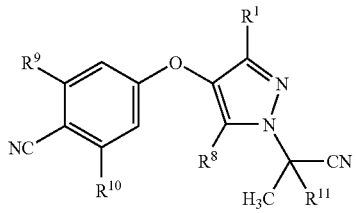

Compounds of the general formula above, wherein $R^{11}$ represents H or $C_{1-4}$alkyl, were prepared by a similar method to that described for Example 50 using the appropriate cyanomethylbenzonitrile and appropriate stoichiometry for sodium hydride and methyl iodide as the starting materials.

| Ex No | $R^9$; $R^{10}$; $R^8$; $R^1$; $R^{11}$ <br> Analytical Data |
|---|---|
| 90 <br> (from <br> Ex 84) | $R^9$=Me; $R^{10}$=Me; $R^8$=Me; $R^1$=Me; $R^{11}$=Me <br> ¹H-NMR(400MHz, CDCl₃): δ=2.01(s, 6H), 2.03(s, 3H), 2.36(s, 3H), 2.48(s, 6H), 6.60(s, 2H); LRMS: APCl⁺: m/z 309[MH⁺]; 63% yield |
| 91 <br> (from <br> Ex 86) | $R^9$=H; $R^{10}$=H; $R^8$=Et; $R^1$=Et; $R^{11}$=Me <br> ¹H-NMR(400MHz, CDCl₃): δ=1.09(t, 3H), 1.17(t, 3H), 2.01(s, 3H), 2.36(q, 2H), 2.84(q, 2H), 6.95(d, 2H), 7.59(d, 2H); LRMS: APCl⁺: m/z 309[MH⁺]; 54% yield |
| 92 <br> (from <br> Ex 86) | $R^9$=H; $R^{10}$=H; $R^8$=Et; $R^1$=Et; $R^{11}$=H <br> ¹H-NMR(400MHz, CDCl₃): δ=1.11(q, 6H), 1.93(d, 3H), 2.40(q, 2H), 2.57(q, 2H), 5.14(q, 1H), 6.95(d, 2H), 7.59(d, 2H); LRMS: APCl⁺: m/z 295[MH⁺]; 24% yield |

EXAMPLES 119 & 120

4-({3-Cyclopropyl-5-methyl-1-[(5-methylisoxazol-3-yl)methyl]-1H-pyrazol-4-yl}oxy)-2,6-dimethylbenzonitrile and 4-({5-cyclopropyl-3-methyl-1-[(5-methylisoxazol-3-yl)methyl]-1H-pyrazol-4-yl}oxy)-2,6-dimethylbenzonitrile

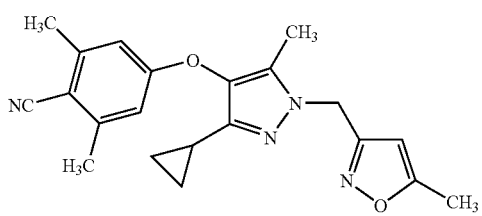

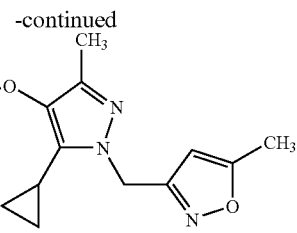

Potassium carbonate (310 mg, 2.25 mmol), followed by 3-(bromomethyl)-5-methylisoxazole (263 mg, 1.5 mmol) was added to a stirred solution of the benzonitrile of Example 2 (200 mg, 0.75 mmol) in dry N-methylpyrrolidinone (4 ml), at room temperature, under nitrogen. The reaction mixture was then stirred at 90° C. for 22 hours, after which time it was diluted with ethyl acetate (30 ml) and washed twice with water (25 ml) and then brine (20 ml). The organic layer was separated, dried over sodium sulphate, filtered and concentrated under reduced pressure. The residue containing the two regioisomers (as identified by TLC) was purified by flash chromatography on silica gel eluting with ethyl acetate:cyclohexane (30:70 by volume) to provide Example 119 eluted first (solid, 198 mg, 72%)

¹H-NMR (400 MHz, CDCl₃): δ=0.76-0.81 (m, 4H), 1.62 (m, 1H), 2.03 (s, 3H), 2.39 (s, 3H), 2.46 (s, 6H), 5.18 (s, 2H), 5.86 (s, 1H), 6.61 (s, 2H); LRMS: APCl⁺: m/z 363 [MH⁺].

Further elution provided Example 120 (oil, 25 mg, 9%).

¹H-NMR (400 MHz, CDCl₃): δ=0.68-0.72 (m, 2H), 0.85-0.90 (m, 2H), 1.62 (m, 1H), 2.07 (s, 3H), 2.43 (s, 3H), 2.50 (s, 6H), 5.47 (s, 2H), 5.99 (s, 1H), 6.58 (s, 2H); LRMS: APCl⁺: m/z 363 [MH⁺].

EXAMPLES 121 TO 124

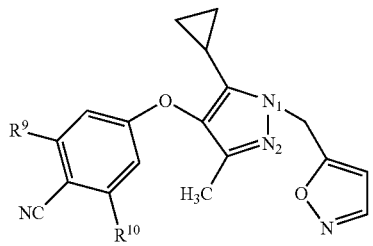

Sodium hydride (60% dispersion in oil, 70 mg, 1.5 mmol) was added to a stirred solution of the benzonitrile of Example 2 (200 mg, 0.75 mmol) in dry N,N-dimethylformamide (5 ml). The reaction mixture was stirred for 30 minutes at room temperature, then the bromoisoxazole of Preparation 23 (243 mg, 0.75 mmol) was added as a solution in N,N-dimethylformamide (1 ml). The reaction mixture was stirred at room temperature for a further 18 hours. The reaction mixture was then concentrated under reduced pressure, diluted with ethyl acetate (30 ml) and washed with brine (20 ml). The organic layer was dried over sodium sulphate, filtered and concentrated under reduced pressure. The residue containing two regioisomers (as identified by TLC) was purified by flash chromatography on silica gel eluting with ethyl acetate:pentane (35:65 to 50:50 by volume). Example 121 was eluted first (39 mg, 15%) followed by Example 122 (8 mg, 3%). Example 123 (50 mg, 19%) and Example 124 (20 mg, 8%) were prepared by a similar method using Example 10 and the bromoisoxazole of Preparation 23 as starting materials.

| Ex No | N alkyl$^n$ | $R^9$; $R^{10}$ Analytical Data |
|---|---|---|
| 121 | N1 | $R^9$=Me; $R^{10}$=Me<br>$^1$H-NMR(400MHz, CDCl$_3$): δ=0.77-0.80(m, 4H), 1.61(m, 1H), 2.11(s, 3H), 2.48(s, 6H), 5.31(s, 2H), 6.14(s, 1H), 6.63(s, 2H), 8.21(s, 1H); LRMS: APCI$^+$: m/z 349[MH$^+$]. |
| 122 | N2 | $R^9$=Me; $R^{10}$=Me<br>$^1$H-NMR(400MHz, CDCl$_3$): δ=0.69-0.71(m, 2H), 0.82-0.85(m, 2H), 1.59(m, 1H), 2.00(s, 3H), 2.47(s, 6H), 5.46(s, 2H), 6.18(s, 1H), 6.58(s, 2H), 8.22(s, 1H); LRMS: APCI$^+$: m/z 349[MH$^+$]. |
| 123 | N1 | $R^9$=H; $R^{10}$=H<br>$^1$H-NMR(400MHz, CDCl$_3$): δ=0.75-0.78(m, 4H), 1.57(m, 1H), 2.12(s, 3H), 5.29(s, 2H), 6.13(s, 1H), 6.97(d, 2H), 7.59(d, 2H), 8.21(s, 1H); LRMS: APCI$^+$: m/z 321[MH$^+$]. |
| 124 | N2 | $R^9$=H; $R^{10}$=H<br>$^1$H-NMR(400MHz, CDCl$_3$): δ=0.67-0.69(m, 2H), 0.81-0.84(m, 2H), 1.58(m, 1H), 2.00(s, 3H), 5.46(s, 2H), 6.19(s, 1H), 6.93(d, 2H), 7.59(d, 2H), 8.23(s, 1H), contaminated by the other regioisomer; LRMS: APCI$^+$: m/z 321[MH$^+$]. |

EXAMPLE 125

4-{[5-Ethyl-1-(1H-imidazol-2-ylmethyl)-3-methyl-1H-pyrazol-4-yl]oxy}benzonitrile

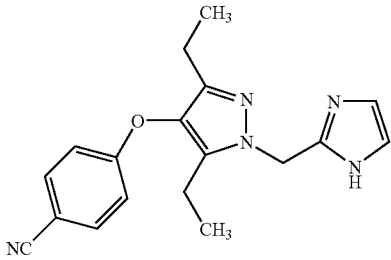

Methanesulphonyl chloride (100 mg, 0.87 mmol) was added to a solution of the imidazole of Preparation 25 (220 mg, 0.87 mmol) and triethylamine (88 mg, 0.87 mmol) in dichloromethane (5 ml). The reaction mixture was stirred at room temperature for 30 minutes. It was then concentrated under reduced pressure and the resulting residue was added to a solution of the benzonitrile of Example 5 (100 mg, 0.42 mmol) in N,N-dimethylformamide (10 ml). Potassium carbonate (175 mg, 1.27 mmol) and potassium iodide (180 mg, 1.08 mmol) were added and the reaction mixture was heated at 140° C. for 6 hours. The reaction mixture was then concentrated under reduced pressure, diluted with dichloromethane (50 ml) and washed with water (20 ml). The organic layer was dried over magnesium sulphate, filtered and concentrated under reduced pressure. The crude product was purified by flash chromatography on silica gel eluting with ethyl acetate then dichloromethane:methanol:ammonia (93:7:1, by volume) to provide the title compound (35 mg, 26%).

$^1$H-NMR (400 MHz, CDCl$_3$): δ=1.03 (t, 3H), 1.15 (t, 3H), 2.43 (q, 2H), 2.58 (q, 2H), 5.33 (s, 2H), 6.93 (d, 2H), 7.05 (s, 2H), 7.57 (d, 2H); LRMS: APCI$^+$: m/z 322 [MH$^+$]; APCI$^-$ m/z 320 [M-H].

EXAMPLES 126 TO 136

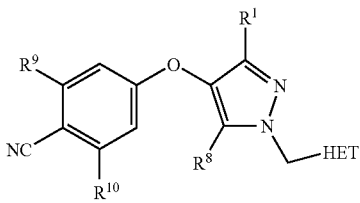

Compounds of the general formula given above were prepared by a similar method to that described for Example 119 using the appropriate benzonitrile and halo-heterocycle as the starting materials.

| Ex No | $R^9$; $R^{10}$; $R^8$; $R^1$ Analytical Data | HET |
|---|---|---|
| 126 (from Ex 4) | $R^9$=Me; $R^{10}$=Me; $R^8$=cPr; $R^1$=cPr<br>$^1$H-NMR(400 MHz, CDCl$_3$): δ=0.62-0.65(m, 2H), 0.75-0.80(m, 6H), 1.39(m, 1H), 1.56(m, 1H), 2.45(s, 6H), 5.32(s, 2H), 6.61(s, 2H), 8.60(s, 2H), 9.18(s, 1H); LRMS: APCI$^+$: m/z 386 [MH$^+$]; 8% yield | pyrimidinyl |
| 127 (from Ex 5) | $R^9$=H; $R^{10}$=H; $R^8$=Et; $R^1$=Et<br>$^1$H-NMR(400 MHz, CDCl$_3$): δ=1.06-1.13(m, 6H), 2.41(q, 2H), 2.57(q, 2H), 5.36(s, 2H), 6.16(s, 1H), 6.96(d, 2H), 7.59 (d, 2H), 8.22(s, 1H); LRMS: APCl$^+$: m/z 323 [MH$^+$]; APCl$^-$ 321 [M-H]$^-$; 9% yield | isoxazolyl |
| 128 (from Ex 5) | $R^9$=H; $R^{10}$=H; $R^8$=Et; $R^1$=Et<br>$^1$H-NMR(400 MHz, CDCl$_3$): δ=1.02(t, 3H), 1.13(t, 3H), 2.40(s, 3H), 2.41(q, 2H), 2.51(q, 2H), 5.23 (s, 2H), 5.91(s, 1H), 6.94(d, 2H), 7.58(d, 2H); LRMS: APCl$^+$: m/z 337 [MH$^+$]; 77% yield | 5-methylisoxazolyl |
| 129 (from Ex 5) | $R^9$=H; $R^{10}$=H; $R^8$=Et; $R^1$=Et<br>$^1$H-NMR(400 MHz, CDCl$_3$): δ=1.02(t, 3H), 1.12(t, 3H), 2.19(s, 3H), 2.32(s, 3H), 2.36-2.46(m, 4H), 4.98 (s, 2H), 6.96(d, 2H), 7.58(d, 2H); LRMS: APCl$^+$: m/z 351 [MH$^+$]; Microanalysis: Found: C, 68.17; H, 6.34; N, 15.83%. C$_{20}$H$_{22}$N$_4$O$_2$ requires C, 68.58; H, 6.28; N, 16.00%; 84% yield | 3,5-dimethylisoxazolyl |

-continued

| Ex No | $R^9$; $R^{10}$; $R^8$; $R^1$ Analytical Data | HET |
|---|---|---|
| 130 (from Ex 5) | $R^9$=H; $R^{10}$=H; $R^8$=Et; $R^1$=Et <br> $^1$H-NMR(400 MHz, CDCl$_3$): δ=0.95(t, 3H), 1.15(t, 3H), 2.45-2.49(m, 4H), 5.39(s, 2H), 6.90(d, 1H), 6.98(d, 2H), 7.21(m, 1H), 7.59(d, 2H), 7.66(t, 1H), 8.56(d, 1H); LRMS: APCl$^+$: m/z 333 [MH$^+$]; Microanalysis: Found: C, 71.71; H, 6.06; N, 16.60%. C$_{20}$H$_{20}$N$_4$O.0.25H$_2$O requires C, 71.32; H, 6.09; N, 16.64%; 41% yield | 2-pyridyl |
| 131 (from Ex 5) | $R^9$=H; $R^{10}$=H; $R^8$=Et; $R^1$=Et <br> $^1$H-NMR(400 MHz, CDCl$_3$): δ = 0.97(t, 3H), 1.11(t, 3H), 2.38(q, 2H), 2.64(q, 2H), 3.78(s, 3H), 5.40(s, 2H), 6.89(s, 1H), 6.93(d, 2H), 7.57(d, 2H); LRMS: APCl$^+$: m/z 336 [MH$^+$]; 11% yield | 1-methylimidazol-2-yl |
| 132 (from Ex 5) | $R^9$=H; $R^{10}$=H; $R^8$=Et; $R^1$=Et <br> $^1$H-NMR(400 MHz, CDCl$_3$): δ=1.06 (t, 3H), 1.15(t, 3H), 2.43(q, 2H), 2.52(q, 2H), 5.44(s, 2H), 6.94(d, 2H), 7.58(d, 2H), 7.77(s, 1H), 8.78(s, 1H); LRMS: APCl$^+$: m/z 339 [MH$^+$]; 12% yield | thiazol-5-yl |
| 133 (from Ex 5) | $R^9$=H; $R^{10}$=H; $R^8$=Et; $R^1$=Et <br> $^1$H-NMR(400 MHz, CDCl$_3$): δ=0.97(t, 3H), 1.15(t, 3H), 2.39-2.48(m, 4H), 5.26(s, 2H), 6.96(d, 2H), 7.01(d, 2H), 7.59(d, 2H), 8.58(brs, 2H); LRMS: APCl$^+$: m/z 333 [MH$^+$]; 33% yield | 4-pyridyl |
| 134 (from Ex 5) | $R^9$=H; $R^{10}$=H; $R^8$=Et; $R^1$=Et <br> $^1$H-NMR(400 MHz, CDCl$_3$): δ=0.94 (t, 3H), 1.10(t, 3H), 2.41(q, 4H), 5.24(s, 2H), 6.92 (d, 2H), 7.26(m, 1H), 7.42(d, 1H), 7.54(d, 2H), 8.39 (s, 1H), 8.51(m, 1H); LRMS: APCl$^+$: m/z 333 [MH$^+$]; 92% yield, ca 85% pure | 3-pyridyl |
| 135 (from Ex 5) | $R^9$=H; $R^{10}$=H; $R^8$=Et; $R^1$=Et <br> $^1$H-NMR(400 MHz, CDCl$_3$): δ=1.03(t, 3H), 1.13(t, 3H), 2.42(q, 2H), 2.49(q, 2H), 5.26(s, 2H), 6.95 (d, 2H), 7.59(d, 2H), 8.57(s, 2H), 9.18(s, 1H); LRMS: APCl$^+$: m/z 334 [MH$^+$]; 10% yield, ca 80% pure | pyrimidin-5-yl |
| 136 (from Ex 7) | $R^9$=H; $R^{10}$=H; $R^8$=cPr; $R^1$=cPr <br> $^1$H-NMR(400 MHz, CDCl$_3$): δ=0.65-0.69(m, 2H), 0.74-0.83 (m, 6H), 1.51-1.58(m, 2H), 5.42(s, 2H), 6.14(s, 1H), 6.97(d, 2H), 7.60(d, 2H), 8.21(s, 1H); LRMS: APCl$^+$: m/z 347 [MH$^+$]; APCl$^-$ 345 [M–H]$^-$; 70% yield | isoxazol-5-yl |

EXAMPLE 137

4-{[3-Cyclopropyl-5-methyl-1-(4H,2,4-triazol-3-ylmethyl)-1H-pyrazol-4-yl]oxy}-2,6-dimethylbenzonitrile

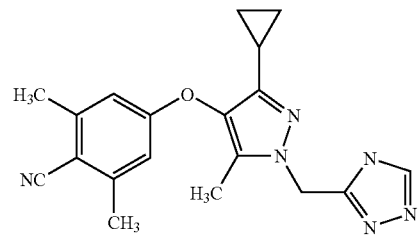

The amide (91 mg, 0.28 mmol) of Example 72 was added to N,N-dimethylformamide dimethyl acetal (4 ml). The reaction mixture was then heated at 120° C. for 2 hours, after which time it was evaporated to an orange oil. This crude intermediate was dissolved in acetic acid (3 ml) and hydrazine hydrate (15 μl, 0.31 mmol) was added. The reaction mixture was then heated at 90° C. for 2 hours, after which time it was concentrated under reduced pressure. The resulting residue was diluted with ethyl acetate (15 ml), washed with saturated aqueous sodium carbonate (10 ml), and then washed with water (10 ml). The organic layer was dried over sodium sulphate, filtered, and then concentrated under reduced pressure. The crude product was purified by flash chromatography on silica gel eluting with dichloromethane:methanol:ammonia (95:5:0.5 by volume) to provide the title compound as a solid (89 mg, 91%).

$^1$H-NMR (400 MHz, CDCl$_3$): δ=0.78-0.81 (m, 4H), 1.64 (m, 1H), 2.12 (s, 3H), 2.47 (s, 6H), 5.33 (s, 2H), 6.63 (s, 2H), 8.06 (s, 1H); LRMS: APCl$^+$: m/z 349 [MH$^+$]; APCl$^-$: m/z 347 [M-H]$^-$.

EXAMPLE 138

4-{[3,5-Diethyl-1-(4H-1,2,4-triazol-3-ylmethyl)-1H-pyrazol-4-yl]oxy}benzonitrile

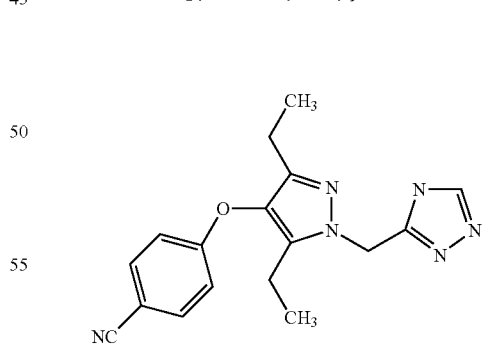

The title compound (240 mg, 52%) was prepared by a similar method to that described for Example 137 using the amide of Example 54 as the starting material.

$^1$H-NMR (400 MHz, CDCl$_3$): δ=1.08 (q, 6H), 2.41 (q, 2H), 2.62 (q, 2H), 5.39 (s, 2H), 6.96 (d, 2H), 7.57 (d, 2H), 8.19 (s, 1H); LRMS: APCl$^+$: m/z 323 [MH$^+$]; APCl$^-$: m/z 321 [M-H]$^-$.

EXAMPLE 139

4-({3,5-Diethyl-1-[(5-methyl-4H-1,2,4-triazol-3-yl)methyl]-1H-pyrazol-4-yl}oxy)benzonitrile

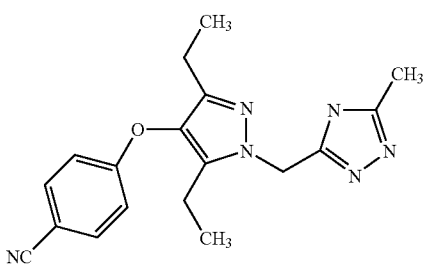

The title compound (130 mg, 36%) was prepared by a similar method to that describe for Example 137 using the amide of Example 54 and N-(1,1-dimethoxyethyl)-N,N-dimethylamine as the starting materials.

$^1$H-NMR (400 MHz, CDCl$_3$): δ=1.04-1.13 (m, 6H), 2.39-2.44 (m, 5H), 2.58 (q, 2H), 5.28 (s, 2H), 6.96 (d, 2H), 7.57 (d, 2H); LRMS:APCl$^+$: m/z 337 [MH$^+$]; APCl$^-$: m/z 335 [M-H]$^-$; Microanalysis: Found: C, 62.95; H, 5.99; N, 24.19%. C$_{18}$H$_{20}$N$_6$O$_3$.0.25H$_2$O requires C, 63.43; H, 6.02; N, 24.66%.

EXAMPLE 140

4-({3,5-Diethyl-1-[(5-methyl-1,3,4-oxadiazol-2-yl)methyl]-1H-pyrazol-4-yl)oxy)benzonitrile

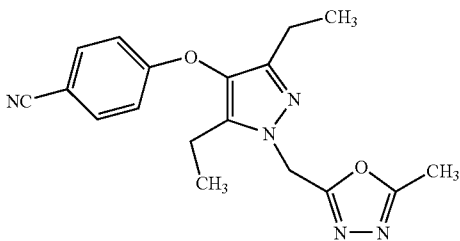

(a) [4-(4-Cyanophenoxy)-3,5-diethyl-1H-pyrazol-1-yl]acetic acid

2M Sodium hydroxide (2 ml) was added to a solution of the ester of Example 34 (800 mg, 2.46 mmol), in methanol (10 ml), and the reaction mixture was then stirred at room temperature for 2 hours. The reaction mixture was evaporated and water (20 ml) was added. The aqueous solution was acidified with 2M hydrochloric acid, until pH 2 was reached. A precipitate formed and this was collected by filtration, washed with water (2×5 ml) and dried, to provide the title compound (701 mg, 95%) as a white solid.

$^1$H-NMR (400 MHz, DMSO-D$_6$): δ=0.93-1.02 (m, 6H), 2.28 (q, 2H), 2.43 (q, 2H), 4.84 (s, 2H), 7.02 (d, 2H), 7.81 (d, 2H); LRMS:APCl$^+$: m/z 300 [MH$^+$]; APCl$^-$: m/z 298 [M-H]$^-$; Microanalysis: Found C, 63.59; H, 5.66; N, 13.91%. C$_{16}$H$_{17}$N$_3$O$_3$.0.25H$_2$O requires C, 63.26, H, 5.76, N, 13.83%.

(b) N'-Acetyl-2-[4-(4-cyanophenoxy)-3,5-diethyl-1H-pyrazol-1-yl]acetohydrazide

The acid of step (a) above (400 mg, 1.34 mmol), acetic hydrazide (109 mg, 1.47 mmol), 1-(3-dimethylaminopropyl)-3-ethylcarbodiimide hydrochloride (372 mg, 1.47 mmol), 1-hydroxybenzotriazole hydrate (192 mg, 1.47 mmol) and N-methylmorpholine (525 mg, 5.36 mmol) were stirred in N,N-dimethylformamide (6 ml) at room temperature for 18 hours. The reaction mixture was then evaporated under reduced pressure and the residue was partitioned between dichloromethane (40 ml) and water (30 ml). The organic layer was dried over magnesium sulphate, filtered, and then concentrated under reduced pressure. The crude product was purified by flash chromatography on silica gel eluting with dichloromethane:methanol:ammonia (93:7:0.5, by volume) to provide the title compound (345 mg, 72%).

$^1$H-NMR (400 MHz, DMSO-D$_6$): δ=0.95-1.01 (m, 6H), 1.83 (s, 3H), 2.26 (q, 2H), 2.44-2.46 (m, 2H), 4.76 (s, 2H), 7.02 (d, 2H), 7.80 (d, 2H), 10.00 (brs, 2H); LRMS:APCl$^+$: m/z 356 [MH$^+$]; APCl$^-$: m/z 354 [M-H]$^-$.

(c) 4-({3,5-Diethyl-1-[(5-methyl-1,3,4-oxadiazol-2-yl)methyl]-1H-pyrazol-4-yl}oxy) benzonitrile Iodine (243 mg, 0.95 mmol) was added portionwise to a solution of triphenylphosphine (250 mg, 0.95 mmol) in dichloromethane (10 ml). The reaction mixture was then stirred for 10 minutes, after which time triethylamine (194 mg, 1.9 mmol) was added, followed by the acetylacetohydrazide of step (b) above (170 mg, 0.48 mmol). The reaction mixture was then stirred at room temperature for 12 hours after which time it was evaporated to dryness and purified by flash chromatography on silica gel eluting with ethyl acetate:pentane (1:1, by volume) to provide the title compound (80 mg, 49%) as 4:1 mixture product:triphenylphosphine oxide.

$^1$H-NMR (400 MHz, CDCl$_3$): δ=1.06-1.13 (m, 6H), 2.41 (q, 2H), 2.54 (s, 3H), 2.59 (q, 2H), 5.39 (s, 2H), 6.96 (d, 2H), 7.44-7.48 (m, 6H, Ph$_3$P=O), 7.51-7.55 (m, 3H, Ph$_3$P=O), 7.58 (d, 2H), 7.64-7.70 (m, 6H, Ph$_3$P=O); LRMS: APCl$^+$: m/z 338 [MH$^+$] 100% and m/z 279 [Ph$_3$P=O.H$^+$].

EXAMPLE 141

4-({3,5-Diethyl-1-((5-methyl-1,3,4-thiadiazol-2-yl)methyl]-1H-pyrazol-4-yl}oxy)benzonitrile

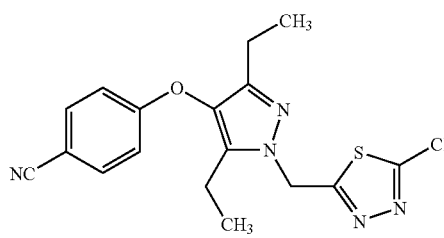

Lawesson's reagent (213 mg, 0.53 mmol) was added to a solution of the acetyl acetohydrazide of step (b) of Example 140 (170 mg, 0.48 mmol) in tetrahydrofuran (10 ml) and the reaction mixture was stirred at room temperature for 18 hours. It was then evaporated to dryness and purified by flash chromatography on silica gel eluting with ethyl acetate:pentane (1:1 then 2:1, by volume) to provide the title compound (80 mg, 47%).

¹H-NMR (400 MHz, CDCl₃): δ=1.01 (t, 3H), 1.11 (t, 3H), 2.40 (q, 2H), 2.52 (q, 2H), 2.73 (s, 3H), 5.56 (s, 2H), 6.91 (d, 2H), 7.56 (d, 2H); LRMS: APCI⁺: m/z 354 [MH⁺].

EXAMPLE 142

4-{[3,5-Diethyl-1-(1,3,4-thiadiazol-2-ylmethyl)-1H-pyrazol-4-yl]oxy]benzonitrile

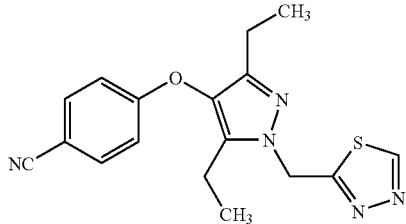

(a) 2-[4-(4-Cyanophenoxy)-3,5-diethyl-1H-pyrazol-1-yl]-N'-formylacetohydrazide

The title compound (290 mg, 51%) was prepared by a similar method to that describe for the acetohydrazide of step (b) of Example 140 using the acid of step (a) of Example 140 and formic hydrazide as the starting materials.

¹H-NMR (400 MHz, DMSO-D₆): δ=0.96-1.03 (m, 6H), 2.28 (q, 2H), 2.44-2.46 (m, 2H), 4.79 (s, 2H), 7.03 (d, 2H), 7.79 (d, 2H), 8.01 (s, 1H), 10.07 (brs, 1H), 10.29 (brs, 1H); LRMS:APCI⁺: m/z 342 [MH⁺]; APCI⁻ m/z 340 [M-H]; Microanalysis: Found C, 59.54; H, 5.63; N, 20.391%. C₁₇H₁₉N₅O₃ requires C, 59.82; H, 5.57; N, 20.53%.

(b) 4-{[3,5-Diethyl-1-(1,3,4-thiadiazol-2-ylmethyl)-1 pyrazol-4-yl]oxy}benzonitrile The title compound (44 mg, 29.5%) was prepared by a similar method to that described for Example 141 using the formyl acetohydrazide of step (a) of Example 142 as the starting material.

¹H-NMR (400 MHz, CDCl₃): δ=1.04 (t, 3H), 1.16 (t, 3H), 2.44 (q, 2H), 2.57 (q, 2H), 5.72 (s, 2H), 6.93 (d, 2H), 7.58 (d, 2H), 9.12 (s, 1H); LRMS: APCI⁺: m/z 340 [MH⁺].

EXAMPLE 143

4-{[3,5-Dicyclopropyl-1-(1H-pyrazol-3-ylmethyl)-1H-pyrazol-4-yl]oxy}benzonitrile

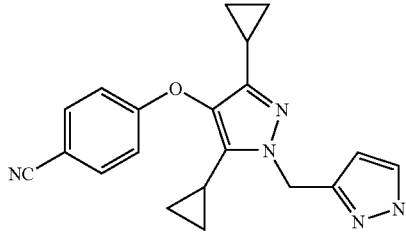

(a) 4-{[1-({1-[(2-Trimethylsilyl-ethoxy)methyl]-1H-pyrazol-3/5-yl}methyl)-3,5-dicyclopropyl-1H-pyrazol-4-yl]oxy}benzonitrile The pyrazole of Preparation 28 (120 mg, 0.49 mmol) was added to a solution of the benzonitrile of Example 7 (88 mg, 0.33 mmol) in N,N-dimethylformamide (5 ml). Potassium carbonate (92 mg, 0.66 mmol) and potassium iodide (54 mg, 0.33 mmol) were added and the reaction mixture was heated at 100° C. for 4 hours. Additional pyrazole of Preparation 28 (100 mg, 0.40 mmol) was added and the reaction mixture was heated at 100° C. for a further 4 hours. The reaction mixture was then concentrated under reduced pressure, diluted with ethyl acetate (75 ml) and washed with water (75 ml). The aqueous layer was extracted again with ethyl acetate (2×75 ml). The organic layers were combined, dried over magnesium sulphate, filtered and concentrated under reduced pressure. The crude product was purified by flash chromatography on silica gel eluting with ethyl acetate:pentane (20:80 to 30:70, by volume) to provide the title compound (68 mg, 43%) as an unknown mixture of regioisomers.

¹H-NMR (400 MHz, CDCl₃): δ=−0.03 (s, 9H), 0.64-0.66 (m, 2H), 0.73-0.79 (m, 6H), 0.88 (t, 2H), 1.44 (m, 1H), 1.53 (m, 1H), 3.56 (t, 2H), 5.41 (s, 2H), 5.59 (s, 2H), 6.07 (s, 1H), 6.95 (d, 2H), 7.43 (s, 1H), 7.60 (d, 2H).

LRMS: APCI⁺: m/z 476 [MH⁺].

(b) Tetrabutylammonium fluoride (1M in tetrahydrofuran, 5 ml) and the benzonitrile of step (a) above were mixed and heated at 70° C. for 35 minutes. The reaction mixture was then poured on to water (50 ml) and extracted with ethyl acetate (3×50 ml). The organic extracts were combined, washed with water (50 ml), dried over magnesium sulphate, filtered and concentrated under reduced pressure. The crude product was purified by preparative HPLC to provide the title compound (18 mg, 37%).

¹H-NMR (400 MHz, CDCl₃): δ=0.64-0.67 (m, 2H), 0.77-0.83 (m, 6H), 1.54-1.60 (m, 2H), 5.45 (s, 2H), 6.32 (s, 1H), 6.99 (d, 2H), 7.61 (d, 2H), 7.68 (s 1H); LRMS: APCI⁺: m/z 346 [MH⁺].

EXAMPLE 144

4-{([3-Cyclopropyl-5-methyl-1-(1H-1,2,3-triazol-5-ylmethyl)-1H-pyrazol-4-yl]oxy}-2,6-dimethylbenzonitrile

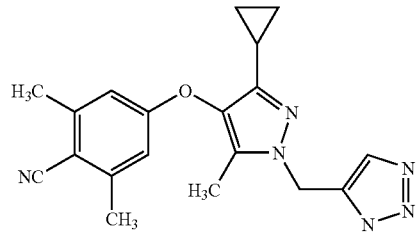

(a) 4-[(3-Cyclopropyl-5-methyl-1-prop-2-ynyl-1H-pyrazol-4-yl)oxy]-2,6-dimethyl benzonitrile The benzonitrile of Example 2 (200 mg, 0.75 mmol) in tetrahydrofuran (1 ml) was added dropwise to a stirred suspension of sodium hydride (60% dispersion in oil, 28 mg, 0.71 mmol) in tetrahydrofuran (4 ml) at 0° C. under nitrogen. The reaction mixture became brown and hydrogen was evolved. Then propargyl bromide (80% wt in toluene, 0.16 ml, 1.5 mmol) was added slowly at 0° C. The reaction mixture was then warmed to room temperature and stirred for 18 hours, after which time it was quenched by the addition of water (10 ml) and concentrated under reduced pressure. The resulting residue was diluted with ethyl acetate (30 ml). The organic layer was washed twice with water (20 ml), then brine (10 ml), dried over sodium sulphate and concentrated under reduced pressure. The crude product was purified by flash chromatography on silica gel eluting with ethyl acetate:cyclohexane (20:80, by volume) to provide the title compound (78 mg, 34%) eluted first compared to the other regioisomer.

¹H-NMR (400 MHz, CDCl₃): δ=0.74-0.81 (m, 4H), 1.61 (m, 1H), 2.14 (s, 3H), 2.04 (t, 1H), 2.48 (s, 6H), 4.78 (s, 2H), 6.65 (s, 2H); LRMS: APCI⁺: m/z 306 [MH⁺].

(b) 4-{[3-Cyclopropyl-5-methyl-1-(1H1,2,3-triazol-5-ylmethyl)-1H pyrazol-4-yl]oxy)-2,6-dimethylbenzonitrile Trimethylsilylazide (50 μl) and the benzonitrile of step (a) above (60 mg, 0.20 mmol) were heated at 150° C. for 20 hours. The reaction mixture was then taken up in diethyl ether (10 ml) and washed with water (10 ml). The organic layer was concentrated under reduced pressure and the crude product was purified by flash chromatography on silica gel eluting with ethyl acetate:cyclohexane (45:55, by volume) to provide the title compound (49 mg, 72%), $^1$H-NMR (400 MHz, CDCl$_3$): δ=0.76-0.80 (m, 4H), 1.62 (m, 1H), 2.09 (s, 3H), 2.47 (s, 6H), 5.31 (s, 2H), 6.62 (s, 2H), 7.60 (s, 1H); LRMS: APCl$^+$: m/z 349 [MH$^+$].

EXAMPLE 145

4-[(3,5-Diethyl-1-methyl-1H-pyrazol-4-yl)oxy]benzonitrile

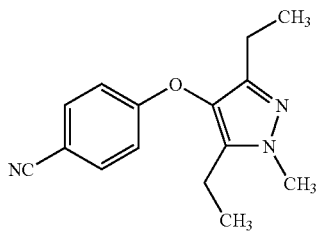

Sodium hydride (60% dispersion in oil, 36 mg, 0.93 mmol) was added to a stirred solution of the benzonitrile of Example 5 (150 mg, 0.62 mmol) in dry N,N-dimethylformamide (5 ml), under nitrogen. The reaction mixture was stirred for 30 minutes at room temperature, during which time hydrogen was evolved, and then methyl iodide (0.25 ml, 0.76 mmol) was added. It was then stirred at room temperature for a further 48 hours, after which time it was quenched by the addition of water (10 ml), and concentrated under reduced pressure. The mixture was then extracted with dichloromethane (20 ml). The organic layers were dried over magnesium sulphate and concentrated under reduced pressure. The crude product was purified by flash chromatography on silica gel eluting with ethyl acetate:pentane (1:1, by volume) to provide the title compound (110 mg, 69%).

$^1$H-NMR (400 MHz, CDCl$_3$): δ=1.06-1.13 (m, 6H), 2.40 (q, 2H), 2.49 (q, 2H), 3.76 (s, 3H), 6.96 (d, 2H), 7.58 (d, 2H); LRMS:APCl$^+$: m/z 256 [MH$^+$]; Microanalysis: Found: C, 69.75; H, 6.74; N, 16.33%. C$_{15}$H$_{17}$N$_3$O requires C, 70.56; H, 6.71; N, 16.46%

EXAMPLE 146 TO 147

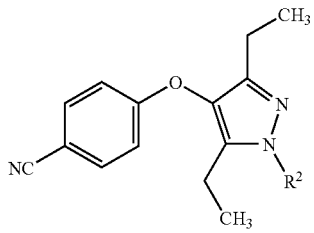

Compounds of the general formula given above were prepared by a similar method to that described for Example 145 using the appropriate alkyl halide as the starting material.

| Ex No | R$^2$ | Analytical Data |
|---|---|---|
| 148 | nPr | $^1$H-NMR(400MHz, CDCl$_3$): δ=0.94(t, 3H), 1.04-1.12(m, 6H), 1.81-1.89(m, 2H), 2.40(q, 2H), 2.49(q, 2H), 3.93(t, 2H), 6.95(d, 2H), 7.57(d, 2H); LRMS: APCl$^+$: m/z 284[MH$^+$]; 45% yield |
| 147 | Et | $^1$H-NMR(400MHz, CDCl$_3$): δ=1.07-1.12(m, 6H), 1.93(t, 3H), 2.41(q, 2H), 2.49(q, 2H), 4.04(q, 2H), 6.96(d, 2H), 7.57(d, 2H); LRMS: APCl$^+$: m/z 270[MH$^+$]; 65% yield |

EXAMPLE 148

4-[(3,5-Diethyl-1-phenyl-1H-pyrazol-4-yl)oxy]benzonitrile

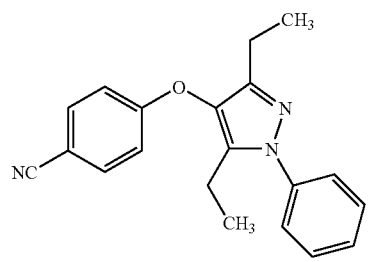

The benzonitrile of Preparation 11 (150 mg, 0.61 mmol) was dissolved in acetic acid (30 ml) and ethanol (20 ml). Phenyl hydrazine hydrochloride (100 mg, 0.69 mmol) was added and the reaction mixture was stirred at room temperature, under nitrogen, for 18 hours. It was then concentrated under reduced pressure, and the residue was partitioned between an aqueous solution of potassium carbonate (20 ml) and dichloromethane (25 ml). The organic layer was separated, washed with brine, dried over magnesium sulphate, and then concentrated under reduced pressure. The crude product was purified by flash chromatography on silica gel eluting with ethyl acetate:pentane (1:1, by volume) to provide the title compound (160 mg, 82%).

$^1$H-NMR (400 MHz, CDCl$_3$): δ=0.99 (t, 3H), 1.18 (t, 3H), 2.50 (q, 2H), 2.59 (q, 2H), 7.05 (d, 2H), 7.39 (m, 1H), 7.44-7.48 (m, 4H), 7.61 (d, 2H); LRMS: APCl$^+$: m/z 318 [MH$^+$].

EXAMPLE 149

4-[4-(4-Cyanophenoxy)-3,5-diethyl-1+pyrazol-1-yl] benzonitrile

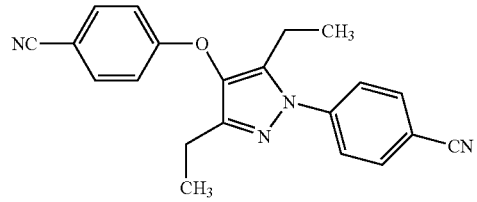

The title compound (130 mg, 62%) was prepared by a similar method to that described for Example 148 using 4-cyanophenylhydrazine as the starting material.

$^1$H-NMR (400 MHz, CDCl$_3$): δ=1.06 (t, 3H), 1.18 (t, 3H), 2.49 (q, 2H), 2.68 (q, 2H), 7.04 (d, 2H), 7.61-7.65 (m, 4H), 7.79 (d, 2H); LRMS: APCl$^+$: m/z 343 [MH$^+$]; Microanalysis: Found: C, 73.56; H, 5.31; N, 16.31%. C$_{21}$H$_{18}$N$_4$O requires C, 73.68; H, 5.26; N, 16.37%

EXAMPLE 150

4-[(3,5-Dicyclopropyl-1-pyridin-3-yl-1H-pyrazol-4-yl)oxy]-2,6-dimethylbenzonitrile

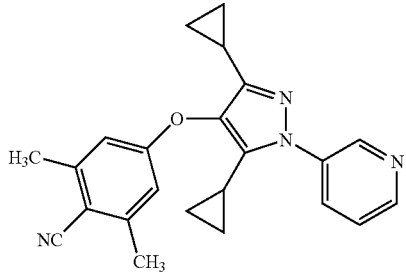

Copper iodide (13 mg, 0.07 mmol) was added to a solution of the benzonitrile of Example 4 (200 mg, 0.68 mmol) and potassium carbonate (197 mg, 1.43 mmol) in toluene (2 ml) in a Reactivial®. The reaction mixture was degassed, then 3-bromopyridine (79 μl, 0.82 mmol) and (1R,2R)-(−)-1,2-bis(methylamino)cyclohexane (20 mg, 0.14 mmol) were added successively. The reaction was then sealed and heated at 110° C. for 24 hours. The reaction mixture was then diluted with ethyl acetate (20 ml), filtered through a pad of silica and then washed with more ethyl acetate (15 ml). The filtrate was concentrated under reduced pressure and the crude product was purified by preparative HPLC to provide the title compound (11 mg, 4%), $^1$H-NMR (400 MHz, CD$_3$OD): δ=0.65-0.67 (m, 2H), 0.79-0.86 (m, 6H), 1.64 (m, 1H), 1.77 (m, 1H), 2.48 (s, 6H), 6.83 (s, 2H), 7.65 (m, 1H), 8.23 (d, 1H), 8.60 (brs 1H), 8.94 (brs, 1H); LRMS APCl$^+$: m/z 371 [MH$^+$].

EXAMPLE 151

4-[(3,5-Dicyclopropyl-1-pyrimidin-5-yl-1H-pyrazol-4-yl)oxy]-2,6-dimethylbenzonitrile

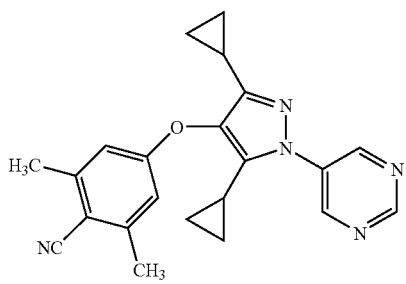

The title compound (25 mg, 10%) was prepared by a similar method to that described for Example 150 using 5-bromopyrimidine as the starting material.

$^1$H-NMR (400 MHz, CDCl$_3$): δ=0.75-0.79 (m, 2H), 0.84-0.94 (m, 6H), 1.61-1.74 (m, 2H), 2.53 (s, 6H), 6.71 (s, 2H), 9.17 (brs, 3H); LRMS: APCl$^+$: m/z 372 [MH$^+$].

EXAMPLE 152

4-[(3,5-Diethyl-1'H-1,4'-bipyrazol-4-yl)oxy]benzonitrile

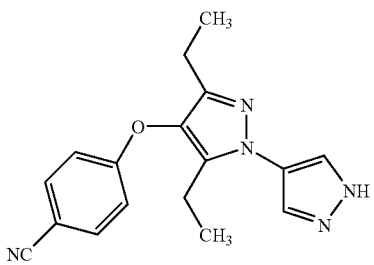

(a) 4-{[1'-(4-Methoxybenzyl)-3,5-dimethyl-1'H-1,4'-bipyrazol-4-yl]oxy}benzonitrile The title compound (177 mg, 100%) was prepared by a similar method to that described for Example 150 using the benzonitrile of Example 5 and 4-iodo-1-(4-methoxybenzyl)-1H-pyrazole as the starting materials.

$^1$H-NMR (400 MHz, CDCl$_3$): δ=1.00 (t, 3H), 1.13 (t, 3H), 2.43 (q, 2H), 2.51 (q, 2H), 3.80 (s, 3H), 5.26 (s, 2H), 6.89 (d, 2H), 6.96 (d, 2H), 7.00 (d, 2H), 7.23 (s, 1H), 7.59 (d, 2H), 7.66 (s, 1H), contaminated with N-methylpyrrolidinone and Example 5; LRMS: APCl$^+$: m/z 428 [MH$^+$].

(b) Trifluoroacetic acid (3 ml) was added to a solution of the benzonitrile of step (a) above (175 mg, 0.41 mmol) in dichloromethane (3 ml). The reaction mixture was then stirred at room temperature for 3.5 hours. A further portion of trifluoroacetic acid was added (5 ml), and the reaction mixture was heated at 65° C. for a further 4 hours, after which time, the reaction was evaporated and azeotroped with toluene. The resulting residue was partitioned between dichloromethane (20 ml) and a saturated aqueous sodium bicarbonate solution (15 ml). The organic layer was then separated and the aqueous layer was extracted again with dichloromethane (15 ml). The extracts were combined, dried over magnesium sulphate, filtered and concentrated under reduced pressure. The crude product was purified by flash chromatography on silica gel eluting with ethyl acetate:pentane (elution gradient from 2:98 to 40:60, by volume) to provide the title compound (19 mg, 15%) as a solid.

$^1$H-NMR (400 MHz, CDCl$_3$): δ=1.05 (t, 3H), 1.18 (t, 3H), 2.49 (q, 2H), 2.57 (q, 2H), 5.58 (brs, 1H), 7.04 (d, 2H), 7.62 (d, 2H), 7.85 (s, 2H); LRMS: APCl$^+$: m/z 308 [MH$^+$]; APCl$^-$: m/z 306 [M-H].

EXAMPLE 153

Examples of specific compounds, tested in Screen 1.0 as described above for functional progesterone antagonism, are illustrated in the table below.

| Example No. | IC$_{50}$ (nM) |
|---|---|
| 4 | 9 |
| 65 | 3 |
| 71 | 4 |
| 87 | 5 |
| 126 | 3 |
| 146 | 6 |

The invention claimed is:
1. A compound of formula (I),

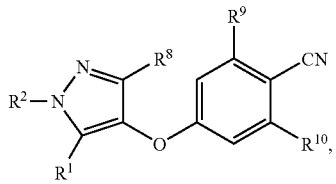

or pharmaceutically acceptable derivatives thereof, wherein:
$R^1$ represents H, $C_{1-6}$alkyl, $C_{1-6}$alkyloxy, $C_{3-8}$cycloalkyl, or halo;
$R^2$ represents H, $C_{1-6}$alkyl (optionally substituted by $R^3$), phenyl (optionally substituted by CN), or Het;
$R^3$ represents OH, CN, Het, —$R^4$—$C_{1-6}$alkyl, or $CONR^5R^6$;
$R^4$ represents —$CO_2$—, or —O—;
$R^5$ and $R^6$ independently represent H, $C_{1-6}$alkyl (optionally substituted by $OR^7$) or $C_{3-8}$cycloalkyl;
$R^7$ represents H or $C_{1-6}$alkyl;
Het represents a five or six membered aromatic heterocyclic group containing (i) from one to four nitrogen heteroatom(s) or (ii) one or two nitrogen heteroatom(s) and one oxygen or one sulphur heteroatom or (iii) one or two oxygen or sulphur heteroatom(s), said heterocyclic group being optionally substituted by one or more groups selected from CN and $C_{1-6}$alkyl;
$R^8$ represents $C_{1-6}$alkyl, $C_{1-6}$alkyloxy, $C_{3-8}$cycloalkyl, or halo;
$R^9$ and $R^{10}$ independently represent H, $C_{1-6}$alkyl, $C_{1-6}$alkyloxy, CN, $CF_3$ or halo.

2. A compound according to claim 1, wherein $R^1$ represents $C_{3-8}$cycloalkyl.

3. A compound according to claim 1, wherein $R^2$ represents $C_{1-6}$alkyl.

4. A compound according to claim 1, wherein $R^3$ represents $CONR^5R^6$.

5. A compound according to claim 1, wherein $R^4$ represents O.

6. A compound according to claim 1, wherein $R^5$ represents H.

7. A compound according to claim 1, wherein $R^6$ represents $C_{1-6}$alkyl.

8. A compound according to claim 1, wherein $R^8$ represents $C_{3-8}$cycloalkyl.

9. A compound according to claim 1, wherein $R^9$ represents H or halo.

10. A compound according to claim 1, wherein $R^{10}$ represents H or halo.

11. A compound according to claim 1 selected from the group consisting of:
4-{[3,5-dicyclopropyl-1-(2-hydroxyethyl)-1H-pyrazol-4-yl]oxy}-2,6-dimethylbenzonitrile;
2-[4-(4-cyano-3,5-dimethylphenoxy)-3,5-dicyclopropyl-1H-pyrazol-1-yl]-N-methylacetamide;
2-[4-(4-cyano-3,5-dimethyl-phenoxy)-3,5-dicyclopropyl-1H-pyrazol-1-yl]-acetamide;
2-[4-(4-cyanophenoxy)-3,5-dicyclopropyl-1H-pyrazol-1-yl]-N-methyl-acetamide;
2-[4-(4-cyano-3-methyl-phenoxy)-3,5-dicyclopropyl-1H-pyrazol-1-yl]-N-methyl-acetamide;
2-[4-(3-chloro-4-cyanophenoxy)-3,5-dicyclopropyl-1H-pyrazol-1-yl]-N-methyl-acetamide;
4-{[1-(cyanomethyl)-3,5-diethyl-1H-pyrazol-4-yl]oxy}benzonitrile;
4-{[1-(cyanomethyl)-3,5-diethyl-1H-pyrazol-4-yl]oxy}-2,6-dimethylbenzonitrile;
4-({3,5-dicyclopropyl-1-[(pyrimidin-5-yl)methyl]-1H-pyrazol-4-yl}oxy)-2,6-dimethylbenzonitrile;
4-({3,5-diethyl-1-[(isoxazol-3-yl)methyl]-1H-pyrazol-4-yl}oxy)-benzonitrile; and the pharmaceutically acceptable derivatives thereof.

12. A pharmaceutical formulation comprising a compound according to claim 1, or a pharmaceutically acceptable derivative thereof, together with a pharmaceutically acceptable excipient, diluent or carrier.

13. A method of treatment of a mammal to treat endometriosis, uterine fibroids (leiomyomata), menorrhagia, adenomyosis, primary and secondary dysmenorrhoea (including symptoms of dyspareunia, dyschexia and chronic pelvic pain), or chronic pelvic pain syndrome including treating said mammal with an effective amount of a compound according to claim 1, or with a pharmaceutically acceptable derivative or composition thereof.

14. A method according to claim 13 wherein the disease or disorder is endometriosis and/or uterine fibroids.

* * * * *